US008916342B2

(12) United States Patent
Cheng

(10) Patent No.: US 8,916,342 B2
(45) Date of Patent: *Dec. 23, 2014

(54) IDENTIFICATION OF HIGH GRADE OR ≥ CIN2 FOR EARLY STAGES AND LATE STAGES DETECTION, SCREENING, AND DIAGNOSIS OF HUMAN PAPILLOMAVIRUS (HPV) AND HPV-ASSOCIATED CANCERS

(75) Inventor: Shuling Cheng, Fremont, CA (US)

(73) Assignee: OncoHealth Corp., Mountain View, CA (US)

( * ) Notice: Subject to any disclaimer, the term of this patent is extended or adjusted under 35 U.S.C. 154(b) by 452 days.

This patent is subject to a terminal disclaimer.

(21) Appl. No.: 13/319,312

(22) PCT Filed: May 6, 2010

(86) PCT No.: PCT/US2010/033944
§ 371 (c)(1),
(2), (4) Date: Nov. 7, 2011

(87) PCT Pub. No.: WO2010/129821
PCT Pub. Date: Nov. 11, 2010

(65) Prior Publication Data
US 2012/0052486 A1 Mar. 1, 2012

Related U.S. Application Data

(60) Provisional application No. 61/215,589, filed on May 7, 2009, provisional application No. 61/131,991, filed on Jun. 13, 2008, provisional application No. 61/192,912, filed on Sep. 22, 2008, provisional application No. 61/199,013, filed on Nov. 12, 2008.

(51) Int. Cl.
*C12Q 1/70* (2006.01)
*G01N 33/53* (2006.01)
*G01N 33/574* (2006.01)
*G01N 33/569* (2006.01)

(52) U.S. Cl.
CPC .... *G01N 33/56983* (2013.01); *G01N 33/57411* (2013.01); *G01N 2333/025* (2013.01); *G01N 2800/56* (2013.01)
USPC .................. 435/5; 435/7.1; 435/7.23

(58) Field of Classification Search
None
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,045,447 A | 9/1991 | Minson |
| 5,057,411 A | 10/1991 | Lancaster et al. |
| 5,061,025 A | 10/1991 | Debesis |
| 5,109,465 A | 4/1992 | Klopotek |
| 5,183,755 A | 2/1993 | Ohmoto et al. |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,591,574 A | 1/1997 | Orth et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A | 9/1997 | Orth et al. |
| 5,679,509 A | 10/1997 | Wheeler et al. |
| 5,695,770 A | 12/1997 | Raychaudhuri et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |

(Continued)

FOREIGN PATENT DOCUMENTS

| | | |
|---|---|---|
| CN | 1675550 | 9/2005 |
| CN | 03825051.9 | 11/2005 |

(Continued)

OTHER PUBLICATIONS

Kashmiri et al. (Methods. 2005; 36:25-34).*
Tamura et al. (Journal of Immunology. 2000; 164 (3):1432-1441).*
Greenspan et al (Nature Biotechnology. 7; 10:936-937 (1999).*
Wu et al. (Journal of Virology. 2006; 87: 1181-1188).*
Pillai et al. (Cancer Epidemiology, Biomarkers, and Prevention; 1996; 5: 329-335).*
Christensen et al. (Virology. 1996; 223: 174-184).*
Pavai et al. (Romanian Journal of Morphology ad Embryology. 2006; 47 (3): 229-234).*

(Continued)

*Primary Examiner* — Shanon A Foley
(74) *Attorney, Agent, or Firm* — Yi-Shan Yang; Fenwick & West LLP

(57) ABSTRACT

A method and a kit for determining a disease stage of a papilloma virus infection in a human subject is disclosed. The method comprises: obtaining a sample from said human subject, said sample consisting of a tissue sample comprising proteins or a cell sample comprising proteins; contacting said sample with one or more antibodies that specifically bind to one or more recombinant HPV proteins; determining a presence, absence, or amount of at least one protein in said sample that specifically binds to said antibodies and determining said disease stage of papilloma virus infection in said human subject based on said determined presence, absence, or amount of said one or more proteins.

21 Claims, 18 Drawing Sheets

(56) References Cited

U.S. PATENT DOCUMENTS

| | | | |
|---|---|---|---|
| 6,329,167 | B1 | 12/2001 | Patterson et al. |
| 6,355,424 | B1 | 3/2002 | Lorincz et al. |
| 6,420,106 | B1 | 7/2002 | Gyllensten et al. |
| 6,489,105 | B1 | 12/2002 | Matlashewski et al. |
| 6,524,825 | B1 | 2/2003 | Mizzen et al. |
| 6,528,278 | B2 | 3/2003 | Patterson |
| 6,709,832 | B1 | 3/2004 | Von Knebel Doeberitz et al. |
| 6,743,593 | B2 | 6/2004 | Hu |
| 6,827,933 | B2 | 12/2004 | Orth et al. |
| 6,884,786 | B1 | 4/2005 | Kieny et al. |
| 6,890,514 | B2 | 5/2005 | Mathur et al. |
| 6,900,035 | B2 | 5/2005 | Mizzen et al. |
| 6,933,123 | B2 | 8/2005 | Hu et al. |
| 6,939,687 | B2 | 9/2005 | Patterson et al. |
| 7,001,995 | B1 | 2/2006 | Neeper et al. |
| 7,078,061 | B2 | 7/2006 | Debad et al. |
| 7,157,233 | B2 | 1/2007 | Fischer et al. |
| 7,361,460 | B2 | 4/2008 | Williams et al. |
| 7,399,467 | B2 * | 7/2008 | Lu et al. .................. 424/130.1 |
| 7,455,973 | B2 | 11/2008 | Fischer et al. |
| 7,501,261 | B2 | 3/2009 | Meijer et al. |
| 7,510,838 | B2 | 3/2009 | Fischer et al. |
| 7,732,166 | B2 * | 6/2010 | Cheng ........................ 435/69.1 |
| 7,838,215 | B2 | 11/2010 | Gombrich et al. |
| 7,888,032 | B2 | 2/2011 | Patterson et al. |
| 8,278,056 | B2 * | 10/2012 | Cheng ............................ 435/7.1 |
| 2001/0034021 | A1 | 10/2001 | Muller et al. |
| 2003/0044870 | A1 | 3/2003 | Sehr et al. |
| 2003/0143571 | A1 | 7/2003 | Sharp et al. |
| 2003/0190602 | A1 | 10/2003 | Pressman et al. |
| 2004/0018487 | A1 * | 1/2004 | Lu et al. ............................ 435/5 |
| 2004/0170644 | A1 | 9/2004 | Mailere et al. |
| 2004/0175695 | A1 | 9/2004 | Debad et al. |
| 2004/0260157 | A1 | 12/2004 | Montes et al. |
| 2005/0037017 | A1 | 2/2005 | Mizzen et al. |
| 2005/0037342 | A1 | 2/2005 | Mathur et al. |
| 2005/0042600 | A1 | 2/2005 | Hu et al. |
| 2005/0142541 | A1 | 6/2005 | Lu et al. |
| 2005/0147621 | A1 | 7/2005 | Higgins et al. |
| 2005/0159386 | A1 | 7/2005 | Kieny et al. |
| 2005/0255460 | A1 | 11/2005 | Lu et al. |
| 2005/0255468 | A1 | 11/2005 | Ridder et al. |
| 2005/0260566 | A1 | 11/2005 | Fischer et al. |
| 2006/0002929 | A1 | 1/2006 | Khare et al. |
| 2006/0029943 | A1 | 2/2006 | Hermonat et al. |
| 2006/0039919 | A1 | 2/2006 | Chang et al. |
| 2006/0121516 | A1 | 6/2006 | Norman et al. |
| 2006/0147906 | A1 | 7/2006 | Zwerschke et al. |
| 2006/0153864 | A1 | 7/2006 | Gissmann et al. |
| 2006/0154238 | A1 | 7/2006 | Hu et al. |
| 2006/0160069 | A1 * | 7/2006 | Chau et al. ......................... 435/5 |
| 2006/0172285 | A1 | 8/2006 | Patterson |
| 2006/0269967 | A1 | 11/2006 | Chen et al. |
| 2006/0286595 | A1 | 12/2006 | Fischer et al. |
| 2004/0048833 | A1 | 3/2007 | Sprencher et al. |
| 2005/0147061 | A1 | 3/2007 | Carlson et al. |
| 2007/0065810 | A1 | 3/2007 | Schlegel |
| 2007/0099199 | A1 | 5/2007 | Lu et al. |
| 2007/0117167 | A1 | 5/2007 | Malinowski et al. |
| 2007/0166699 | A1 * | 7/2007 | Zwerschke et al. ................ 435/5 |
| 2007/0190062 | A1 | 8/2007 | Malinowski et al. |
| 2007/0190529 | A1 | 8/2007 | Ridder et al. |
| 2008/0038738 | A1 | 2/2008 | Weigum et al. |
| 2008/0267982 | A1 | 10/2008 | Kiselev |
| 2009/0047660 | A1 | 2/2009 | Lu et al. |
| 2009/0075377 | A1 | 3/2009 | Lu et al. |
| 2009/0104597 | A1 | 4/2009 | Gombrich et al. |
| 2009/0148864 | A1 | 6/2009 | Fischer et al. |
| 2012/0052486 | A1 * | 3/2012 | Cheng ................................ 435/5 |

FOREIGN PATENT DOCUMENTS

| | | |
|---|---|---|
| EP | 0256321 | 2/1988 |
| GB | 2379220 | 5/2003 |
| JP | 2002296274 | 10/2002 |
| JP | 2007503208 | 2/2007 |
| JP | 2007537705 | 12/2007 |
| TW | 95142312 | 11/2006 |
| TW | 100100781 | 1/2010 |
| TW | 201012932 | 4/2010 |
| TW | 201043958 | 12/2010 |
| WO | WO9700888 | 1/1997 |
| WO | WO9910375 | 3/1999 |
| WO | WO0204007 A2 | 1/2002 |
| WO | WO2004085683 | 10/2004 |
| WO | WO2005008248 | 1/2005 |
| WO | 2005063286 | 7/2005 |
| WO | WO2005/063286 | 7/2005 |
| WO | WO2005088311 | 9/2005 |
| WO | WO2006083984 | 8/2006 |
| WO | WO2007059492 | 5/2007 |
| WO | WO2007095320 | 8/2007 |
| WO | WO2009042488 | 4/2009 |
| WO | 2009079192 | 6/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Fiedler et al. (Journal of General Virology, 2005; 86: 3235-3241).*
Klaes et al. (American Journal of Surgical Pathology. 2002; 26 (11): 1389-1399).*
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.
Non-final Office Action for U.S. Appl. No. 12/456,054 dated Sep. 25, 2012.
Final Office Action for U.S. Appl. No. 12/456,053 dated Sep. 24, 2012.
JH Joen et al., "Immunocytochemical detection of HPV16E7 in cervical smear." 2007. Experimental and Molecular Medicine, vol. 39, No. 5, 621-628.
C Liang et al., "Biomarkers of HPV in Head and Neck Squamous Cell Carcinoma." 2012, Cancer Research. Published online Sep. 18, 2012.
D Holzinger et al., "Viral RNA Patterns and High Viral Load Reliably Define Oropharynx Carcinomas wit hActive HPV16 Involvement." 2012, Cancer Research. Published online Sep. 18, 2012.
AG Ostor et al., "Natural History of Cervical Intraepithelial Neoplasia: A Critical Review." 1993 International Journal of Gyncological Pathology . 12:186-192.
Advisory action for U.S. Appl. No. 12/456,055 dated Mar. 12, 2012.
Taiwan Patent Office Communication, Notice of Allowance, for TW Patent App. No. 95142312, Feb. 11, 2014.
Japan Patent Office Communication for JP Patent App. No. 2011-513505, Jan. 14, 2014.
Japan Patent Office communication for JP Patent App. No. 2012-509989, Jan. 21, 2014.
China Patent Office communication for CN Patent App. No. 200980131077.x, Jan. 24, 2014.
LA Selvey et al., 1992 Journal of Virological Methods, 37, 119-128. "An ELISA capture assay for the E7 transforming proteins of HPV16 and HPV18."
H Griesser et al., 2004 Analyt Quant Cytol Histol 26, 241-245. "Correlation of Immunochemical Detection of HPV L1 capsid protein in Pap Smears with Regression of High-Rist HPV Positive Milk/Moderate Dysplasia."
European Patent Office Communication dated Jan. 30, 2013 for Application No. 12164498.3-2402/2522756.
Non-final Office Action for U.S. Appl. No. 13/585,509 dated Jan. 1, 2013.
Qiao et al., 2008. "A New HPV-DNA Test for Cervical-Cancer Screening in Developing Regions: a Cross-Sectional Study of Clinical Accuracy in Rural China." Lancet Oncology 9: 929-936.
Zhao et al., 2010. "Performance of High-Risk Human Papillomavirus DNA Testing as a Primary Screening for Cervical Cancer: a Pooled

(56) References Cited

OTHER PUBLICATIONS

Analysis of Individual Patient Data from 17 Population-Based Studies from China." Lancet Oncology 11: 1160-1171.
Zhao et al., 2011. "Pooled Analysis of a Self-Sampling HPV DNA Test as a Cervical Cancer Primary Screening Method." JNCI 104: 1-11.
Arbyn et al., 2010. "HPV-Based Cervical-Cancer Screening in China." World Health Organization GLOBOCAN 2008. Published online Nov. 12, 2010. http://globocan.iarcfr/.
Wong et al., 2011. "Efficacy of Abbott Real Time High Risk HPV Test in Evaluation of Atypical Squamous Cells of Undetermined Significance from an Asian Screening Population." Journal of Clinical Virology 51, 136-138.
Petignat et al., 2012. "Is It Time to Introduce HPV Seld-Sampling for Primary Cervical Cancer Screening?" Editorial, JNCI. 104 (3): pp. 1-2.
Japan Patent Office Communication dated Apr. 2, 2013 for Application No. 2011-513504.
Final Office Action for U.S. Appl. No. 12/456,054 dated May 14, 2013.
Taiwan Patent Office Communication dated Apr. 8, 2013 for Application No. 100100781.
Taiwan Patent Office Communication dated Apr. 3, 2013 for Application No. 095142312.
China Patent Office Communication dated Apr. 1, 2013 for Application No. 200980131078.4.
China Patent Office Communication dated Mar. 13, 2013 for Application No. 200980131077.X.
Final Office action for U.S. Appl. No. 13/319,312 dated Jul. 24, 2014.
Final Office action for U.S. Appl. No. 12/590,747 dated Jul. 23, 2014.
Final Office action for U.S. Appl. No. 12/456,055 dated Sep. 9, 2014.
European Patent Office Communication for EPO Patent App. No. 09762929910842601.6 dated Jul. 14, 2014.
European Patent Office Communication for EPO Patent App. No. 12164498.3 dated Jun. 26, 2014.
European Patent Office Communication for EPO Patent App. No. 09762928.1 dated Aug. 26, 2014.
Japan Patent Office Communication for JP Patent App. No. 2011-513504 dated May 2, 2014.
Japan Patent Office Communication for JP Patent App. No. 2012-548021 dated Jul. 15, 2014.
China patent Office Communication for CN Patent App. No. 201080020175.9 dated May 28, 2014.
Notice of Allowance for U.S. Appl. No. 12/456,053 dated Jun. 13, 2014.
Notice of Allowance for U.S. Appl. No. 12/456,054 dated Jun. 13, 2014.
Non-final Office action for U.S. Appl. No. 11/559,366 dated Dec. 5, 2008.
Final Office action for U.S. Appl. No. 11/559,366 dated May 5, 2009.
Notice of Allowance for U.S. Appl. No. 11/559,366 dated Jan. 4, 2010.
Non-final Office action for U.S. Appl. No. 12/082,740 dated Jun. 12, 2009.
Final Office action for U.S. Appl. No. 12/082,740 dated Aug. 20, 2010.
Notice of Allowance for U.S. Appl. No. 12/082,740 dated Mar. 8, 2011.
Non-final Office action for U.S. Appl. No. 12/456,053 dated May 31, 2011.
Non-final Office action for U.S. Appl. No. 12/456,054 dated Aug. 17, 2011.
Non-final Office action for U.S. Appl. No. 12/456,055 dated Jul. 22, 2011.
EPO Communication for App. No. 09762928.1-1223/2300824, dated Aug. 15, 2011.
Extended European Search Report for App. No. 09762928.1-1223/2300824, dated Jul. 22, 2011.
EPO Communication for App. No. 06846299.3-2402/1951915, dated Apr. 7, 2010.

Extended European Search Report for App. No. 06846299.3-2402/1951915, dated Jan. 8, 2010.
International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authorigy for Int'l App. No. PCT/US2009/003538, dated Oct. 15, 2009.
Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan. 26, 2012.
Advisory action for U.S. Appl. No. 12/082,740 dated Nov. 3, 2010.
Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
de Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.
Nair, Pillai 2005 Human papillomavirus and disease mechanisms: relevance to oral and cervical cancers Oral Diseases 11, 350-359.
Nindl, et al. 1994. Antibodies against linear and conformational epitopes of the human papillomavirus (HPV) type 16 E6 and E7 oncoproteins in sera of cervical cancer patients. Arch. Virol. 137:341-353.
Sasagawa, et al. 2003. Mucosal immunoglobulin-A and -G responses to oncogenic human papilloma virus capsids. Int J Cancer. Apr. 10, 2003; 104(3): 328-35.
Snijders, et al. 2006 HPV-mediated cervical carcinogenesis: concepts and clinical implications J Pathol 2006; 208: 152-164.
Stacey, et al. 1992 "Expression of human papillomavirus type 16 E6 protein by recombinant baculovirus and use for detection of anti-E6 antibodies in human sera", Journal of General Virology vol. 73, pp. 2337-2345.

(56) References Cited

OTHER PUBLICATIONS

Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.
Tornesello, et al. 2004 Analysis of human papillomavirus type-16 variants in Italian women with cervical intraepithelial neoplasia and cervical cancer J Med Virol.; 74(1): 117-26.
Viscidi, et al. 1993. Serologic response in human papillomavirus-associated invasive cervical cancer. Int. J. Cancer 55:780-784.
Lehtinen, et al.2001. Human papillomavirus infection, risk for subsequent development of cervical neoplasia and associated population attributable fraction. J Clin Virolo 22:117-124.
Mougin, et al. 2001. Epidemiology of cervical papillomavirus infections. Recent knowledge. Press Med 30: 1017-23.
TIPO Search Report and Communication for Taiwan Invention Patent Application No. 095142312, Mar. 24, 2012. English search report on p. 1.
TIPO Search Report and Communication for Taiwan Invention Patent Application No. 098119611, Mar. 22, 2012. English search report on p. 1.
TIPO Search Report and Communication for Taiwan Invention Patent Application No. 098119612, Mar. 13, 2012. English search report on p. 1.
Volgareva et al., Protein p16 as a marker of dysplastic and neoplastic alterations in cervical epithelial cells. BMC Cancer 2004, 4:58. pp.
Liu et al., Preparation of monoclonal antibodies against human papillomavirus 16 E6 protein. Journal of Monoclonal Antibody, vol. 11 No. 3-4, Dec. 1995. English abstract on p. 3.
Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.
Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.
Non-final Office action for U.S. Appl. No. 12/456,053 dated Apr. 6, 2012.
Final Office action for U.S. Appl. No. 12/456,054 dated Apr. 16, 2012.
Advisory Action for U.S. Appl. No. 12/456,054 dated Jun. 13, 2012.
J Melnikow et al., 1998. "Natural history of Cervical Squamous Intraepithelial Lesions: A meta-Analysis." 1998 vol. 92, No. 4, pp. 727-735.
European Patent Office Communication dated Oct. 23, 2012 for Application No. 09762928.1, PCT/US2009003537.
Non-final Office Action for U.S. Appl. No. 13/029,131 dated Nov. 9, 2012.
Sep. 18, 2013 USPTO Non-Final Office Action for U.S. Appl. No. 12/456,053.
Sep. 30, 2013 USPTO Non-Final Office Action for U.S. Appl. No. 12/456,054.
Sep. 30, 2013 USPTO Final Office Action for U.S. Appl. No. 12/590,747.
US Patent Office non-final Office action for U.S. Appl. No. 13/319,312, Feb. 28, 2014.
China Patent Office communication for CN Patent App. No. 200980131078.4, Feb. 12, 2014.
Pillai et al., Cancer Epidemiology Biomarkers & Prevention 1996; 5: 329-335. "The presence of human papillomavirus-16/-18 E6, p53, and Bcl-2 protein in cervicovaginal smears from patients with invasive cervical caner".
Pavai et al., Romanian Journal of Morphology and Embryology 2006, 47(3): 229-234. "Comparative detection of high-risk HPV (16, 18, 33) in ervical bioptic material of County Hospital of Tg. Mures."
Non-final Office action for U.S. Appl. No. 12/456,055 dated Mar. 21, 2014.
Non-final Office action for U.S. Appl. No. 12/590,747 dated Mar. 26, 2014.
Final Office action for U.S. Appl. No. 13/520,021 dated Apr. 14, 2014.
Apgar et al., "The Bethesda System Terminology." Am Fam Physician 2003; 68: 1992-1998.
Kovanda et al., "Characterization of a Novel Cutaneous Human Papillomavirus Genotype HPV-125." PLosOne 2011; vol. 6 e22414Vol.
Narechania et al., "Phylogenetic incongruence among Oncogenic Genital Alpha Human Papillomaviruses." J. Virol. 2005, 79(24): 15503.
Rudikoff et al., "Single amino acid substitution altering antigen-binding specificity." Proc. Natl. Acad. Sci 1982 vol. 79 1979-1982.
European Patent Office Communication for EPO Patent App. No. 097629299 dated Feb. 27, 2014.
China patent Office Communication for CN Patent App. No. 2010800609626 dated Mar. 10, 2014.
Liu et al., "Fixed-cell immunoperoxidase Technology." China Academic Journal, Production Technology. 1993 vol. 23 No. 2 pp. 37-38.
Taiwan Intellectual Property Office Notice of Allowance for TW Patent App. No. 098119612 dated May 9, 2014.
Tindle RW et al., 1990 Journal of General Virology. 71, 1347-1354. "Identification of B epitopes in human papillomavirus type 16 E7 open reading frame protein."
Santa Cruz Biotechnology, Inc. Product Data Sheet for sc-18114 E6-AP (C-19). 2006.
EPO Communcation for Application No. 12164498.3 dated on Sep. 28, 2012.
MA Romanos et al., 1995. Production of a phosphorylated GST::HPV-6 E7 Fusion Protein Using a Yeast Expression Vector and Glutathione S-transferase Fusions. Gene. 152, 137-138.
Partial European Search Report for Application No. 12164498, dated Sep. 19, 2012.
T. Ristriani et al., 2001. "Specific Recognition of Four-way DNA Junctions by the C-terminal Zinc-binding Domain of HPV Oncoprotein E6." J. Mol. Biol. 305, 729-739.
KLMC Franken et al., 2000. "Purificaiton of His-Tagged PRoteins by Immobilized Chelate Affinity Chromatography: The Benefits from the Use of Organic Solvent." Protein Expression and Purification 18, 95-99.
Y. Nomine et al., 2001. "A strategy for optimizing the monodispersity of fusion proteins: application to purification of recombinant HPV E6 oncoprotein." Protein Engineering. 14, No. 4 pp. 297-305.
JA DeVoti et al., 2004. "Failure of Gamma Interferon but Not Interleukin-10 Expression in Response to Human Papillomavirus Type 11 E6 PRotein in Respiratory Papillomatosis." Clinical and Vaccine Immunology 11(3) 538-547.
TIPO Search Report and Communication for Taiwan Invention Patent Application No. 098119612, Oct. 5, 2012. Search Report Brief is on p. 1.
European Patent Office Communication dated Jun. 6, 2013 for Application No. 10842601.6.
European Patent Office Communication dated Jul. 18, 2013 for Application No. 10772861.0.
Non-final Office action dated Jul. 3, 2013 for U.S. Appl. No. 12/456,055.
Santer et el., 2007 Carcinogenesis, vol. 28 No. 12 pp. 2511-2520. "Human papillomavirus type 16 E7 oncoprotein inhibits apoptosis mediated by nuclear insulin-like growth factor-binding protein-3 by enhancing its ubiquitin/proteasome-dependent degradation."
Non-final Office action dated Jul. 11, 2013 for U.S. Appl. No. 13/585,509.
China Patent Office Communication dated Jul. 19, 2013 for Application No. 201080020175.9.
Taiwan Patent Office Communication dated Aug. 22, 2013 for Application No. 100100781.
Zhao et al., 2013 Cancer Prevention Research. Published OnlineFirst Jul. 22, 2013. "An Evaluation of Novel, Lower-Cost Molecular Screening Test for Human Papillomavirus in Rural China."
Shi et al., 2009 American Journal of Epidemiology vol. 170 No. 6. 708-716. "Human papillomavirus testing for cervical cancer screening: results from a 6-year prospective study in rural China."
Belinson et al., Am J. Clin Pathol 2011; 135:790-795. "A population-based clinical trial comparing endocervical high-risk HPV testing using hybrid capture 2 and Cervista from the SHENCCAST II study."

(56) References Cited

OTHER PUBLICATIONS

Dockter et al., 2009 Journal of Clinical Viroogy 45, 51: 539-547. "Analytical characterization of the APTIMA HPV assay."
Wong et al., 2011 Journal of Clinical Virology 51 (2011) 136-138. "Efficacy of Abbott real time high risk HPV test in evaluation of atypical squamous cells of undetermined significance from and Asian screening population."
Branca et al., 2005 Am J Clin Pathol 124: 113-121. "Survivin as a marker of cervical intraepithelial neoplasia and high-risk human papillomavirus and a predictor of virus clearance and prognosis in cervical cancer."
Branca et al., 2006 J Clin Pathol 59: 40-47. "Aberrant expression of VEFG-C is related to grade of cervical intraepithelial neoplasia (CIN) and high risk HPV but does not predict virus clearance after treatment of CIN or prognosis of cervical cancer."
Lambert et al., 2006 Experimental and Molecular Pathology 80: 192-196. "p16INK4A expression in cervical premalignant and malignant lesion."
Giannoudis et al., 2000 British J. Cancer 81:424-7. "Differential expression of p53 and p21 in low grade cervical squamous intraepithelial lesions infected with low, intermediate, and high risk human papillomaviruses."
Saqi et al., 2002 "Overexpression of p16INK4A in liquid-based specimens (SurePath) as marker of cervical dysplasia and neoplasia." 27: 365-370.
Park et al., 1998 "HPV-16-releated proteins as the serologic markers in cervical neoplasis." Gynecologic oncology 69, 47-55.
Lie et al., 1999 Int J Gynecol Pathol 18(1): 5-11."Expression of p53, MDM2, and p21 proteins in high-grade cervical intraepithelial neoplasia and relationship to human papillomavirus infection."
Aug. 30, 2013 EPO Office communication for EPA No. 09762928.1.
Sep. 9, 2013 USPTO Communication for U.S. Appl. No. 13/520,021.
Fiedler et. al., 2004 FASEB Journal express article. High Level HPV-16 E7 oncoprotein expression correlates with reduced pRb-levels in cervical biopsies.
European Patent Office Communication dated Dec. 3, 2012 for Application No. 09762929.9, PCT/US2009003538.
Oltersdorf et el., 1987. "Identification of Human Papillomavirus Type 16 E7 Protein by Monoclonal Antibodies." J. Gen. Virol. 68, 2933-2938.
Jochmus et al., 1999. "Chimeric Virus-like Partiles of the Human Papillomavirus Type 16 (HPV 16) as a Prophylactic and Therapeutic Vaccine." Archives of Medical Research. 30, 269-274.
HyTest News. Mar. 2008, pp. 1-8. Advanced ImmunoChemical, Finland.
Mattil-Fritz et al., 2008. "Immunotherapy of equine sarcoid: dose-escalation trial for the use of chimeric papullomavirus-like particles." Journal of General Virology 89, 138-147.
Rizk et al., 2008. "Reactivity pattern of 92 monoclonal antibodies with 15 human papillomavirus types." Journal of General Virology, 89, 117-129.
Dec. 20, 2013 USPTO Non-Final Office Action dated Dec. 20, 2013 for U.S. Appl. No. 13/520,021.
Caceres-Cortes et al.,Implication of Tyrosine Kinase Receptor and Steel Factor in Cell Density-dependent Growth in Cervical Cancers and Leukemias. Cancer Research. 2001;61:6281-6289.
SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."
S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."
J Doorbar, (2006) Clinical Science 1, 10, 525-541. "Molecular biology of human papillomavirus infection and cervical cancer."
M Fiedler et al., (2004) The FASEB Journal vol. 18 pp. 1120-1122. "High level HPV-16 E7 oncoprotein expression correlates with reduced pRb-levels in cervical biopsies."

KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."
M Fiedler et al., (2005) Journal of General Virology, 86, 3235-3241. "Expression of the high-risk human papillomavirus type 18 and 45 E7 oncoproteins in cervical carcinoma biopsies."
E Guccione et al., (2002) Virology 283, 20-25. "Comparative Analysis of the Intracellular Location of the High- and Low-Risk Human Papillomavirus Oncoproteins."
H Valdovinos-Torres et al., (2008) The Open Virology Journal vol 2. 15-23. "Different Isoforms of HPV-16 E7 Protein are Present in Cytoplasm and Nucleus."
T Li et al., (2001) Carcinogenesis vol. 22. No. 6 pp. 929-934. "Human papillomavirus type 16 is an important infections factor in the high incidence of esophageal cancer in Anyang area of China."
Blevins et al., Applied and Environmental Microbiology 2007, pp. 1501-1513. "Adaptation of a Luciferase Gene Reporter Aand lac ExpressionSystem to Borrelia burgdorferi."
EA Mirecka et al., (2006) Protein Expression and Purification 48, 281-291. "Expression and purification of His-tagged HPV16 E7 protein active in pRb binding!".
MS Lechner et al., (1994) Journal of Virology, Jul. 1994, p. 4262-4273. "Inhibition of p53 DNA Binding by Human Papillomavirus E6 Proteins."
B Bjorndal et al., (2003) Protein Expression and Purification 31 (2003) 47-55. "Expression and purification of receptor for activated C-kinase 1 (RACK1)."
ND Christensen et al., (1996) Virology 223, 174-184. "Surface Conformational and Linear Epitopes on HPV-16 and HPV•18 L1 Virus-like Particles as Defined by Monoclonal Antibodies"
Y Nomine et al., (2001) Protein Engineering vol.14 No. 4 pp. 297-305, "A strategy for optimizing the monodispersity of fusion proteins: application to purification of recombinant HPV E6 oncoprotein."
ND Christensen et al., (1994) Journal o/General Virology (1994), 75, 2271-2276. "Assembled baculovirus-expressed human papillomavirus type 11 LI capsid protein virus-like particles are recognized by neutralizing monoclonal antibodies and induce high titres of neutralizing antibodies."
T Oltersdorf et al., (1987) J. gen. Viral. (1987), 68, 2933-2938. "Identification of Human Papillomavirus Type 16 E7 Protein by Monoclonal Antibodies."
P Di Bonito et al., (2006) Infectious Agents and Cancer 2006, 1:6. "Serum antibody response to Human papillomavirus (HPV) infections detected by a novel ELISA technique based on denatured recombinant HPVl6 L1, L2, E4, E6 and E7 proteins."
JF Kearney et al., (1979) The Journal of Immunology, V 123 No. 4 p. 1548-1550. "A New Mouse Myeloma Cell Line That Has Lost Immunoglobulin Expression But Permits the Construction of Antibody-Secreting Hybrid Cell Lines."
K Seedorf et al., The Embo Journal 1987, vol. 6, pp. 139-144. Identification of Early Proteins of the Human Papilloma Viruses Type 16 (HPV 16) and Type 18 (HPV 18) in Cervical Carcinoma Cells.
D Patel et al., (1989) J. gen. Virol. (1989),70,69-77. "Reactivities of Polyclonal and Monoclonal Antibodies Raised to the Major Capsid Protein of Human Papillomavirus Type 16."
S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."
AK Graham et al., (1991) Clin Pathol 1991;44:96-101. "Simultaneous in situ genotyping and phenotyping of human papillomavirus cervical lesions: Comparative sensitivity and specificity."
HG Kochel et al., (1991) Inl. J. Cancer: 48, 682-688. "Occurrence of Antibodies to Lt, L2, E4 and E7 Gene Products of Human Papillomavirus Types 6b, 16 and 18 Among Cervical Cancer Patients and Controls."
AK Ghosh et al., (1993) Int. J. Cancer: 53. 591-596. "Serological Responses to HPV 16 in Cervical Dysplasia and Neoplasia: Correlation of Antibodies to E6 With Cervical Cancer."

(56) References Cited

OTHER PUBLICATIONS

SA Jenison et al., (1990) The Journal of Infectious Disease162:60-69. "Evidence of Prevalent Genital-Type Human Papillomavirus Infections in Adults and Children."
T Fule et al., (2006) Virology 348, 289-396. "The presence of human papillomavirus 16 in neural structures and vascular endothelial cells."
Tommasino et al., Oncogene 1993, vol. 8, pp. 195-202. HPV16 E7 Protein Associates with the Protein Kinase p22 CDK2 and Cyclin A.
de Villiers et at., Virology 2004, vol. 324, pp. 17-27. "Classification of Papillomaviruses".
Banks et al., J. gen. Virol. 1987, vol. 68, pp. 1351-1359, "Identification of human papillomavirus type 18 E6 polypeptide in cells derived from human cervical carcinomas".
Thermo Scientific, Product Data Sheet for Human Papilloma Virus type 16-E7 (HPV 16-e7) Ab-1 (TVG701Y) Mouse Monoclonal Antibody. Dec. 8, 2011.
BioDesign Internation, Product Data Sheet for MAb to HPV16 E7 protein 716-218. Feb. 1, 2006.
BioDesign Internation, Product Data Sheet for MAb to HPV16 E7 protein 716-325. Aug. 3, 2005.
Chemicon International, Product Data Sheet for Mouse anti-human Papilloma Virus 16,18 E6 (C1P5) Monoclonal Antibody. Nov. 10, 2000.
Dako, Product Data Sheet for Monoclonal Mouse anti-Human Papillomavirus Clone K1H8. 2010.
G Volgareva et al., BMC Cancer 2004, 4:58. "Protein p16 as a marker of dysplastic and neoplastic alterations in cervical epithelial cells."
Digene Corporation, "hc2 HPV DNA Test," Ref. 5198-1220, 2007, 56 pages.
Matlashewski G., et al. The expression of human papillomavirus type 18E6 proteins in bacteria and the production of anti-E6 antibodies J Gen Virol (1986) 67: 1909-1916.
Radhakrishna pillai et al 1998 High-risk human papillomavirus infection and E6 protein expression in lesions of the uterine cervix Pathobiology 66(5) 240-246.
Ressler et al 2007 High-risk human popillomavirus E7 oncoprotein detection in cervical squamous cell carcinoma Clin Cancer Res 13(23) 7067-7072.
Androphy et al 1987 Identification of the HPV-16 E6 protein from transformed mouse cells and human cervical carcinoma cell lines EMBO 6(4) 989-992.
Andersson et al 2006 Expression of E6/E7 mRNA from high rishn human papillomavirus in relation to CIN grade, viral load and p161NK4a Int J oncology 29:70-711.
Keegan et al 2009 Comparison of HPV detection technologies: Hybrid capture 2, preTect HPV prooer and analysis of HPV DNA viral load in HPV 16, HPV 18 and HPV 33 E6/E7 mRNA.
Inoue et al 1990 A novel monoclonal antibody against squamous cell carcinoma Jpn J Cancer res 81:176-182.
Arbyn et al., 2009. J Cell Mol Med. vol. 13 No. 4 648-659. "Triage of women with equivocal or low-grade cervical cytology results: a meta-analysis of the HPV test positivity rate".
Andersson et al., 2006. International Journal of Oncology 29: 705-711. "Expression of E6/E7 mRNA from 'high risk' human papillomavirus in relation to CIN grade, viral load and p16INK4a".
Balasubramanian et al., Cancer Epidemiol Biomarkers Prey 2009;18:3008-3017. "Evaluation of an ELISA for p16INK4a as a Screening Test for Cervical Cancer".
Cardenas-Turanzas et al., Gyn Oncology 107 (2007) S138-S146. "The clinical effectiveness of optical spectroscopy for the in vivo diagnosis of cervical intraepithelial neoplasia: Where are we?".
Castle et al., 2010. AACCP. Benefits and risks of HPV testing in cervical cancer screening See Online/Articles DOI:10.1016/S1470-2045(09)70360-2.
Castle et al., American Journal of Obstetrics & Gynecology Oct. 2007 "Risk assessment to guide the prevention of cervical cancer".
Choi et al., Biosensors and Bioelectronics 20 (2005) 2236-2243. "Adenoviral p53 effects and cell-specific E7 protein-protein interactions of human cervical cancer cells".

Cole et al., Journal of Virology, Jun. 1986, vol. 58. No. 3. p. 991-995. "Genome Organization and Nucleotide Sequence of Human Papillomavirus Type 33, Which is Associated with Cervical Cancer".
Cole et al., J. Mol. Biol. (1987) 193, 599-608. "Nucleotide Sequence and Comparative Analysis of the Human Papillomavirus Type 18 Genome Phylogeny of Papillomaviruses and Repeated Structure of the E6 and E7 Gene Products".
Sawaya 2008 Annals of Internal Medicine vol. 148 • No. 7 p. 557 "Adding Human Papillomavirus Testing to Cytology for Primary Cervical Cancer Screening: Shooting First and Asking Questions Later".
Fuchs et al., Journal of Virology, May 1986, p. 626-634. vol. 58, No. 2 "Epidermodysplasia Verruciformis-Associated Human Papillomavirus 8: Genomic Sequence and Comparative Analysis".
Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".
Gravitt et al., Vaccine 265 (2008) K42-K52. "New Technologies in Cervical Cancer Screening".
Kulasingam et al., Obstetrics & Gynecology vol. 107, No. 2, Part 1, Feb. 2006 Cost-effectiveness of Extending Cervical Cancer Screening Intervals Among Women With Prior Normal Pap Tests:.
Mao et al., Int. J. Cancer: 120, 2435-2438 (2007) "Evaluation of a new p16INK4a ELISA test and a high-risk HPV DNA test for cervical cancer screening: Results from proof-of-concept study".
Molden et al., Int. J. Cancer: 114, 973-976 (2005) "Predicting CIN2 when detecting HPV mRNA and DNA by PreTect HPV-Proofer and consensus PCR: a 2-year follow-up of women with ASCUS or LSIL Pap smear".
Marimatsu et al., Am J Clin Pathol 2005;123:716-723 "High-Throughput Cervical Cancer Screening Using Intracellular Human Papillomavirus E6 and E7 mRNA Quantification by Flow Cytometry".
NCCN Clinical Practice Guidelines in Oncology™ v.2. 2007 Cervical Cancer Screening.
Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".
Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".
Trope et al., Journal of Clinical Microbiology, Aug. 2009, p. 2458-2464. "Pe rformance of Human Papillomavirus DNA and mRNA Testing Strategies for Women with and without Cervical Neoplasia".
Schiffman et al., Arch Pathol Lab Med—vol. 127, Aug. 2003. "Findings to Date From the ASCUS-LSIL Triage Study (ALTS)." pp. 946-949.
Woodman et al., "The natural history of cervical HPV infection: unresolved issues." Nature Review Cancer, vol. 7 | Jan. 2007 | 11.
Ronco et al., BMC Women's Health 2008, 8:23. "New paradigms in cervical cancer prevention: opportunities and risks">.
Talora et al., Genes Dev. 2002 16: 2252-2263. Specific down-modulation of Notch1 signaling in cervical cancer cells is required for sustained HPV-E6/E7 expression and late steps of malignant transformation.
Tungteakkhun wr al., Arch Virol (2008) 153:397-408. "Cellular binding partners of the human papillomavirus E6 protein".
Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.
Ronco et al., "Effi cacy of human papillomavirus testing for the detection of invasive cervical cancers and cervical intraepithelial neoplasia: a randomised controlled trial:." Published Online Jan. 19, 2010.
Schneider-Gadicke et al., The EMBO Journal vol. 5 No. 9 pp. 2285-2292, 1986. "Different human cervical carcinoma cell lines show similar transcription patterns of human papillomavirus type 18 early genes."

(56) References Cited

OTHER PUBLICATIONS

Wentzensen et al., Disease Markers 23 (2007) 315-330. "Biomarkers in cervical cancer screening."
Molder et a;., Cancer Epidemiology Biomarkers and Prevention. 2005, 14, p. 367. Comparison of Human Papillomavirus Messeger DNA and DNA detection: A crodd sectional study of 4136 wk e > 30 years of age with a 2, year fikkiw-up of high=grade squamous intraepitehlial Lesion.
Sawaya et al., 2005. www.nejm.org May 10, 2007. "HPV Vaccination—More Answers, More Questions."
Perez et al., 2009. 25th International Papillomavirus Conference, Sweden. "Detection of HPV E6/E7 Oncoportens in Cervical Cancer."
Parkin et al., Int. J. Cancer: 80, 827-841 (1999). "Estimates of the Worldwide Incidence of 25 Major Cancers in 1990."
Schneider et al., 1991 Int. j. Gynecol Pathol. 10:1-14 "Prevalence of Human Papillomavirus Genomes in Tissue from the Lower Genital Tract as Detected by Molecular in situ hybridization."
Segnan et al., 1994 European Journal of Cancer vol. 30, 873-875. "Cervical cancer screening. Human benefits and human costs in the evaluation of screening programmes."
Partridge et al., 2008 J. National Compr. Cancer Network 6: 58-82. Abstract only.
Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."
Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product."
Dyson et al., Science 1989. 243: 934-937. "The Human Papilloma Virus-16 E7 Oncoprotein is Able to Bind to the Retinoblastoma Gene Product."
Zerfass et al., J. Virol. 1995, 69(10):6389. "Sequential activation of cyclin E and cyclin A gene expression by human papillomavirus type 16 E7 through sequences necessary for transformation."
Zerfass-Thome et al., 1996 Oncogene 13:2323-2330. "Inactivation of the cdk inhibitor p27KIP1 by the human papillomavirus type 16 E7 oncoprotein. "
Saint, M., G. Gildengorin, and G. F. Sawaya. 2005. Current Cervical Neoplasia Screening Practices of Obstetriciaqn/ Gynecologists in the US. Am. J. Obstet. Gynecol. 192:414-421.
Final Office action for U.S. Appl. No. 12/456,076 dated May 24, 2012.
Dorland's Pocket Medical Dictionary, P420, 25th Edition, 1995, W,B, Saunders Company. Philadelphia, Pennsylvania, 19106.
Non-final Office Action for U.S. Appl. No. 12/590,747 dated Aug. 15, 2012.
Kashmiri et al., Methods. 2005; 36:25-34.
Tamura et al., Journal of Immunology. 2000; 164:1432-1441.
Greenspan et al., Nature Biotechnology. 1999; 7:936-937.
Gillison et al., Journal of National Cancer Institute. 2008; 100:407-420.
Wu et al., Journal of General Virology. 2006; 87, 1181-1188.
Http://www.biology-online.org/dictionary/Native_protein; Mar. 16, 2010.
Taiwan Patent Office Communication dated Oct. 7, 2013 for Application No. 098119612.
European Patent Office Communication dated Oct. 28, 2013 for Application No. 12164498.3-1404.
Notice of Allowance for U.S. Appl. No. 12/456,076 dated Aug. 1, 2012.
Examiner-Initiated Interview Summary and Amendment after Final initiated by the Examiner for U.S. Appl. No. 12/456,076 dated Aug. 1, 2012.
Bosch, et al 1995. Prevalence of human papillomavirus in cervical cancer: a worldwide perspective. J Natl Cancer Inst 87:796-802.
Doeberitz, Magnus Von Knebel "New Molecular tools for efficient screening of cervical cancer", Disease Markers 17 (2001) 123-128.
Fisher, et al. "The Association of Human Papillomavirus Type 16 E6 and E7 Antibodies with stage of Cervical Cancer", Gynecologic Oncology 61,73-78 (1996) Article No. 0099.
Guimaraes, et al. 2005. "Immunohistochemical expression of p16INK4a and bcl-2 according to HPV type and to the progression of cervical squamous intraepitheliallesions". J Histochem Cytochem. 53: 509-16).
Hagensee, et al. "Detection of Cervical Antibodies to Human Papillomavirus Type 16 (HPV-16) Capsid Antigens in Relation to Detection of HPV-16 DNA and Cervcal Lesions",The Jourrnal of Infectious Diseases 2000; 181: 1234-9.
Kiviat, et al. 1993. Specific human papillomavirus types as the causal agents of most cervical intraepithelial neoplasia: implications for current views and treatment. J Natl Cancer Inst 85: 934-35.
Koutsky, et al. 1992. A cohort study of the risk of cervical intraepithelial neoplasia grade 2 or 3 in relation to papillomavirus infection. N Engl J med 327:1272-1278. Abstract Only.
Kuroda, et al. 2005. The human papillomavirus E6 and E7 inducible oncogene, hWAPL, exhibits potential as a therapeutic target. Br J Cancer 92:290-3.
Li, et al. 2005. Regulation of apoptosis by papillomavirus E6 oncogene. World J Gastroenterol 11:931-37.
Longworth, et al., 2004. Pathogenesis of human papillomavirus in differentiating epithelia. Microbiol Mol Bioi Rev 68: 362-72.
Madrigal, et al. 1997. In vitro antigene therapy targeting HPV-16 E6 and E7 in cervical carcinoma. Gynecol Oncol 64: 18-25.
Meschede, et al. "Antibodies agains Early Proteins of Human Papillomaviruses as Diagnostic Markers for Invasive Cervical Cancer" Journal of Clinical Microbiology Feb. 1998, pp. 475-480.
Munoz, et al. 2003. Epidemiologic classification of human papillomavirus types associated with cervical cancer. N Engl J Med 348:518-27.
Park, et al. 1995. Molecular biology of cervical cancer and its precursors. Cancer 76: 1902-13.
Park, et al. "HPV-16-Related Proteins as the Serolgic Markers in Cervical Neoplasia", Gynecologic Oncology 69,47-55 (1998).
Parkin, et al. 1993. Estimates of the worldwide incidence of eighteen major cancers in 1985. Int J Cancer 54:594-606.
Sehr, et al. "A generic capture ELISA for recombinant proteins fused to glutathione S-transferase: validation for HPV serology" Journal of ImmunoloQical Methods 253 (2001) 153-162.
Solomon, et al. 2002. The 2001 Bethesda Systems. Terminology for reportinQ results of cervical cytoloQY. JAMA 287:2114-19.
Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.
Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and #7 Proteins" Journal of Clinical MicrobioloQY Sep. 1994 pp. 2216-2230.
Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.
Veress, et al. "Human Papillomavirus DNA and Anti-HPV Secretory IgA Antibodies in Cytologically Normal Cervical Specimens" Journal of Medical Virology 43:201-207-(1994).
Viscid!, et al. 1993. Serologic response in human papillomavirus-associated invasive cervical cancer. Int. J. Cancer 55:780-784.
Walboomers, et al. "Human Papillomavirus is a Necessary Cause of Invasive Cervical Cancer Worldwide", Jouranl of PatholoQv 189: 12-19 (1999).
Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.
Zumbach, et al "Antibodies Against Oncoproteins E6 and E7 of Human Papillomavirus Types 16 and 18 in Cervical-Carcinoma Pat-

(56) References Cited

OTHER PUBLICATIONS ents from Russia", Int. J. Cancer 85, 313-318 (2000) [Publication of the International Union Against Cancer].

Fitzgerald Industries International Inc., Product Data Sheet for Monoclonal Antibody to human Papillomavirus (Early Protein), Human, Clone BF7. 2006.

Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.

Gabriella et al., BMC Cancer. 2007, vol7, pp25. Characterization of antibodies in single-chain format against the E7 oncoprotein of the human papillomavirus type 16 and their improvement by mutagenesis.

Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.

Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.

Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prev. 17:2536-2545.

Dehn, D., K. C. Torkko, and K. R. Shroyer. 2007. Human Papillomavirus Testing and Molecular Markers of Cervical Dysplasia and Carcinoma. Cancer Cytopathology 111:1-14.

O'Sullivan, J. P., R. P. A'Hern, P. A. Chapman, L. Jenkins, R. Smith, and A. a. Nafussi. 1998. A case-control study of truepositive versus false-negative cervical smears in women with cervical intraepithelial neoplasia (CIN) III. Cytopathology 9:155-161.

Yim, E.-K., and J.-S. Park. 2006. Biomarkers in Cervical Cancer. Biomarker Insights 1:215-225.

Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.

Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology 48:4646-4648.

Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.

Woodman, C. B. J., S. I. Collins, and L. S. Young. 2007. The natural history of cervical HPV infection: unresolved issues. Nature Reviews Cancer 7:11-22.

Stacey, et al. 1992. "Expression of human papillomavirus type 16 E6 protein by recombinant baculovirus and use for detection of anti-E6 antibodies in human sera", Journal of General Virology vol. 73, pp. 2337-2345.

* cited by examiner

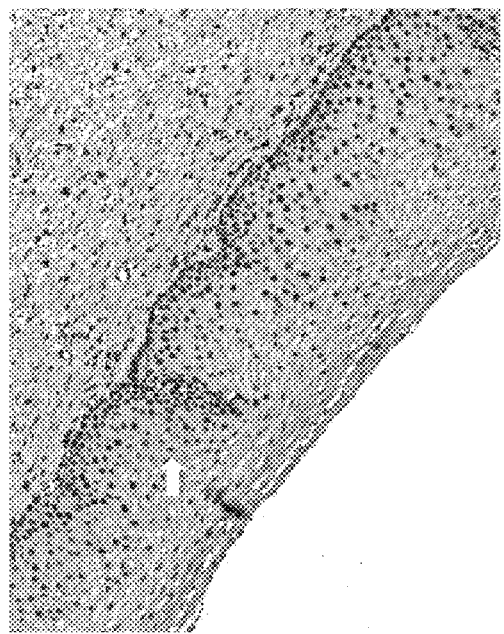
Figure 12B
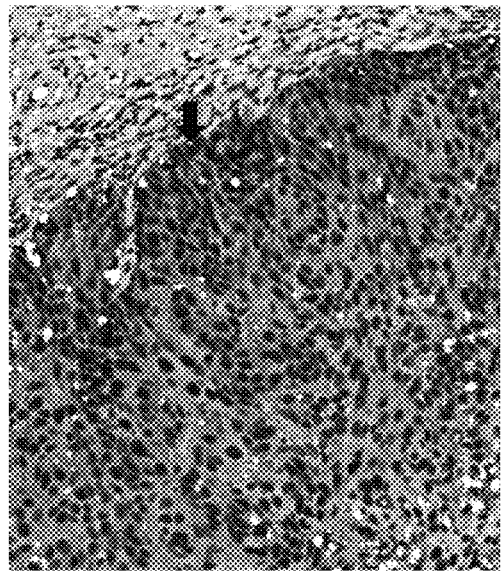
Figure 12A
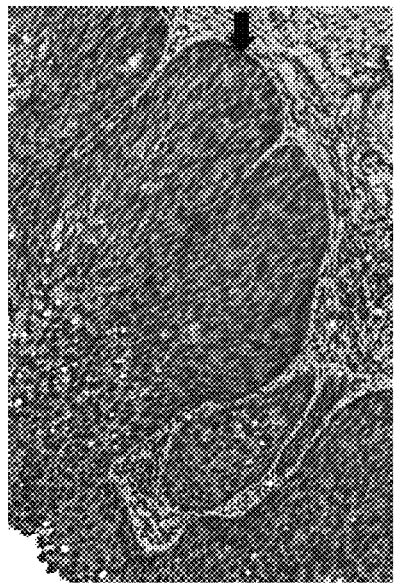
Figure 12D
Figure 12C

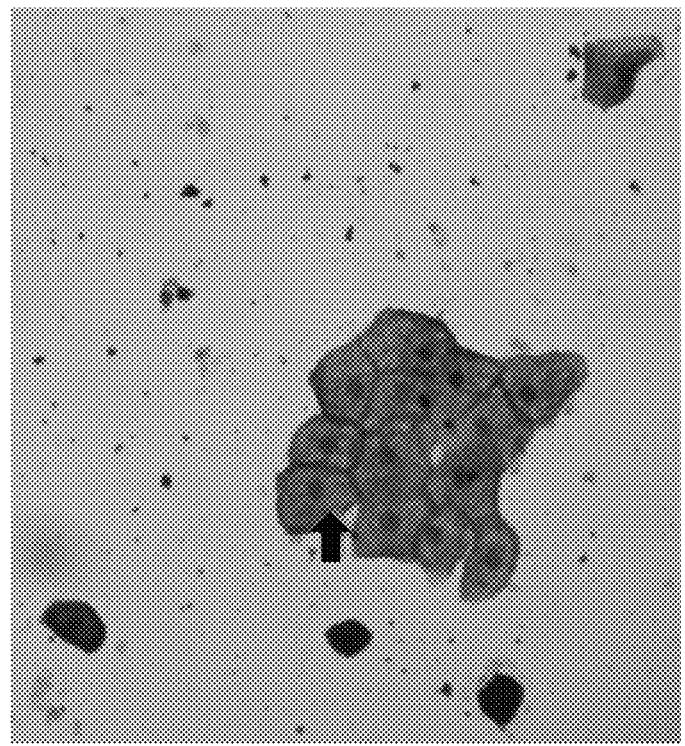
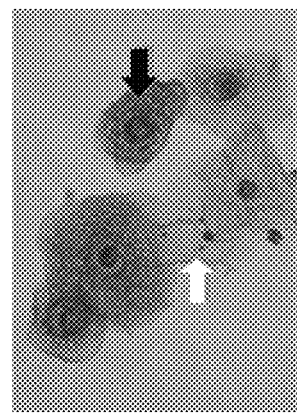
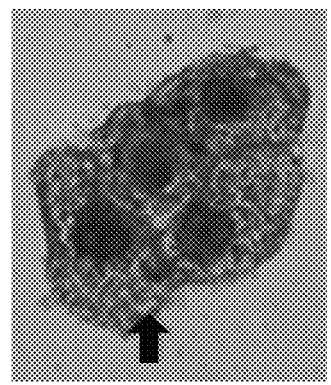
Figure 14C
Figure 14B
Figure 14A

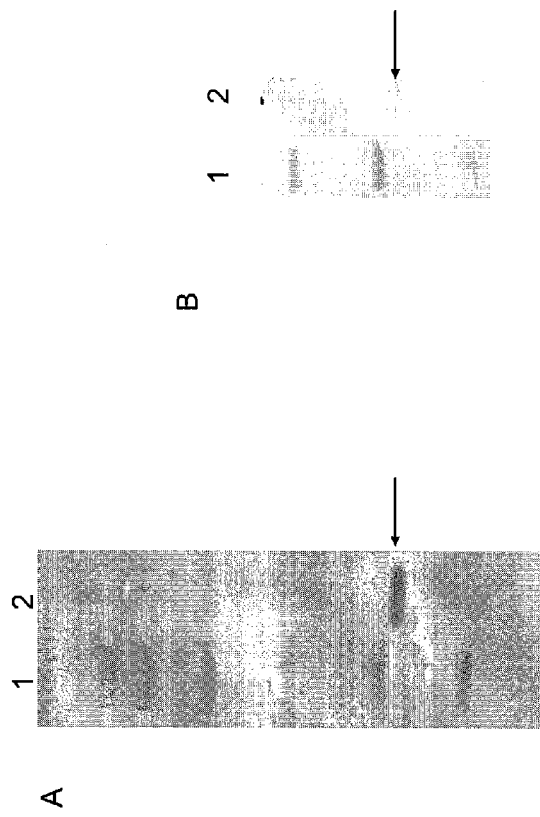
Figure 15A&B
A). SDS-PAGE and B). western blot demonstrating the full length E6 recombinant protein stained with commassie blue, then probed with anti-E6 monclonal antibody, respectively.
Lane1:Protein marker (14.4, 20.1, 31, 43, 66.2, 96.7KD upward)
Lane2:HPV16E6 recombinant protein

SEQUENCE LISTING

<160> NUMBER OF SEQ ID NOS: 27

<210> SEQ ID NO 1
<211> LENGTH: 474

```
<212> TYPE: DNA
<213> ORGANISM: pappilomavirus

<400> SEQUENCE: 1
caccaaaaga gaactgcaat gtttcaggac ccacaggagc gacccagaaa gttaccacag      60
ttatgcacag agctgcaaac aactatacat gatataatat tagaatgtgt gtactgcaag     120
caacagttac tgcgacgtga ggtatatgac tttgcttttc gggatttatg catagtatat     180
agagatggga atccatatgc tgtatgtgat aaatgtttaa agtttttattc taaaattagt    240 gagtatagac attattgtta tagtttgtat ggaacaacat tagaacagca atacaacaaa     300
ccgttgtgtg atttgttaat taggtgtatt aactgtcaaa agccactgtg tcctgaagaa     360
aagcaaagac atctggacaa aaagcaaaga ttccataata taaggggtcg gtggaccggt     420
cgatgtatgt cttgttgcag atcatcaaga acacgtagag aaacccagct gtaa           474

<210> SEQ ID NO 2
<211> LENGTH: 157
<212> TYPE: PRT
<213> ORGANISM: pappilomavirus

<400> SEQUENCE: 2

His Gln Lys Arg Thr Ala Met Phe Gln Asp Pro Gln Glu Arg Pro Arg
1               5                  10                  15

Lys Leu Pro Gln Leu Cys Thr Glu Leu Gln Thr Thr Ile His Asp Ile
            20                  25                  30

Ile Leu Glu Cys Val Tyr Cys Lys Gln Gln Leu Leu Arg Arg Glu Val
        35                  40                  45

Tyr Asp Phe Ala Phe Arg Asp Leu Cys Ile Val Tyr Arg Asp Gly Asn
    50                  55                  60

Pro Tyr Ala Val Cys Asp Lys Cys Leu Lys Phe Tyr Ser Lys Ile Ser
65                  70                  75                  80

Glu Tyr Arg His Tyr Cys Tyr Ser Leu Tyr Gly Thr Thr Leu Glu Gln
                85                  90                  95

Gln Tyr Asn Lys Pro Leu Cys Asp Leu Leu Ile Arg Cys Ile Asn Cys
            100                 105                 110

Gln Lys Pro Leu Cys Pro Glu Glu Lys Gln Arg His Leu Asp Lys Lys
        115                 120                 125

Gln Arg Phe His Asn Ile Arg Gly Arg Trp Thr Gly Arg Cys Met Ser
    130                 135                 140

Cys Cys Arg Ser Ser Arg Thr Arg Arg Glu Thr Gln Leu
145                 150                 155

<210> SEQ ID NO 3
<211> LENGTH: 34
<212> TYPE: DNA
<213> ORGANISM: pappilomavirus

<400> SEQUENCE: 3
cgcggatccc accaaaagag aactgcaatg tttc                                   34

<210> SEQ ID NO 4
<211> LENGTH: 32
<212> TYPE: DNA
<213> ORGANISM: pappilomavirus

<400> SEQUENCE: 4
cccaagcttt tacagctggg tttctctacg tg                                     32
```

<210> SEQ ID NO 5
<211> LENGTH: 510
<212> TYPE: DNA
<213> ORGANISM: pappilomavirus

<400> SEQUENCE: 5

| | | |
|---|---|---|
| atgagaggat cgcatcacca tcaccatcac ggatcccacc aaaagagaac tgcaatgttt | 60 |
| caggacccac aggagcgacc cagaaagtta ccacagttat gcacagagct gcaaacaact | 120 |
| atacatgata taatattaga atgtgtgtac tgcaagcaac agttactgcg acgtgaggta | 180 |
| tatgactttg cttttcggga tttatgcata gtatatagag atgggaatcc atatgctgta | 240 |
| tgtgataaat gtttaaagtt ttattctaaa attagtgagt atagacatta ttgttatagt | 300 |
| ttgtatggaa caacattaga acagcaatac aacaaaccgt tgtgtgattt gttaattagg | 360 |
| tgtattaact gtcaaaagcc actgtgtcct gaagaaaagc aaagacatct ggacaaaaag | 420 |
| caaagattcc ataatataag gggtcggtgg accggtcgat gtatgtcttg ttgcagatca | 480 |
| tcaagaacac gtagagaaac ccagctgtaa | 510 |

<210> SEQ ID NO 6
<211> LENGTH: 169
<212> TYPE: PRT
<213> ORGANISM: pappilomavirus

<400> SEQUENCE: 6

Met Arg Gly Ser His His His His His Gly Ser His Gln Lys Arg
1               5                   10                  15

Thr Ala Met Phe Gln Asp Pro Gln Glu Arg Pro Arg Lys Leu Pro Gln
            20                  25                  30

Leu Cys Thr Glu Leu Gln Thr Thr Ile His Asp Ile Ile Leu Glu Cys
        35                  40                  45

Val Tyr Cys Lys Gln Gln Leu Leu Arg Arg Glu Val Tyr Asp Phe Ala
    50                  55                  60

Phe Arg Asp Leu Cys Ile Val Tyr Arg Asp Gly Asn Pro Tyr Ala Val
65                  70                  75                  80

Cys Asp Lys Cys Leu Lys Phe Tyr Ser Lys Ile Ser Glu Tyr Arg His
                85                  90                  95

Tyr Cys Tyr Ser Leu Tyr Gly Thr Thr Leu Glu Gln Gln Tyr Asn Lys
            100                 105                 110

Pro Leu Cys Asp Leu Leu Ile Arg Cys Ile Asn Cys Gln Lys Pro Leu
        115                 120                 125

Cys Pro Glu Glu Lys Gln Arg His Leu Asp Lys Lys Gln Arg Phe His
    130                 135                 140

Asn Ile Arg Gly Arg Trp Thr Gly Arg Cys Met Ser Cys Cys Arg Ser
145                 150                 155                 160

Ser Arg Thr Arg Arg Glu Thr Gln Leu
                165

<210> SEQ ID NO 7
<211> LENGTH: 300
<212> TYPE: DNA
<213> ORGANISM: Papillomavirus sylvilagi

<400> SEQUENCE: 7

| | | |
|---|---|---|
| gatcccatgg agatacacct acattgcatg aatatatgtt agatttgcaa ccagagacaa | 60 |
| ctgatctcta ctgttatgag caattaaatg acagctcaga ggaggaggat gaaatagatg | 120 |

```
gtccagctgg acaagcagaa ccggacagag cccattacaa tattgtaacc ttttgttgca    180
agtgtgactc tacgcttcgg ttgtgcgtac aaagcacaca cgtagacatt cgtactttgg    240
aagacctgtt aatgggcaca ctaggaattg tgtgccccat ctgttctcag aaaccataag    300
```

<210> SEQ ID NO 8
<211> LENGTH: 97
<212> TYPE: PRT
<213> ORGANISM: pappilomavirus

<400> SEQUENCE: 8

His Gly Asp Thr Pro Thr Leu His Glu Tyr Met Leu Asp Leu Gln Pro
1               5                   10                  15

Glu Thr Thr Asp Leu Tyr Cys Tyr Glu Gln Leu Asn Asp Ser Ser Glu
            20                  25                  30

Glu Glu Asp Glu Ile Asp Gly Pro Ala Gly Gln Ala Glu Pro Asp Arg
        35                  40                  45

Ala His Tyr Asn Ile Val Thr Phe Cys Cys Lys Cys Asp Ser Thr Leu
    50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro

<210> SEQ ID NO 9
<211> LENGTH: 31
<212> TYPE: DNA
<213> ORGANISM: pappilomavirus

<400> SEQUENCE: 9

```
cgcggatccc atggagatac acctacattg c                                    31
```

<210> SEQ ID NO 10
<211> LENGTH: 32
<212> TYPE: DNA
<213> ORGANISM: pappilomavirus

<400> SEQUENCE: 10

```
ccggaattct tatggtttct gagaacagat gg                                   32
```

<210> SEQ ID NO 11
<211> LENGTH: 972
<212> TYPE: DNA
<213> ORGANISM: pappilomavirus

<400> SEQUENCE: 11

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaagtttga attgggtttg agtttcccca tcttcctta ttatattgat      180 ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca gttgtatgat cgctcttgat    480
gttgttttat acatggaccc aatgtgcctg gatgcgttcc caaaattagt ttgttttaaa    540
```

```
aaacgtattg aagctatccc acaaattgat aagtacttga aatccagcaa gtatatagca    600
tggcctttgc agggctggca agccacgttt ggtggtggcg accatcctcc aaaatcggat    660
ctggttccgc gtggatccca tggagataca cctacattgc atgaatatat gttagatttg    720
caaccagaga caactgatct ctactgttat gagcaattaa atgacagctc agaggaggag    780
gatgaaatag atggtccagc tggacaagca gaaccggaca gagcccatta caatattgta    840
accttttgtt gcaagtgtga ctctacgctt cggttgtgcg tacaaagcac acacgtagac    900
attcgtactt tggaagacct gttaatgggc acactaggaa ttgtgtgccc catctgttct    960
cagaaaccat aa                                                         972
```

<210> SEQ ID NO 12
<211> LENGTH: 323
<212> TYPE: PRT
<213> ORGANISM: pappilomavirus

<400> SEQUENCE: 12

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Gly Asp Thr Pro Thr Leu His Glu Tyr Met Leu Asp Leu
225                 230                 235                 240

Gln Pro Glu Thr Thr Asp Leu Tyr Cys Tyr Glu Gln Leu Asn Asp Ser
                245                 250                 255

Ser Glu Glu Glu Asp Glu Ile Asp Gly Pro Ala Gly Gln Ala Glu Pro
            260                 265                 270

Asp Arg Ala His Tyr Asn Ile Val Thr Phe Cys Cys Lys Cys Asp Ser
        275                 280                 285
```

Thr Leu Arg Leu Cys Val Gln Ser Thr His Val Asp Ile Arg Thr Leu
            290                 295                 300

Glu Asp Leu Leu Met Gly Thr Leu Gly Ile Val Cys Pro Ile Cys Ser
305                 310                 315                 320

Gln Lys Pro

<210> SEQ ID NO 13
<211> LENGTH: 1602
<212> TYPE: DNA
<213> ORGANISM: pappilomavirus

<400> SEQUENCE: 13

| | | | | | |
|---|---|---|---|---|---|
| tcgagatgca | ggtgactttt | atttacatcc | tagttattac | atgttacgaa | aacgacgtaa | 60 |
| acgtttacca | tatttttttt | cagatgtctc | tttggctgcc | tagtgaggcc | actgtctact | 120 |
| tgcctcctgt | cccagtatct | aaggttgtaa | gcacggatga | atatgttgca | cgcacaaaca | 180 |
| tatattatca | tgcaggaaca | tccagactac | ttgcagttgg | acatccctat | tttcctatta | 240 |
| aaaaacctaa | caataacaaa | atattagttc | ctaaagtatc | aggattacaa | tacagggtat | 300 |
| ttagaataca | tttacctgac | cccaataagt | ttggttttcc | tgacacctca | ttttataatc | 360 |
| cagatacaca | gcggctggtt | tgggcctgtg | taggtgttga | ggtaggtcgt | ggtcagccat | 420 |
| taggtgtggg | cattagtggc | catcctttat | taaataaatt | ggatgacaca | gaaaatgcta | 480 |
| gtgcttatgc | agcaaatgca | ggtgtggata | atagagaatg | tatatctatg | gattacaaac | 540 |
| aaacacaatt | gtgtttaatt | ggttgcaaac | cacctatagg | ggaacactgg | gcaaaggat | 600 |
| ccccatgtac | caatgttgca | gtaaatccag | gtgattgtcc | accattagag | ttaataaaca | 660 |
| cagttattca | ggatggtgat | atggttcata | ctggctttgg | tgctatggac | tttactacat | 720 |
| tacaggctaa | caaagtgaa | gttccactgg | atatttgtac | atctatttgc | aaatatccag | 780 |
| attatattaa | aatggtgtca | gaaccatatg | gcgacagctt | ttttttttat | ttacgaaggg | 840 |
| aacaaatgtt | tgttagacat | ttatttaata | gggctgtac | tgttggtgaa | aatgtaccag | 900 |
| acgatttata | cattaaaggc | tctgggtcta | ctgcaaattt | agccagttca | aattattttc | 960 |
| ctacacctag | tggttctatg | gttacctctg | atgcccaaat | attcaataaa | ccttattggt | 1020 |
| tacaacgagc | acagggccac | aataatggca | tttgttgggg | taaccaacta | tttgttactg | 1080 |
| ttgttgatac | tacacgcagt | acaaatatgt | cattatgtgc | tgccatatct | acttcagaaa | 1140 |
| ctacatataa | aaatactaac | tttaaggagt | acctacgaca | tgggaggaa | tatgatttac | 1200 |
| agtttatttt | tcaactgtgc | aaaataaacct | taactgcaga | cgttatgaca | tacatacatt | 1260 |
| ctatgaattc | cactattttg | gaggactgga | attttggtct | acaacctccc | ccaggaggca | 1320 |
| cactagaaga | tacttatagg | tttgtaaccc | aggcaattgc | ttgtcaaaaa | catacacctc | 1380 |
| cagcacctaa | agaagatgat | ccccttaaaa | aatacacttt | ttgggaagta | aatttaaagg | 1440 |
| aaaagttttc | tgcagaccta | gatcagtttc | ctttaggacg | caaatttttta | ctacaagcag | 1500 |
| gattgaaggc | caaaccaaaa | tttacattag | gaaaacgaaa | agctacaccc | accacctcat | 1560 |
| ctacctctac | aactgctaaa | cgcaaaaaac | gtaagctgta | aa | | 1602 |

<210> SEQ ID NO 14
<211> LENGTH: 531
<212> TYPE: PRT
<213> ORGANISM: pappilomavirus

<400> SEQUENCE: 14

Met Gln Val Thr Phe Ile Tyr Ile Leu Val Ile Thr Cys Tyr Glu Asn

-continued

```
1               5                   10                  15
Asp Val Asn Val Tyr His Ile Phe Phe Gln Met Ser Leu Trp Leu Pro
                20                  25                  30

Ser Glu Ala Thr Val Tyr Leu Pro Pro Val Pro Val Ser Lys Val Val
                35                  40                  45

Ser Thr Asp Glu Tyr Val Ala Arg Thr Asn Ile Tyr His Ala Gly
 50                      55                  60

Thr Ser Arg Leu Leu Ala Val Gly His Pro Tyr Phe Pro Ile Lys Lys
 65                  70                  75                  80

Pro Asn Asn Lys Ile Leu Val Pro Lys Val Ser Gly Leu Gln Tyr
                 85                  90                  95

Arg Val Phe Arg Ile His Leu Pro Asp Pro Asn Lys Phe Gly Phe Pro
                100                 105                 110

Asp Thr Ser Phe Tyr Asn Pro Asp Thr Gln Arg Leu Val Trp Ala Cys
                115                 120                 125

Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
                180                 185                 190

Glu His Trp Gly Lys Gly Ser Pro Cys Thr Asn Val Ala Val Asn Pro
                195                 200                 205

Gly Asp Cys Pro Pro Leu Glu Leu Ile Asn Thr Val Ile Gln Asp Gly
    210                 215                 220

Asp Met Val His Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
                260                 265                 270

Phe Phe Tyr Leu Arg Arg Glu Gln Met Phe Val Arg His Leu Phe Asn
                275                 280                 285

Arg Ala Gly Thr Val Gly Glu Asn Val Pro Asp Asp Leu Tyr Ile Lys
                290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
                340                 345                 350

Asn Gln Leu Phe Val Thr Val Val Asp Thr Thr Arg Ser Thr Asn Met
                355                 360                 365

Ser Leu Cys Ala Ala Ile Ser Thr Ser Glu Thr Thr Tyr Lys Asn Thr
    370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
                420                 425                 430
```

```
Gln Pro Pro Pro Gly Gly Thr Leu Glu Asp Thr Tyr Arg Phe Val Thr
        435                 440                 445

Gln Ala Ile Ala Cys Gln Lys His Thr Pro Ala Pro Lys Glu Asp
    450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu
                485                 490                 495

Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
            515                 520                 525

Arg Lys Leu
    530

<210> SEQ ID NO 15
<211> LENGTH: 34
<212> TYPE: DNA
<213> ORGANISM: pappilomavirus

<400> SEQUENCE: 15
ccgctcgaga tgcaggtgac ttttatttac atcc                                34

<210> SEQ ID NO 16
<211> LENGTH: 34
<212> TYPE: DNA
<213> ORGANISM: pappilomavirus

<400> SEQUENCE: 16
cccaagcttt tacagcttac gttttttgcg ttta                                34

<210> SEQ ID NO 17
<211> LENGTH: 1716
<212> TYPE: DNA
<213> ORGANISM: pappilomavirus

<400> SEQUENCE: 17
atgccgcggg gttctcatca tcatcatcat catggtatgg ctagcatgac tggtggacag     60
caaatgggtc gggatctgta cgacgatgac gataaggatc gatggggatc cgagctcgag    120
atgcaggtga cttttatttta catcctagtt attacatgtt acgaaaacga cgtaaacgtt    180
taccatattt ttttttcagat gtctctttgg ctgcctagtg aggccactgt ctacttgcct    240
cctgtcccag tatctaaggt tgtaagcacg gatgaatatg ttgcacgcac aaacatatat    300
tatcatgcag gaacatccag actacttgca gttggacatc cctattttcc tattaaaaaa    360
cctaacaata caaaatatt agttcctaaa gtatcaggat tacaatacag ggtatttaga    420
atacatttac ctgaccccaa taagtttggt tttcctgaca cctcatttta taatccagat    480
acacagcggc tggtttgggc ctgtgtaggt gttgaggtag tcgtggtca gccattaggt    540 gtgggcatta gtggccatcc tttattaaat aaattggatg acacagaaaa tgctagtgct    600
tatgcagcaa atgcaggtgt ggataataga gaatgtatat ctatggatta caaacaaaca    660
caattgtgtt taattggttg caaaccacct ataggggaac actgggcaa aggatcccca    720 tgtaccaatg ttgcagtaaa tccaggtgat tgtccaccat tagagttaat aaacacagtt    780
attcaggatg gtgatatggt tcatactggc tttggtgcta tggactttac tacattacag    840
gctaacaaaa gtgaagttcc actggatatt tgtacatcta tttgcaaata tccagattat    900
```

```
attaaaatgg tgtcagaacc atatggcgac agcttatttt tttatttacg aagggaacaa      960
atgtttgtta gacatttatt taatagggct ggtactgttg gtgaaaatgt accagacgat     1020
ttatacatta aaggctctgg gtctactgca aatttagcca gttcaaatta ttttcctaca     1080
cctagtggtt ctatggttac ctctgatgcc caaatattca ataaacctta ttggttacaa     1140
cgagcacagg gccacaataa tggcatttgt tggggtaacc aactattcgt tactgttgtt     1200
gatactacac gcagtacaaa tatgtcatta tgtgctgcca tatctacttc agaaactaca     1260
tataaaaata ctaactttaa ggagtaccta cgacatgggg aggaatatga tttacagttt     1320
atttttcaac tgtgcaaaat aaccttaact gcagacgtta tgacatacat acattctatg     1380
aattccacta ttttggagga ctggaatttt ggtctacaac ctcccccagg aggcacacta     1440
gaagatactt ataggtttgt aacccaggca attgcttgtc aaaaacatac acctccagca     1500
cctaaagaag atgatcccct taaaaaatac acttttggg aagtaaattt aaaggaaaag     1560
ttttctgcag acctagatca gtttccttta ggacgcaaat ttttactaca agcaggattg     1620
aaggccaaac caaatttac attaggaaaa cgaaaagcta cacccaccac ctcatctacc     1680
tctacaactg ctaaacgcaa aaacgtaag ctgtaa                                1716

<210> SEQ ID NO 18
<211> LENGTH: 571
<212> TYPE: PRT
<213> ORGANISM: pappilomavirus

<400> SEQUENCE: 18

Met Pro Arg Gly Ser His His His His His Gly Met Ala Ser Met
1               5                   10                  15

Thr Gly Gly Gln Gln Met Gly Arg Asp Leu Tyr Asp Asp Asp Lys
                20                  25                  30

Asp Arg Trp Gly Ser Glu Leu Glu Met Gln Val Thr Phe Ile Tyr Ile
            35                  40                  45

Leu Val Ile Thr Cys Tyr Glu Asn Asp Val Asn Val Tyr His Ile Phe
        50                  55                  60

Phe Gln Met Ser Leu Trp Leu Pro Ser Glu Ala Thr Val Tyr Leu Pro
65                  70                  75                  80

Pro Val Pro Val Ser Lys Val Val Ser Thr Asp Glu Tyr Val Ala Arg
                85                  90                  95

Thr Asn Ile Tyr Tyr His Ala Gly Thr Ser Arg Leu Leu Ala Val Gly
            100                 105                 110

His Pro Tyr Phe Pro Ile Lys Lys Pro Asn Asn Asn Lys Ile Leu Val
        115                 120                 125

Pro Lys Val Ser Gly Leu Gln Tyr Arg Val Phe Arg Ile His Leu Pro
    130                 135                 140

Asp Pro Asn Lys Phe Gly Phe Pro Asp Thr Ser Phe Tyr Asn Pro Asp
145                 150                 155                 160

Thr Gln Arg Leu Val Trp Ala Cys Val Gly Val Glu Val Gly Arg Gly
                165                 170                 175

Gln Pro Leu Gly Val Gly Ile Ser Gly His Pro Leu Leu Asn Lys Leu
            180                 185                 190

Asp Asp Thr Glu Asn Ala Ser Ala Tyr Ala Ala Asn Ala Gly Val Asp
        195                 200                 205

Asn Arg Glu Cys Ile Ser Met Asp Tyr Lys Gln Thr Gln Leu Cys Leu
    210                 215                 220
```

```
Ile Gly Cys Lys Pro Pro Ile Gly Glu His Trp Gly Lys Gly Ser Pro
225                 230                 235                 240

Cys Thr Asn Val Ala Val Asn Pro Gly Asp Cys Pro Pro Leu Glu Leu
                245                 250                 255

Ile Asn Thr Val Ile Gln Asp Gly Asp Met Val His Thr Gly Phe Gly
            260                 265                 270

Ala Met Asp Phe Thr Thr Leu Gln Ala Asn Lys Ser Glu Val Pro Leu
        275                 280                 285

Asp Ile Cys Thr Ser Ile Cys Lys Tyr Pro Asp Tyr Ile Lys Met Val
    290                 295                 300

Ser Glu Pro Tyr Gly Asp Ser Leu Phe Phe Tyr Leu Arg Arg Glu Gln
305                 310                 315                 320

Met Phe Val Arg His Leu Phe Asn Arg Ala Gly Thr Val Gly Glu Asn
                325                 330                 335

Val Pro Asp Asp Leu Tyr Ile Lys Gly Ser Gly Ser Thr Ala Asn Leu
                340                 345                 350

Ala Ser Ser Asn Tyr Phe Pro Thr Pro Ser Gly Ser Met Val Thr Ser
            355                 360                 365

Asp Ala Gln Ile Phe Asn Lys Pro Tyr Trp Leu Gln Arg Ala Gln Gly
        370                 375                 380

His Asn Asn Gly Ile Cys Trp Gly Asn Gln Leu Phe Val Thr Val Val
385                 390                 395                 400

Asp Thr Thr Arg Ser Thr Asn Met Ser Leu Cys Ala Ala Ile Ser Thr
                405                 410                 415

Ser Glu Thr Thr Tyr Lys Asn Thr Asn Phe Lys Glu Tyr Leu Arg His
                420                 425                 430

Gly Glu Glu Tyr Asp Leu Gln Phe Ile Phe Gln Leu Cys Lys Ile Thr
            435                 440                 445

Leu Thr Ala Asp Val Met Thr Tyr Ile His Ser Met Asn Ser Thr Ile
        450                 455                 460

Leu Glu Asp Trp Asn Phe Gly Leu Gln Pro Pro Pro Gly Gly Thr Leu
465                 470                 475                 480

Glu Asp Thr Tyr Arg Phe Val Thr Gln Ala Ile Ala Cys Gln Lys His
                485                 490                 495

Thr Pro Pro Ala Pro Lys Glu Asp Asp Pro Leu Lys Lys Tyr Thr Phe
                500                 505                 510

Trp Glu Val Asn Leu Lys Glu Lys Phe Ser Ala Asp Leu Asp Gln Phe
            515                 520                 525

Pro Leu Gly Arg Lys Phe Leu Leu Gln Ala Gly Leu Lys Ala Lys Pro
        530                 535                 540

Lys Phe Thr Leu Gly Lys Arg Lys Ala Thr Pro Thr Thr Ser Ser Thr
545                 550                 555                 560

Ser Thr Thr Ala Lys Arg Lys Arg Lys Leu
                565                 570

<210> SEQ ID NO 19
<211> LENGTH: 322
<212> TYPE: PRT
<213> ORGANISM: pappilomavirus

<400> SEQUENCE: 19

Met Ala Ser Met Thr Gly Gly Gln Gln Met Gly Arg Gly Ser Gln Val
1               5                   10                  15

Thr Phe Ile Tyr Ile Leu Val Ile Thr Cys Tyr Glu Asn Asp Val Asn
            20                  25                  30
```

-continued

```
Val Tyr His Ile Phe Phe Gln Met Ser Leu Trp Leu Pro Ser Glu Ala
             35                  40                  45

Thr Val Tyr Leu Pro Pro Val Pro Val Ser Lys Val Val Ser Thr Asp
 50                  55                  60

Glu Tyr Val Ala Arg Thr Asn Ile Tyr Tyr His Ala Gly Thr Ser Arg
 65                  70                  75                  80

Leu Leu Ala Val Gly His Pro Tyr Phe Pro Ile Lys Lys Pro Asn Asn
                 85                  90                  95

Asn Lys Ile Leu Val Pro Lys Val Ser Gly Leu Gln Tyr Arg Val Phe
            100                 105                 110

Arg Ile His Leu Pro Asp Pro Asn Lys Phe Gly Phe Pro Asp Thr Ser
            115                 120                 125

Phe Tyr Asn Pro Asp Thr Gln Arg Leu Val Trp Ala Cys Val Gly Val
130                 135                 140

Glu Val Gly Arg Gly Gln Pro Leu Gly Val Gly Ile Ser Gly His Pro
145                 150                 155                 160

Leu Leu Asn Lys Leu Asp Asp Thr Glu Asn Ala Ser Ala Tyr Ala Ala
                165                 170                 175

Asn Ala Gly Val Asp Asn Arg Glu Cys Ile Ser Met Asp Tyr Lys Gln
            180                 185                 190

Thr Gln Leu Cys Leu Ile Gly Cys Lys Pro Pro Ile Gly Glu His Trp
            195                 200                 205

Gly Lys Gly Ser Pro Cys Thr Asn Val Ala Val Asn Pro Gly Asp Cys
210                 215                 220

Pro Pro Leu Glu Leu Ile Asn Thr Val Ile Gln Asp Gly Asp Met Val
225                 230                 235                 240

His Thr Gly Phe Gly Ala Met Asp Phe Thr Thr Leu Gln Ala Asn Lys
                245                 250                 255

Ser Glu Val Pro Leu Asp Ile Cys Thr Ser Ile Cys Lys Tyr Pro Asp
            260                 265                 270

Tyr Ile Lys Met Val Ser Glu Pro Tyr Gly Asp Ser Leu Phe Phe Tyr
            275                 280                 285

Leu Arg Arg Glu Gln Met Phe Val Arg His Leu Phe Asn Arg Ala Gly
290                 295                 300

Thr Val Gly Glu Asn Val Pro Asp Asp Leu Val Glu His His His His
305                 310                 315                 320

His His
```

```
<210> SEQ ID NO 20
<211> LENGTH: 20
<212> TYPE: DNA
<213> ORGANISM: pappilomavirus
<220> FEATURE:
<221> NAME/KEY: misc_feature
<222> LOCATION: (3)..(3)
<223> OTHER INFORMATION: n is a, c, g, or t

<400> SEQUENCE: 20 gncargghc ayaayaatgg                                                  20

<210> SEQ ID NO 21
<211> LENGTH: 23
<212> TYPE: DNA
<213> ORGANISM: pappilomavirus

<400> SEQUENCE: 21
```

```
gtdgtatcha cmhcagtaac aaa                                          23

<210> SEQ ID NO 22
<211> LENGTH: 64
<212> TYPE: DNA
<213> ORGANISM: pappilomavirus

<400> SEQUENCE: 22
cvcaggghca yaayaatggc atttgttggg gtaaccaact atttgttact gttgtdgaya  60 cyac                                                              64

<210> SEQ ID NO 23
<211> LENGTH: 20
<212> TYPE: DNA
<213> ORGANISM: pappilomavirus

<400> SEQUENCE: 23
gttactgcga cgtgaggtat                                             20

<210> SEQ ID NO 24
<211> LENGTH: 20
<212> TYPE: DNA
<213> ORGANISM: pappilomavirus

<400> SEQUENCE: 24
gtttcaggac ccacaggagc                                             20

<210> SEQ ID NO 25
<211> LENGTH: 20
<212> TYPE: DNA
<213> ORGANISM: pappilomavirus

<400> SEQUENCE: 25
caacggtttg ttgtattgct                                             20

<210> SEQ ID NO 26
<211> LENGTH: 181
<212> TYPE: DNA
<213> ORGANISM: pappilomavirus

<400> SEQUENCE: 26
gttactgcga cgtgaggtat atgactttgc ttttcgggat ttatgcatag tatatagaga  60
tgggaatcca tatgctgtat gtgataaatg tttaaagttt tattctaaaa ttagtgagta 120
tagacattat tgttatagtt tgtatggaac aacattagaa cagcaataca acaaaccgtt 180
g                                                                181

<210> SEQ ID NO 27
<211> LENGTH: 286
<212> TYPE: DNA
<213> ORGANISM: pappilomavirus

<400> SEQUENCE: 27
gtttcaggac ccacaggagc gacccagaaa gttaccacag ttatgcacag agctgcaaac  60
aactatacat gatataatat tagaatgtgt gtactgcaag caacagttac tgcgacgtga 120
ggtatatgac tttgcttttc gggatttatg catagtatat agagatggga atccatatgc 180
tgtatgtgat aaatgtttaa agttttattc taaaattagt gagtatagac attattgtta 240
tagtttgtat ggaacaacat tagaacagca atacaacaaa ccgttg               286
```

IDENTIFICATION OF HIGH GRADE OR ≥ CIN2 FOR EARLY STAGES AND LATE STAGES DETECTION, SCREENING, AND DIAGNOSIS OF HUMAN PAPILLOMAVIRUS (HPV) AND HPV-ASSOCIATED CANCERS

CROSS-REFERENCE TO RELATED APPLICATIONS

This application claims the benefit of U.S. Prov. Patent App. Ser. No. 61/215,589, filed on May 7, 2009, entitled "Novel Antibodies and Assays Useful for Early Stages and Late Stages Detection, Screening, and Diagnosis of Human Papillomavirus (HPV) and HPV-Associated Cancers".

This application is cross related to U.S. patent application Ser. No. 11/559,366, filed on Nov. 13, 2006, now U.S. Pat. No. 7,732,166, entitled "Detection Method for Human Papillomavirus (HPV) and Its Application in Cervical Cancer", U.S. patent application Ser. No. 12/082,740, filed on Apr. 14, 2008, now U.S. Pat. No. 7,972,776, entitled "Protein Chips for HPV Detection", U.S. App. Ser. No. 61/131,991, filed on Jun. 13, 2008, entitled "Antibodies and Assays for HPV Detection", and U.S. App. Ser. No. 61/192,912, filed on Sep. 22, 2008, entitled "Novel Monoclonal Antibodies against HPV Proteins Useful for Early State and Late Stage Detection, Screening, and Diagnosis of HPV Related Cervical Cancer", U.S. application Ser. No. 12/456,053, filed on Jun. 10, 2009, entitled "Novel Monoclonal Antibodies against HPV Proteins", U.S. application Ser. No. 12/456,054, filed on Jun. 10, 2009, entitled "in situ Detection of Early Stages and Late Stages HPV Infection", U.S. application Ser. No. 12/456,055, filed on Jun. 10, 2009, entitled "in situ Detection of Early Stages and Late Stages HPV Infection", U.S. application Ser. No. 12/456,076, filed on Jun. 10, 2009, now U.S. Pat. No. 8,278,056, entitled "Detection of Early Stages and Late Stages HPV Infection", U.S. App. Ser. No. 61/199,013, filed on Nov. 12, 2008, entitled "Detection, Screening and Diagnosis of HPV Associated Cancers", and U.S. application Ser. No. 12/590,747, filed on Nov. 12, 2009, entitled "Detection, Screening and Diagnosis of HPV Associated Cancers". The contents of the above cross-related applications are hereby incorporated by reference in their entireties.

BACKGROUND OF THE INVENTION

Cervical cancer is the second most common cause of cancer deaths in women worldwide, with about a half million new cases and about a quarter of a million deaths every year. In the US, the cervical cancer mortality rate has decreased substantially due to the success of cervical cancer screening programs, which detect precancers and lead to intervention and treatment of precancers before they develop into cancer. The current paradigm for cervical cancer screening is based on the Pap test, which is a cytologically based test of cells scraped from the cervix and examined microscopically either by a human or by a machine to detect changes indicating dysplastic cell growth. The test is subjective with significant inter-observer variability, and is limited by low sensitivity and high false positive results. Reports of false-negative rates in cervical cytology have varied widely, from as low as 1.6% to almost 28%. About 4 million abnormal Pap tests are diagnosed in the United States each year as atypical squamous cells of undetermined significance (ASC-US), atypical squamous cells cannot exclude high-grade squamous intraepithelial lesion (ASC-H), low-grade squamous intraepithelial lesion (LSIL), or atypical glandular cells (AGC).

Under current practice guideline, these cases are referred for colposcopy to further identify the subset of patients that will have clinically significant high-grade lesions (CIN2/3) or endocervical neoplasia on cervical biopsy. It was reported that patients with a cytologic diagnosis of ASC-US (over 2 million cases annually in the US) have only 5% to 17% chance of underlying CIN2/3 on cervical biopsy, and in LSIL (about 1.6 million cases in the US annually), CIN2/3 was found in up to 25%. These data suggest that about 3 million of cases with ASC-US or LSIL on Pap, colposcopy is unnecessary. Although colposcopic biopsy has historically been considered the gold standard, recent reports indicate that cervical biopsies may miss 33% to 50% of high-grade disease because of sampling or diagnostic errors. As a result, it may be difficult to differentiate between false positive cervical cytology results versus false-negative biopsy results. Therefore, there is strong need for a test to identify high-grade dysplasia to triage the patient who can benefit most from intervention.

Although most low grade cervical dysplasias spontaneously regress without ever leading cervical cancer, dysplasia can serve as an indication that increased vigilance is needed. CIN1 is the most common and most benign form of cervical intraepithelial neoplasia and usually resolves spontaneously within two years. Because of this, LSIL results can be managed with a simple "watch and wait" philosophy. However, because there is a 12-16% chance of progression to more severe dysplasia, the physician may want to follow the results more aggressively by performing a colposcopy with biopsy. If the dysplasia progresses, treatment may be necessary. Therefore, what is needed is a method to detect HPV oncoproteins in situ. It would be particularly helpful in ASC-US or LSIL, or CIN1 patients to detect high-grade dysplasia cells and to identify those underlying CIN2 or above who may benefit immediate intervention, and avoid anxiety for "wait and see".

Infection by Human Papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 millions of sexually active men and women worldwide are currently infected. Approximately 1% of the population has genital warts and 4% of women have cervical precancerous lesions, such as low grade of squamous intraepithelial lesion (LSIL) or high grade of squamous intraepithelial lesion (HSIL) or atypical squamous cells of undetermined significance (ASC-US).

The presence of these lesions, preferentially observed in women aged 35-40 yrs, are at high risk of progression toward invasive cervical cancer. It is general thought that persistent infection of human Papillomavirus (HPV) is essential for developing precancerous epithelial lesions. Infection of high-risk types HPV for women with LSIL may or may not progress to HSIL. In fact, remission occurs in majority of LSIL human subjects while some progress to HSIL. Although 99.7% of cervical cancers are HPV positive, integration of viral genome into the host genome is required to facilitate the necessary genes to express for developing into HSIL or cancer. In fact, only one in every 10 women with persistent HPV infection may develop into higher grades of CIN lesions, such as cervical intraepithelial neoplasia (CIN) grade 2 and grade 3 (CIN2, and CIN3, respectively), and a portion of these epithelial lesion cases may ultimately progress into cervical cancer.

Disease stages caused by HPV infection include an early stage HPV infection, a late stage HPV infection, Atypical squamous cells of undetermined significance (ASC-US), Atypical squamous cells, cannot exclude HSIL (ASC-H), Atypical glandular cells (AGC), low grade of squamous intraepithelial lesion (LSIL), high grade of squamous intraepithelial lesion (HSIL), cervical intraneoplasm CIN1, CIN2, CIN3 representing a mild, moderate, or severe cell dysplasia respectively, invasive cervical cancer, adenocarcinoma, or squamous cell carcinoma (SCC).

In the past, screening for cervical cancer is based on conventional cytology by Papanicolaou (Pap) smear and suspicious smears are followed up with colposcopy, and/or histological biopsy. The use of cytological screening leads to a remarkable reduction in the mortality of cervical cancer. However, due to subjective test criteria, drawbacks of Pap smear tests include difficulty in obtaining samples, poor inter- and intra-observer agreement, a high rate of false negatives (up to 20%) and false positive, the requirements for specialized laboratories staffed with highly trained personnel, and inability to identify a large proportion of HPV-infected persons. More reproducible assays are needed to improve the current screening method to avoid unnecessary medical intervention and psychological distress for the affected women. The current cervical cytology screening has sensitivity ranged from 30% to 87% and specificity ranged from 86% to 100%.

Detecting HPV infection by nucleic acid methods, has been developed, but not ideal, due to not only its high cost, assay operation procedures, the requirements for facility, equipment, and highly trained personnel, but also its very low positive predictive value to CIN. In addition, DNA testing could not differentiate the diagnosis of LSIL from HSIL, nor CIN lesions from non-transforming latent or remissive viral infection. Assay for the detection of E6/E7 mRNA suggested equivalent sensitivity to HPV DNA testing with higher positive predictive value. However, there are limited reports showing direct detection of E6/E7 oncoproteins in situ. What is needed is a low cost, simple, sensitive and specific assay that can be performed on routine practice of a clinical lab or doctor office and capable of detecting early stage of epithelial lesions, distinguish LSIL from HSIL, or predicting the risk of progression into cervical cancer.

Known protocols for the production of monoclonal antibodies to HPV are generally unsuitable for the production of anti-HPV monoclonal antibodies and cannot be used in immunocytochemical diagnostic tests for screening general human population. This is because antibodies produced by these protocols will not necessarily react with the naturally occurring HPV protein in infected human cells. In addition, the epitopes recognized by prior antibodies will not necessarily be those epitopes which are resistant to the standard procedures involved in the sampling, fixing and storing of clinical specimens. Other attempts to detect the presence of HPV related antibodies or viral proteins in a human subject by ELISA (enzyme linked immunosorbent assays) generally lead to extremely low assay sensitivity and thus can not be developed into a commercially suitable diagnostic test. Most of these ELISA assays target a single viral protein or short peptide fragments, which are not able to interact well or bind strongly and specifically to antibodies from the human subject. The assay specificity and sensitivity are so low that even using samples from patients confirmed with HPV associated invasive cervical cancer, only 53% of the patient samples were found positive for HPV infection. Given the testing populations come from general screening, with or without low grade, or precancerous, the sensitivity of the assay will be too low to apply for clinical practice. Thus, there is no successful ELISA assay available as a diagnostic tool for clinical samples.

There are only about 15 types out of more than 100 types of HPV infection considered to become high-risk of developing into CIN or cervical cancer. Also, around 70% of cervical cancer cases and 50% of CIN2 and CIN 3 cases are attributed to high risk HPV type-16 and HPV type-18 infections. However, some progressive cervical cancer cases are related to infection by low risk HPV types, while infection of some HPV types will never progress into cervical cancer. It becomes important to identify those HPV infections with particular oncogenic proteins expression rather than just identify high risk type(s) of HPV infection. Thus, there is a need for detecting HPV oncoproteins as cervical cancer biomarkers to better identify the risk for developing HSIL, or precancerous, or cervical cancer.

Developing appropriate assays, such as HPV immunoassays, is needed for detection of such HPV oncoproteins or biomarkers for cervical cancer. The presence of E6/E7 oncoproteins in CIN 2 and CIN3 lesions could be evidence to indicate high risk of progression. However, there is limited antibody available for the detection of E6/E7 oncoprotein in situ. Therefore, there is a need to develop antibodies and immunological assays for detecting HPV oncoproteins as cervical cancer biomarkers to identify HSIL or ≥CIN2 (CIN2 and above), or precancerous to screen for invasive cervical cancer and/or the risk for malignant transformation into cervical cancer and other HPV associated cancers.

SUMMARY OF THE INVENTION

Various embodiments provide various immunoassays for in situ detection of HPV proteins and cellular proteins using various monoclonal antibodies against recombinant HPV proteins and antibodies against cellular proteins. Various embodiments also provides HPV immunocytochemistry (ICC) assay, HPV immunohistochemistry (IHC) assay, to detect the presence of HPV proteins and cellular proteins affected by HPV infection in cervical cells or cervical tissues, and other HPV associated cancers including but not limited to, bladder cancer, head and neck cancers, lung cancer, etc.

In some embodiments, a method of screening a human subject of high grade dysplasia cells is conducted by one or more immunohistological assay to detect in situ one or more Papillomavirus proteins from one or more Papillomavirus types and to detect in situ one or more cellular proteins affected by HPV infection from one or more Papillomavirus types present in a biological sample on a slide containing tissues including but not limited to cervical cancer, bladder cancer, lung cancer, head and neck cancer, etc.

In some embodiments, a method of screening a human subject of high grade dysplasia cells is conducted by an immunocytological assay to detect in situ one or more Papillomavirus proteins from one or more Papillomavirus types and to detect in situ one or more cellular proteins affected by HPV infection from one or more Papillomavirus types present in a biological sample on a slide containing a thin layer of human cells, using one or more antibodies to stain the thin layer of human cells.

In some embodiments an HPV E6E7 ICC assay is provided.

In some embodiments the ICC assay is used along with the Pap smear test.

In some embodiments, the one or more antibodies are generated against one or more purified recombinant Papillomavirus proteins, wherein at least one antibody is capable of recognizing a Papillomavirus oncoprotein. In some embodiments, the one or more antibodies are tagged with an agent, and one or more human cells from a biological sample of the human subject are prepared into a liquid-based solution, such that the binding of the one or more antibodies with the one or more Papillomavirus proteins from one or more Papillomavirus types present in the one or more human cells of the biological sample can be detected by the presence of the agent reacting with the tagged one or more antibodies. In some embodiments, the agent includes a colorimetric agent, a fluorescent chromogen, and other agents for later separation and identification of the one or more human cells in one or more flow cytometry assays.

In some embodiments, a kit for performing an immunohistochemistry assay is provided. The kit may include an pre-antibody blocking solution, post-antibody blocking solution, an anti-HPV antibody as the primary antibody, an anti-mouse or anti-rabbit immunoglobulins conjugated with HRP or biotin, or other agents as secondary antibody, a solution containing appropriate agents used as substrate for the secondary antibody to be detected.

In some embodiments, a kit for performing an immunocytochemistry assay is provided. The kit may include an pre-antibody blocking solution, post-antibody blocking solution, an anti-HPV antibody as the primary antibody, an anti-mouse or anti-rabbit immunoglobulins conjugated with HRP or biotin, or other agents as secondary antibody, a solution containing appropriate agents used as substrate for the secondary antibody to be detected.

One embodiment provides a method for determining a disease stage of papilloma virus infection in a human subject comprising: obtaining a sample from said human subject, said sample consisting of a tissue sample comprising proteins or a cell sample comprising proteins; contacting said sample with a first one or more antibodies that specifically bind to one or more recombinant HPV proteins, said plurality of recombinant HPV proteins selected from the group consisting of a recombinant papillomavirus E6 gene product, a recombinant papillomavirus E7 gene product, a recombinant papillomavirus L1 gene product, a recombinant papillomavirus truncated L1 gene product, and a recombinant papillomavirus L2 gene product, wherein said contacting takes place under conditions that promote specific binding of said plurality of antibodies; determining a presence, absence, or amount of a first one or more proteins in said sample that specifically binds to one or more of said first one or more antibodies based at least in part on a measure of specific binding of one or more of said first one or more antibodies to said contacted sample; and determining said disease stage of papilloma virus infection in said human subject based on said determined presence, absence, or amount of said one or more proteins in said sample.

In one embodiment, the first one or more proteins comprise one or more proteins selected from the group consisting of a papillomavirus E6 gene product, a papillomavirus E7 gene product, a papillomavirus L1 gene product, a papillomavirus truncated L1 gene product, and a papillomavirus L2 gene product.

In one embodiment, the first one or more proteins comprise one or more proteins selected from the group consisting of a papillomavirus E6 gene product and a papillomavirus E7 gene product.

In one embodiment, the method further comprises contacting said sample with a second one or more antibodies; determining a presence, absence or amount of a second one or more proteins selected from the group consisting of $p16^{INK4a}$ (p16), CDK6, Ki-67 (MIB-1), MYC protein, cyclin-A, cyclin-B, cyclin-E, telomerase-TERC, MCM2, TOP2A, heat shock protein 40 ($HSP_{40}$), heat shock protein 60 ($HSP_{60}$), heat shock protein 70 ($HSP_{70}$), CA9/MN, laminin5, bm-3a, CDK N2, topoisomerase 2A, microsome maintenance protein-2, microsome maintenance protein-4, microsome maintenance protein-5, survivin, VEGF, p27 (kip1), and p21 (waf) in said sample based on a measure of specific binding of one or more of said second plurality of the antibodies to said contacted sample; and screening said human subject for papillomavirus infection is further based on said determined presence, absence, or amount of said second one or more proteins.

In one embodiment, the one or more proteins comprises $p16^{INK4a}$.

In one embodiment, the sample is in situ.

In one embodiment, the sample comprises a tissue sample, and said determining comprises a immunohistochemistry assay.

In one embodiment, the sample comprises a cell sample, and said determining comprises an immunocytochemistry assay.

In one embodiment, the determining said disease stage comprises determining the presence or absence of HSIL.

In one embodiment, the determining said disease stage comprises determining the presence or absence of late stage HPV infection.

In one embodiment, the determining said disease stage comprises determining the presence or absence of high grade dysplasia.

In one embodiment, the disease stage is ≥CIN2 or <CIN2.

In one embodiment, the disease stage is ≥CIN2 is CIN2/3.

In one embodiment, the disease stage is HSIL.

In one embodiment, the disease stage is late stage HPV infection.

In one embodiment, the disease stage is high grade dysplasia.

In one embodiment, the recombinant HPV proteins are made by a process comprising the steps of: providing a recombinant construct encoding a fusion protein comprising said papillomavirus gene product and an affinity tag selected from the group consisting of a HIS tag, a GST tag, and an MBP tag; expressing said recombinant construct in a host cell; incubating an extract prepared from said host cell with an affinity resin under conditions in which said affinity resin specifically binds said affinity tag; and eluting said recombinant HPV protein from said affinity resin, wherein said expressing of said recombinant construct in said host cell results in a level of protein expression such that said eluting produces a composition comprising said recombinant HPV protein at a concentration of from 1 mg/L to 10 mg/L, wherein said recombinant HPV protein is present in said composition at a purity of at least 90% as determined by SDS PAGE, and wherein said recombinant HPV protein is present in said composition in a substantially soluble, monomeric form, as determined by size-exclusion chromatography.

In one embodiment, the papillomavirus comprises one or more viruses selected from the group consisting of HPV-6, HPV-11, HPV-16, HPV-18, HPV-31, HPV-33, HPV-35, HPV-39, HPV-42, HPV-43, HPV-44, HPV-45, HPV-51, HPV-52, HPV-53, HPV-54, HPV-55, HPV-56, HPV-58, HPV-59, and HPV-66.

In one embodiment, the papillomavirus comprises one or more viruses selected from the group consisting of HPV-16 and HPV-18.

In one embodiment, the recombinant papillomavirus E6 gene product is a recombinant HPV-16 E6 gene product or a recombinant HPB-18 E6 gene product.

In one embodiment, the recombinant papillomavirus E7 gene product is a recombinant HPV-16 E7 gene product or a recombinant HPV-18 E7 gene product.

In one embodiment, the cell sample comprises normal cells, ASC-US cells, ASC-H cells, LSIL cells, HSIL cells, ADC cells, or SCC cells.

In one embodiment, the tissue sample is benign, CIN1, CIN2, CIN3, SCC, or ADC.

In one embodiment, the method further comprises obtaining a second sample from said human subject, said sample comprising a cell sample and performing a cytological Papanicolaou smear assay on said sample.

In one embodiment, the method further comprises obtaining a second sample from said human subject, said sample comprising a nucleic acid and performing a DNA test for human papillomavirus on said sample.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of some embodiments and are therefore not to be considered limiting of its scope, for the intention may admit to other equally effective embodiments.

FIG. 12A shows the representative staining image of the dysplasia cells of CIN2 tissues using an anti-E6 monolonal antibody in an immunohistocytostaining (IHC) assay.

FIG. 12B shows the representative staining image of the adjacent normal epithelium from the dysplasia tissue of the CIN2 sample of FIG. 12A.

FIG. 12C shows the representative staining image of the dysplasia epithelium of a CIN3 sample stained by the same anti-E6 monolonal antibody as used in FIG. 12A in an IHC assay, demonstrating specific IHC staining in the nuclear and cytoplasm of dysplasia cells by the anti-E6 monoclonal antibody.

FIG. 12D shows the representative staining image of the dysplasia epithelium of another CIN3 sample stained by the same anti-E6 monolonal antibody as used in FIG. 12A in an IHC assay.

FIG. 14A shows the representative staining image of cervical cells from a CIN2 cervical scrape sample prepared by thin prep and stained by a mouse monoclonal anti-HPV E7 antibody in an immunocytochemistry (ICC) assay.

FIG. 14B shows the representative staining image of cervical cells from a CIN3 cervical scrape sample prepared by thin prep and stained by a mouse monoclonal anti-E6 antibody in an ICC assay.

FIG. 14C shows the representative image of cervical cells from an adenocarcinoma (ADC) cervical scrape sample prepared by thin prep and stained by the same anti-E6 antibody shown in FIG. 14B in an ICC assay.

FIG. 15A demonstrates one embodiment of an exemplary purified recombinant protein encoded by an E6 early gene as visualized by SDS-PAGE by staining with commassie blue.

FIG. 15B demonstrates detection of a purified recombinant protein, HPV-16 E6 recombinant protein, by Western blot analyses according to one or more embodiments of the invention.

DETAILED DESCRIPTION

Figures 1A, 1B:
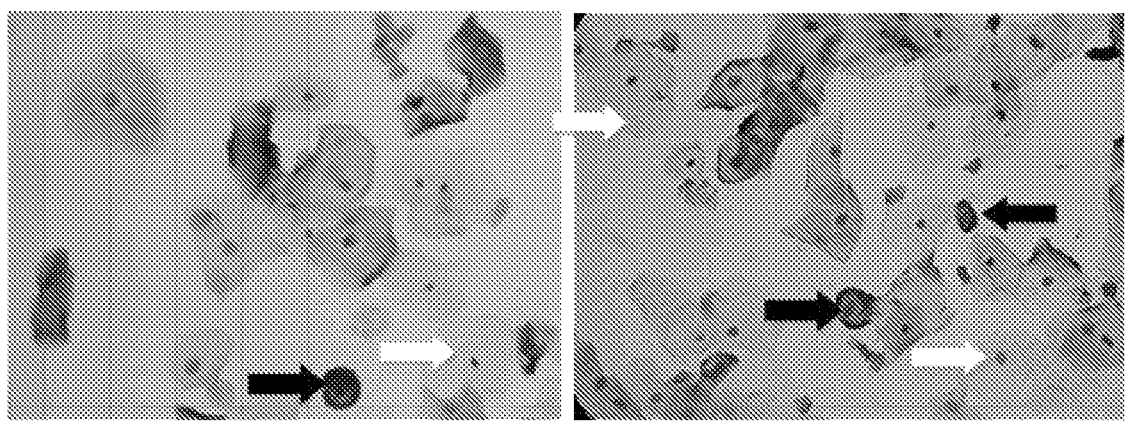
FIG. 1A shows the results of ICC staining of a clinical sample diagnosed as CIN2 in a liquid based solution using an anti-HPV E7 mouse monoclonal antibody.
FIG. 1B shows the results of ICC staining of another clinical sample diagnosed as CIN2 in a liquid based solution using an anti-HPV E6 mouse monoclonal antibody.

Various embodiments provide various immunoassays and monoclonal antibodies against HPV oncoproteins as biomarkers such that high-grade dysplasia cells infected by high risk and low risk HPV types can be detected by one or more antibodies. Various embodiments provide HPV immunohistochemistry (IHC) assay and HPV immunocytochemistry (ICC) assay detecting the presence of HPV oncoproteins to identify high-grade dysplasia cells from high-grade or pre-cancerous lesion in tissues or cervical cells in situ. Various embodiments also provide methods of using combined HPV viral marker and cellular markers for IHC, or ICC assay to obtain higher sensitivity compared to methods of using single HPV viral marker or single cellular marker for IHC or ICC assay for the detection of the high-grade dysplasia cells in situ.

In some embodiments, a method of screening human subjects for Papillomavirus infection is conducted by an immunocytological assay on the slide containing a thin layer of human cells to detect in situ one or more Papillomavirus proteins from one or more Papillomavirus types present in the biological sample on the slide. The thin layer is a monolayer of cervical cells.

To stain the thin layer of human cells using one or more antibodies generated against one or more purified recombinant Papillomavirus proteins, or generated against one or more cellular proteins affected by HPV infection, at least one antibody is capable of recognizing a Papillomavirus oncoprotein. The Papillomavirus oncoproteins include but are not limited to, HPV-16 E6 protein, HPV-16 E7 protein, HPV-18 E6 protein, HPV-18 E7 protein, and combinations thereof. The cellular markers include, but are not limited to, $p16^{INK4a}$ (p16), pRB, p53, E2F, E2F activated cell cycle protein, cyclin dependent kinase, CDK4, CDK6, Ki-67 (MIB-1), MYC protein, cyclin-A, cyclin-B, cyclin-E, telomerase-TERC, MCM2, TOP2A, heat shock protein 40 ($HSP_{40}$), heat shock protein 60 ($HSP_{60}$), heat shock protein 70 ($HSP_{70}$), CA9/MN, laminin5, brn-3a, CDK N2, topoisomerase 2A, microsome maintenance protein-2, microsome maintenance protein-4, microsome maintenance protein-5, survivin, VEGF, p27 (kip1), and p21 (waf).

In some embodiments, one or more immunohistochemical assays on the slide containing the thin section of the clinical tissue sample was conducted to stain the human cells using one or more antibodies generated against one or more purified recombinant Papillomavirus proteins, or generated against one or more cellular proteins affected by HPV infection, at least one antibody is capable of recognizing a Papillomavirus oncoprotein to detect in situ one or more proteins from one or more Papillomavirus types present in the thin section of the clinical tissue sample on the slide. The Papillomavirus oncoprotein includes but not limited to, HPV-16 E6 protein, HPV-16 E7 protein, HPV-18 E6 protein, HPV-18 E7 protein, and combinations thereof. The cellular markers include but not limited to, $p16^{INK4a}$, pRB, p53, E2F, E2F activated cell cycle protein, cyclin dependent kinase, CDK4, CDK6, Ki-67 (MIB-1), MYC protein, cyclin-A, cyclin-B, cyclin-E, telomerase-TERC, MCM2, TOP2A, heat shock protein 40 ($HSP_{40}$), heat shock protein 60 ($HSP_{60}$), heat shock protein 70 ($HSP_{70}$), CA9/MN, laminin5, brn-3a, CDK N2, topoisomerase 2A, microsome maintenance protein-2, microsome maintenance protein-4, microsome maintenance protein-5, survivin, VEGF, p27 (kip1), and p21 (waf).

In some embodiments, cytological Papanicolaou smear assay on the clinical samples was also performed to compare the results of the cytological Papanicolaou smear test with the results of the one or more immunohistological assays. Nucleic acid hybridization assay on the clinical samples was also performed to detect the presence of a Papillomavirus genome in the clinical samples from the human subject Various embodiments generally relate to various methods, detection assays, kits, polyclonal and monoclonal antibodies, polypeptides, recombinant proteins, and nucleic acids useful for detecting HPV infection, including general HPV infection as well as infection by various HPV genotypes, high risk HPVs and low risk HPVs. Various novel monoclonal antibodies against HPV proteins, useful as biomarkers and useful tools for detecting HPV viral proteins, HPV oncoproteins, early screening of cervical cancer, and diagnosing disease stages ≥CIN2 are provided. The tools described herein can also be used in early clinical screening for HPV infection and general diagnosis for cervical cancer and other HPV related cancers, In some embodiments, the one or more purified recombinant Papillomavirus proteins include Papillomavirus E6 protein, Papillomavirus E7 protein, Papillomavirus L1 protein and combinations thereof. The recombinant Papillomavirus proteins include, but not limited to recombinant HPV-16 E6 proteins, recombinant HPV-16 E7 proteins, recombinant HPV-18 E6 proteins, recombinant HPV-18 E7 proteins, and HPV-16 L1 proteins, recombinant HPV-18 L1 proteins combinations thereof.

Some embodiments provide various monoclonal antibodies against HPV viral proteins such that infection by high risk and low risk HPV types can be detected by a single monoclonal antibody. Some embodiments also provide HPV non-type specific monoclonal antibodies for detecting one or more HPV types. The one or more Papillomavirus types includes high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof.

Definitions of various terms used in some embodiments:

NILM: Negative for Intraepithelial Lesion of Malignancy. NILM is used when there is no cellular evidence of neoplasia; this may include organisms and/or other non-neoplastic findings such as reactive/reparative changes.

ASC-US: Atypical Squamous Cells of Undetermined Significance. Cells are usually the size of intermediate or superficial squamous cells and have nuclear changes that are suggestive but not diagnostic of LSIL or SIL not otherwise specified.

ASC-H: Atypical Squamous Cells cannot exclude HSIL. Cells are usually the size of metaplastic cells and may be seen singly or in clusters; they are suggestive but not diagnostic of HSIL.

LSIL: Low grade Squamous Intraepithelial Lesion, encompassing: HPV cytopathic effect/mild dysplasia/CIN 1.

HSIL: High grade Squamous Intraepithelial lesion, encompassing: moderate dysplasia/CIN 2 and severe dysplasia/CIS/CIN 3 and HSIL with features suspicious for invasion.

Squamous cell carcinoma (SCC): Cancer of the cervix, locally invasive into neighboring tissues, blood vessels, lymph channels and lymph nodes. In its advanced stages it can be difficult to treat and may prove fatal. Depending on the stage or degree of invasion, invasive cancer of the cervix may be treated with local excision, hysterectomy, radical hysterectomy, radiation, and chemotherapy.

Adenocarcinoma: While most cancer of the cervix comes from the squamous cells making up the exterior skin, there is an occasional cancer that arises from the mucous-producing cells which line the endocervical canal leading up into the uterus. This glandular-type is called "adenocarcinoma" as opposed to "squamous cell carcinoma." Adenocarcinoma can be difficult to detect. Unlike squamous cell cancer: Adenocarcinoma precursors, when present, can be difficult to identify on Pap smears. The slow progression of squamous cell dysplasia into squamous cell cancer of the cervix is not as uniform in adenocarcinoma.

In the United States, most Pap results are normal, however, about 4-5 million abnormal Pap test results are found each year. Most abnormal results are mildly abnormal (ASC-US, typically 2-5% of Pap results) or LSIL (about 2% of results), indicating HPV infection. Although most low grade cervical dysplasias spontaneously regress without ever leading cervical cancer, dysplasia can serve as an indication that increased vigilance is needed. CIN1 is the most common and most benign form of cervical intraepithelial neoplasia and usually resolves spontaneously within two years. Because of this, LSIL results can be managed with a simple "watch and wait" philosophy. However, because there is a 12-16% chance of progression to more severe dysplasia, the physician may want to follow the results more aggressively by performing a colposcopy with biopsy. If the dysplasia progresses, treatment may be necessary. Therefore, it is useful to provide HPV E6E7 ICC assay along with the Pap smear test for detecting HPV oncoproteins in situ, particularly helpful in ASC-US or LSIL, or CIN1 patients to detect high-grade dysplasia cells and to identify those underlying CIN2 or above who may benefit immediate intervention, and avoid anxiety for "wait and see".

High grade squamous intraepithelial lesion or HSIL or HGSIL indicates moderate or severe cervical intraepithelial neoplasia or carcinoma in situ. It is usually diagnosed following a Pap test. In some cases these lesions can lead to invasive cervical cancer, if not followed appropriately. HGSIL does not mean that cancer is present. Of all women with HGSIL results, 2% or less have invasive cervical cancer at that time, however about 20% would progress to having invasive cervical cancer without treatment. To combat this progression, HGSIL is usually followed by an immediate colposcopy with biopsy to sample or remove the dysplastic tissue. This tissue is sent for pathology testing to assign a histological classification that is more definitive than a Pap smear result. HGSIL generally corresponds to the histological classification of CIN2 or CIN3. Therefore, it is helpful to provide HPV E6E7 IHC assay along with HE (Hematoxylin and eosin stain) or HPV E6E7 ICC assay along with the Pap test for detecting HPV E6E7 oncoproteins in situ, particularly helpful in identifying CIN2/CIN3 patients.

In some embodiments, the binding of the one or more antibodies with the one or more proteins from one or more Papillomavirus types present in the biological samples were examined under a microscope, detecting the presence of an agent reacting with the tagged one or more antibodies, wherein the agent includes a colorimetric agent, a fluorescent chromogen, and combinations thereof. The biological sample includes of cervical cells, cervical tissues, cervical swabs, body fluids, serum, blood, tumors, cell cultures, biopsies, and combination thereof. The biological sample can be obtained from a group of people as referral due to abnormal Pap test results or as general population for routine screening of cervical cancer.

Illustrative Example 1

Some embodiments are directed to immunoassay which comprises the detection of HPV proteins and cellular proteins in exfoliated cervical cells. As an example, the results of ICC assay demonstrate that HPV E6 and HPV E7 proteins can be detected in situ on single cells fixed on a slide using a mouse monoclonal anti-HPV E6 or anti-HPV E7 antibody. The in situ presence of HPV E6 or HPV E7 oncoproteins can be detected from various stages of cervical scrape samples in various liquid based solutions. The same cervical scrape samples were also processed by standard Papanicolau staining to compare the ICC staining results with the Pap smear results.

For example, HPV E6 proteins are detected in the cervical scrape normal, ASC-US, ASC-H, CIN1, CIN2/3 samples with increasing positivity rate, respectively. There is about 92% positive rate for samples diagnosed with Pap smear HSIL (CIN2/3), while only 15% of samples diagnosed with Pap smear normal stained positively by ICC using the same anti-HPV E6 antibody. For ASC-US or ASC-H samples, about 33% to 38% of these samples are stained positively by the same anti-HPV E6 antibody as used for the LSIL, HSIL samples, indicating that the expression of oncogenic proteins in these ASC-US or ASC-H sample subjects may be underlying ≥CIN2 (CIN2 and above), and need to be followed up for further cancer progression. For samples with Pap smear diagnosed as ASC-US, and ICC staining (by anti-HPV E6 antibody) as negative, it may have less risk to develop progressive lesion. As the data have indicated, the ICC staining method using the anti-HPV E6 antibody described in some embodiments provides ICC assay sensitivity of 93% for ≥CIN2 with specificity of 74%. Similar ICC results were also found in the same samples using anti-HPV E7 antibodies. These data suggest the E6 or E7 antibody and E6E7 ICC test described in some embodiments can be useful biomarkers to detect HPV oncoproteins for 1). As adjunct test for triage Pap abnormal patients and 2). Co-test for screening of cervical cancer from general population along with routine Pap test.

In some embodiments, a kit for performing an immunocytological assay is provided. The kit may include an pre-antibody blocking solution, post-antibody blocking solution, an anti-HPV antibody as the primary antibody, an anti-mouse or anti-rabbit immunoglobulins conjugated with HRP or biotin, or other agents as secondary antibody, a solution containing appropriate agents used as substrate for the secondary antibody to be detected.

In some embodiments, nucleic acid hybridization assay on the clinical sample detects the presence of a Papillomavirus genome in the clinical sample from the human subject. The nucleic acid hybridization assays include polymerase chain reactions, nucleic acid hybridization assays, DNA chip assays, radioactive nucleic acid hybridization and detection assays, and non-radioactive nucleic acid hybridization and detection assays.

In addition, Pap normal samples were also tested by HPV E6 or E7 ICC and found staining negatively (44 out of 44) using anti-HPV antibody. These data indicate that the ICC staining assay described in some embodiments is very specific. Comparing to HPV DNA test results on the same samples, 16% (7 out of 37) of the Pap smear normal samples show positively on HPV DNA test. The high-grade HPV DNA test used in this study was HC2, an FDA approved HPV DNA test. For those HPV DNA positive but Pap normal and HPV ICC negative samples, it is possible they are false positives of the HPV DNA assay, or they are positive for HPV DNA with no detectable expression of HPV oncogenic proteins. Therefore, the HPV ICC assay described herein provides better clinical relevance for screening of cervical cancer compared to HPV DNA test.

Illustrative Example 2

Some embodiments are directed to immunoassay which comprises the detection of HPV oncoproteins and cellular proteins in cervical cancer. HPV E6 and E7 oncogenic proteins expressed in the tumor cells of cervical cancer can be detected in major portion of samples tested by IHC assay using the specific anti-E6 and anti-E7 antibody. These results strengthen the etiology and molecular mechanisms of HPV oncoproteins play in most cases of cervical cancer. The study results further demonstrate that the functional inactivation of p53 and pRB proteins by dysregulated viral E6 and E7 oncoproteins expression respectively, resulting in overexpression of $p16^{INK4a}$ (p16).

As data demonstrated, assay sensitivity of HPV IHC using anti-E6 antibody is about 92.1% (187 out of 203 cervical cancer tissues) with specificity of 100% (0 out of 3 normal cervical tissues). Among the 16 of IHC E6 negative samples, 15 show positive on IHC using anti-p16 antibody. Combined E6 and p16 IHC assay, it provides 99.5% of assay sensitivity (202 out of 203 samples are E6 or p16 IHC positive).

Assay sensitivity of HPV IHC using anti-p16 antibody is about 91.3% (190 out of 208). Among the 18 of IHC p16 negative samples, 17 samples show positive on IHC using anti-E6 antibody. Combined p16 and E6 IHC assay, it provides 99.5% of assay sensitivity (202 out of 203 samples are p16 or E6 IHC positive)

Assay sensitivity of HPV IHC using anti-E7 antibody is about 76.2% (154 out of 202). Among the 48 of IHC E7 negative samples, 28 samples show positive on both E6 and p16, 5 samples show E6 positive and p16 negative, 14 samples show E6 negative and p16 positive, only one sample are all negative in E6, E7, and p16. Combined E6, E7 and p16 IHC assay, it provides 99.5% of assay sensitivity (201 out of 202 samples are E6, E7 or p16 IHC positive)

For the samples shown discrepancy expression of HPV E6/E7 oncoproteins and p16 cellular protein in cervical cancer, it is possible that various pathways are involved in cancer development for those individual cases. Data suggest that multiple biomarkers (i.e. combined E6 and p16 IHC assay) are required to detect 99.5% (close to 100%) of cervical cancer.

Both HPV oncoproteins and cellular proteins play important roles in carcinogenesis to serve as biomarkers for diagnosis of HPV associated cancers. More biomarkers to be studied in different HPV associated cancers will help to provide personalized medicine.

Accordingly, some embodiments provides a monoclonal antibody capable of recognizing a common epitope on E6 protein from two different HPV types, both HPV16 and HPV18 by screening antibody-producing hybridoma cells with a purified HPV16 E6 recombinant protein and a purified HPV18 E6 recombinant protein. Some embodiments provide a monoclonal antibody that recognizes a common epitope on HPV16 E7 and HPV18 E7 proteins. As examples, the monoclonal antibodies were used to test on various biological samples, cell lines, and/or clinical samples of various grades of epithelial lesions (CIN2, CIN3, LSIL, HSIL, ASC-US) as well as different cervical cancers, squamous cell carcinoma (SCC, a type of common cancer) and adenocarcinoma (ADC, a type of gland cancer).

In some embodiments, a method of screening a human subject of Papillomavirus infection includes obtaining a clinical sample from the human subject, and conducting one or more immunological assays on the clinical samples from the human subjects using various HPV recombinant proteins and lab-generated antibodies specific for HPV oncoproteins in order to detect and screen for the presence of HPV infection from the presence of HPV proteins and HPV antibodies in the human subjects. In some embodiments, the HPV proteins in the human subjects are detected using antibodies raised against HPV recombinant proteins, including but not limiting to various polyclonal and monoclonal antibodies against various HPV early and late proteins.

Cloning of an exemplary oncogenic E6 or E7 early gene is described herein. DNA fragment containing the amino acid coding region of the HPV-16 E6. E7 or L1 gene was obtained by polymerase chain reaction (PCR) amplification. The DNA fragment was sub-cloned into a histidine tag expression vector to generate the plasmid DNA for the expression of E6 or E7 recombinant protein. Other types of expression vectors with histidine tag (e.g., $His_6$, $His_8$, etc.), glutathione-S-transferase (GST) fusion, maltose-binding-protein (MBP), among others, was also used. In addition, the DNA fragment can be sub-cloned into other expression systems, i.e. e. bacilobirus, yeast, etc to express E6 or E7 recombinant proteins from various HPV types and strains. For example, L1 recombinant protein from HPV 16 expressed in baculovirus was obtained and designated as HPV-16-L1-baculo.

The E6 or E7 recombinant proteins were expressed in *E. coli* BL21 (DE3) using IPTG driven induction. After two hour induction of protein expression at 37° C., The E6 or E7 recombinant proteins using standard protocols recommended by the suppliers (Amersham and New England Biolabs, respectively) were obtained and purified to a final concentration of about 1 mg/L. Longer induction time and re-flow through on protein purification column were found to generate higher protein yield, resulting in highly concentrated purified recombinant proteins at a yield of about 2-10 mg/L. The purity of the recombinant GST-E6 or His E6 proteins was estimated to be >90% based on PAGE analysis. Recombinant E6 or E7 fusion proteins was used to detect the presence of E6 or E7 antibody on clinical samples and was also be used as immunogens for production of polyclonal antiserum and monoclonal antibodies.

The basic techniques for cloning and for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art. The related immunological assays, immunohistochemistry for tissues and/or cervical cells, and/or immunocytological assays followed by flow cytometry are cross related to U.S. patent application Ser. No. 11/559,366, filed on Nov. 13, 2006, now U.S. Pat. No. 7,732,166, entitled "Detection Method for Human Papillomavirus (HPV) and Its Application in Cervical Cancer", U.S. patent application Ser. No. 12/082,740, filed on Apr. 14, 2008, now U.S. Pat. No. 7,972,776, entitled "Protein Chips for HPV Detection", U.S. App. Ser. No. 61/131,991, filed on Jun. 13, 2008, entitled "Antibodies and Assays for HPV Detection", and U.S. App. Ser. No. 61/192,912, filed on Sep. 22, 2008, entitled "Novel Monoclonal Antibodies against HPV Proteins Useful for Early State and Late Stage Detection, Screening, and Diagnosis of HPV Related Cervical Cancer", U.S. application Ser. No. 12/456,053, filed on Jun. 10, 2009, entitled "Novel Monoclonal Antibodies against HPV Proteins", U.S. application Ser. No. 12/456,054, filed on Jun. 10, 2009, entitled "in situ Detection of Early Stages and Late Stages HPV Infection", U.S. application Ser. No. 12/456,055, filed on Jun. 10, 2009, entitled "in situ Detection of Early Stages and Late Stages HPV Infection", U.S. application Ser. No. 12/456,076, filed on Jun. 10, 2009, now U.S. Pat. No. 8,278,056, entitled "Detection of Early Stages and Late Stages HPV Infection", U.S. App. Ser. No. 61/199,013, filed on Nov. 12, 2008, entitled "Detection, Screening and Diagnosis of HPV Associated Cancers", and U.S. application Ser. No. 12/590,747, filed on Nov. 12, 2009, entitled "Detection, Screening and Diagnosis of HPV Associated Cancers". The contents of the above cross-related applications are hereby incorporated by reference in their entireties.

Various embodiments also provides various methods, detection assays, and kits, polyclonal and monoclonal antibodies, polypeptides, recombinant proteins, and nucleic acids useful for detecting general HPV infection as well as infection by various HPV genotypes, high risk HPVs and low risk HPVs. In addition, the assays or sample formats in detecting the presence of HPV proteins are not limited and can be used for cervical tissues, cervical cells, cervical scrapes, serum, body fluids, etc. The useful screening or diagnosing assay can be IHC, ICC, flow cytometry, antibodies coupled to beads, rapid tests, protein chips, dot blots, slots, as well a conventional ELISA assay. HPV proteins can be detected by the antibodies described in some embodiments to be present in epithelium tissue as evidenced by IHC staining after scoring by a pathologist.

Detection of HPV DNAs, genomes, early viral proteins, late viral proteins, oncoproteins, and/or capsid proteins from various HPV genotypes can be performed by various in vitro and in vivo method and detection assays according to "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals and can be very useful in general clinical screening for HPV infection.

Detection of HPV antibodies and/or oncoproteins by immunological assays can be used in early clinical screening for HPV infection and general diagnosis for cervical cancer. Comparative detection of altered levels of HPV proteins and host proteins can be performed in the same or different assays. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological Papanicolaou smear tests or histological tests and the results thereof can be compared for follow-up patient management.

More Detailed Examples

Human Papillomavirus (HPV) infection is acknowledged to play an important etiological role in cervical dysplasia and cancer. There are two FDA approved HPV DNA tests; neither detects downstream events such as translation or transcription of the viral genome. While these tests can detect the presence of HPV DNA, they cannot differentiate a true precancerous state from a self-limited HPV infection. Thus, there is a clinical need to differentiate between those HPV infected individuals with self-limited infection from those with clinically significant disease. Moreover, there is also a critical clinical need to identify molecular diagnostic adjuncts to improve specificity of the cervical cytology test for detection of high-grade dysplasia and carcinoma and reduce the risk of false-negative cervical cytology test results. The mechanism by which HPV contributes to cancer development is attributed in large part to the actions of the HPV E6 and E7 oncogenes. These oncoproteins inactivate tumor suppressor genes that operate at key cell cycle checkpoints. HPV E6 and E7 interact with and degrade p53 and retinoblastoma (RB) respectively, a tumor suppressor who releases the transcription factor E2F to induce apoptosis. E7, serving multi-purposely, also stimulates cell cycle genes, blocks the function of the cyclin-dependent kinase inhibitors and induces aneuploidy which contributes to tumorigenesis. In precancerous lesions, E6 and E7 protein is expressed at much higher levels than found in benign tissue, and this increased expression of HPV E6 and E7 oncoprotein indicates progression of HPV infection to precancer. Therapeutic agent was found effectively to block function of E7. Therefore, the ability to detect E7 oncoprotein as a specific biomarker for high grade CIN 2/3 is a critical advance that would allow practitioners to 1). Differentiate HPV infection from true precancerous lesions, 2). Identify high-grade dysplastic cells and tumor cells in cervical tissues, 3). Prevent unnecessary colposcopies and biopsies in woman with benign HPV infection. E6 and E7 oncoprotein has been historically difficult to isolate. We have developed highly specific proprietary antibodies against HPV E6 or E7 oncoproteins. In addition to cervical cancer, the presence of HPV DNA has been detected in tumor tissues from the lower anogenital tract (anus, vulva, vagina and penis, and some oral, head and neck, and skin cancers. The E6 E7 biomarkers we have developed are anticipated to be useful for detecting cancers/precancers associated with HPV infection in multiple populations and organ sites. The technical challenge is that in cervical cytologic samples, HPV-related oncoproteins generally are present at low levels due to the mixture of morphologically normal cells with a minor fraction that is morphologically abnormal.

HPV E6 E7 oncogenes, key factors in the pathogenesis of cervical cancers, are over-expressed in dysplastic and malignant cells. Both E6 and E7 genes possess proliferation-stimulating activity. These genes and their respective proteins play a significant role for malignant transformation. Though their joint function results in an increase in transforming activity, they each carry their own carcinogenesis pathway and each can independently immortalize human cells. Thus each of E6 and E7 oncoproteins has to be treated as a key marker for cervical cancers. E6 or E7 oncoprotein acts as a multifunctional protein to deregulate multiple critical cellular pathways necessary for oncogenesis. Overexpression of E6 and E7 oncoprotein of carcinogenic HPV types has been suggested to be a very specific marker for cervical cancer. Thus, detection of E6 and E7 oncoprotein in tissue promises to be a more direct and specific test to identify true precancers than the detection of high-risk HPVs or other endogenous cell cycle markers. However, no one has yet successfully developed anti-E6 or anti-E7 antibody as biomarkers suitable for clinical diagnosis.

Current HPV DNA tests detect infection with high-risk HPV types, but cannot differentiate between benign HPV infection and high-grade precancerous lesions. Other evolving biomarker assays, such as p16 and proExC detect endogenous cellular markers not specific to HPV infection. HPV E6E7 mRNA tests detecting oncogene transcripts demonstrate improved specificity over Pap and HC2 tests, but the test procedure requires expensive and sophisticated instrumentation. Additionally, the mRNA test may not be favorable for routine clinical diagnosis due to its extremely low abundance and the inherent tendency for RNA degradation. In situ hybridization (ISH) detects HPV DNA or E7 mRNA in tissue, but it is not widely adopted in the clinical laboratory. HPV E6 E7 oncoprotein serves as a better biomarker than tests for E6 E7 mRNA because IHC is more robust than ISH, and oncoproteins are the actual end products of oncogenes directly interacting with and blocking RB tumor suppressor proteins involved in apoptosis and abnormal cell growth. However, IHC for HPV E6 E7 is not available yet for in vitro diagnosis. To date, only limited anti-HPV E6 or E7 antibody is available. Our anti-HPV E6 or E7 antibody is produced against non-denatured HPV E6 or E7 recombinant protein. Using the specific anti-E7 antibodies we have developed, we aim to develop a robust IHC platform for a diagnostic test to directly detect HPV E6 or E7 protein as the key factor to identify high-grade CIN 2/3. We envision that this platform can be expanded to a robust HPV E7 immunoassay that can differentiate precancerous lesion from benign HPV infection on cytologic samples, thereby identifying those who would benefit from medical intervention in a screening setting.

Detailed Example 1

Some embodiments are directed to monoclonal antibodies against HPV proteins. Obtaining high quantity of purified recombinant HPV proteins in native conformation as immunogen becomes the first critical step in generating antibodies specific for detecting HPV proteins in clinical samples. E6 and E7 is known to be very difficult to isolate and purify due to undesirable aggregation during protein purification, protein instability, low levels of expression, and low immunogenic responses of purified proteins. We have overcome the technical bathers to produce HPV E6 and E7 recombinant protein in a non-denatured, soluble form. To demonstrate that the purification method that we have developed results in a conformation closely approximating the native form to bind the anti-HPV antibodies, we have used the HPV infected cervical samples (high risk-HPV positive by PCR) that contain human HPV antibody to test the purified recombinant HPV proteins. Studies of using such purified E6 and E7 recombinant protein to detect HPV infection confirmed the binding of these proteins to anti-HPV antibody produced by human immune response to HPV infection. These results suggest that such purified recombinant HPV proteins are suitable for use as an immunogen to raise antiserum and generate antibodies that can recognize natural HPV viral proteins in vivo. We have used non-denatured, soluble E6 and E7 recombinant proteins for antigenic stimulation and have thereby developed highly specific proprietary antibodies against HPV E6 and E7 oncoproteins.

Initial studies have supported the use of our novel anti-E6 and anti-E7 antibody via different applications: ELISA, Western blot, and immunohistochemistry (IHC) in cervical cancer tissues. The validation results from clinical samples suggest our anti-E7 monoclonal antibody can be used as a biomarker for identification of high-grade dysplasia in cervical tissues, and can be potentially further developed for clinical diagnosis.

HPV recombinant proteins can be any kind of HPV viral proteins, HPV proteins of early genes and/or late genes, including, but not limited to, E2, E6, E7, L1, L2 and can be from various HPV types. Some embodiments provide recombinant proteins, such as recombinant hybrid proteins containing a partial sequence or a full length sequence of HPV oncogenic proteins. For example, full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus unsuitable as commercialized diagnostic tools.

HPV recombinant proteins were produced to use as immunogens for generating antiserum, and screening of monoclonal antibody from hybridoma cell lines: Cloning and production of various recombinant proteins include genes encoded by HPV16 E6 and HPV18 E6 gene, HPV16 E7 and HPV18 E7 gene, HPV16 L1 and HPV18 L1 gene. To provide the recombinant proteins mostly in (or close to) their native forms with much desirable conformation, recombinant HPV E6, E7 or L1 proteins expressed in *E coli* was purified from soluble fraction, then concentrated, and dialyzed with PBS to be used as immunogen. Immunization of mice and fusion was done by standard procedure to select clones met our screening criteria on ELISA. Each hybridoma cell line was grown in tissue culture and injected to mice for ascites production. Ascites were collected, isotyped, and purified by Protein G column for use in HPV immunoassays.

There are more than 40 HPV types identified in genital infection with 15 types identified as high-risk type from cervical cancer, among which HPV type 16 accounts for about 50% and type 18 accounts for an additional 20-25% of cervical cancer cases. However, since many HPV infections—including HPV 16 and HPV 18 infections—are self-limited, detection of HPV E6 and E7 oncoprotein in tissue can be the most direct and robust test to identify high-grade dysplasia cells, regardless of HPV types. Our goal was to obtain HPV E7 specific monoclonal antibody capable of reacting with most high-risk HPV types associated with cancer development. We screened hybridoma clones with HPV recombinant proteins from HPV type 16 and type 18 (accounting for about 75% of cervical cancer cases) to identify clones capable of detecting the relevant protein from the majority or all of the high risk HPV types. In addition, we screened hybridoma clones with unrelated HPV proteins to eliminate those with non-specific binding to HPV structural proteins. The purified recombinant human Papillomavirus proteins used in the hybridoma screening include, but are not limited to, HPV 16 E6 protein, HPV 16 E7 protein, HPV 16 L1 protein, HPV 18 E6 protein, and HPV18 E7 protein. Comparing our IHC results with HPV genotyping data from the tissues tested, our anti-E7 antibodies identify most of the common high-risk types, including not only HPV 16 and HPV 18, but also additional high-risk types closely related to type 16 (i.e. type 31, 33, 35, 52, 58) and type 18 (i.e. type 45).

Some embodiments are directed to resolve three challenges that exist in developing E7 antibodies for CIN2/3. First, HPV proteins are present in clinical samples in such small quantities that they are difficult to isolate. Second, there are many HPV types each with a distinct E7 coding sequence. Third, HPV proteins have not been successfully mass produced and purified from HPV infected cultured cell lines to be used as an immunogen for antibody production. Known anti-HPV antibodies produced against either small synthetic peptides or denatured recombinant protein are generally unsuitable for use in clinical diagnosis, because they do not necessarily react with the naturally occurring HPV viral proteins in infected human cells. Another technical challenge is the conformation change that occurs in naturally infected human tissue upon formalin fixation and paraffin embedding, making the proteins difficult to detect in clinically relevant samples. These factors provide an explanation for the fact that the available antibodies produced from denatured recombinant proteins or synthetic peptides do not work for IHC. In addition, it was also known that certain immunological assays using small peptides of the E7 protein results in extremely low assay specificity and sensitivity. Thus, there are no available E6 or E7 proteins in native form purified as immunogens for generating anti-HPV antibodies capable of detecting viral proteins present in clinical samples for in vitro diagnosis.

Detailed Example 2

Immunocytochemistry Assay (ICC)

Some embodiments are directed to immunoassay comprising the detection of HPV proteins and cellular proteins in exfoliated cervical cells. Sample preparation: The cervical scrape cells collected from liquid based solution were divided into two parts, one for cytological Papanicolaou staining, and another one for immunocytochemical staining using HPV antibodies described in some embodiments. In the Pap smear results, Papanicolaou staining samples were scored 0-17. Score one (1) to three (3) are considered as normal, and score four (4) and above as abnormal. Interpretation of Pap smear reports can be challenging at times. Based on the Bethesda 2001 system, negative Pap smear may include negative intraepithelial lesion or malignancy, and abnormal Pap smear may include different stages of squamous cells in development of dysplasia or lesions. For examples, LSIL: Low grade of Squamous Intraepithelial Lesion, HSIL: High grade of Squamous Intraepithelial Lesion, CIN 1: Cervical Intraepithelial Neoplasia; mild cell abnormalities, CIN2: Cervical Intraepithelial Neoplasia with lesions appearing more aggressive, CIN3: Cervical Intraepithelial Neoplasia with aggressive form of dysplasia. Invasive cancers may include squamous cell carcinoma (SCC), adenocarcinoma (ADC), and others. Underdetermined abnormal cells include ASC-US, Atypical Squamous Cells of Undetermined Significance, unusual or atypical cells in Pap smear that may be inconsequential and its significance is underdetermined, and AGUS, Atypical Glands of Undetermined Significance. For the identified abnormal cells, HPV ICC staining may provide additional information for the status of HPV infection and/or the expression of HPV oncoproteins. Therefore, HPV ICC staining assay is very useful to identify high-grade dysplasia cells from Pap LSIL or HSIL samples, and/or for those underdetermined abnormal cells like ASC-US, or AGUS, comparing to the Papanicolaou staining.

As an example of immunoassay using ICC methods, cells from cervical scrapes were collected, centrifuged, washed, and immunostained followed by the ICC procedure described herein. Cervical scrapes collected by liquid based solution were processed according to the manufacture instruction. The cervical cells were then processed by cytospin or thin prep techniques into monolayer. The monolayer of cells on slide were then fixed and stained by anti-HPV antibodies followed by HPV ICC protocol. Stained cells are visualized under microscope.

In some embodiments, a kit for performing an ICC assay is provided. The kit may include an pre-antibody blocking solution, post-antibody blocking solution, an anti-HPV antibody as the primary antibody, an anti-mouse or anti-rabbit immunoglobulins conjugated with HRP or biotin, or other agents as secondary antibody, a solution containing appropriate agents used as substrate for the secondary antibody to be detected.

The anti-HPV antibodies may also be directly tagged with HRP or biotin, or other agents to be detected using appropriate agents as substrate. The pre-antibody blocking solution may contain certain proteins, BSA, serum or other agents to block the cells from nonspecific binding of the primary antibody. The post-antibody blocking solution may contain similar solution as the pre-antibody blocking solution with less amount of blocking proteins or serum to be used along with primary antibody incubation. The solution containing HPV antibodies may be in concentrated form, or may be in diluted form as ready to use reagent. The solution containing secondary antibodies may be in concentrated form, or may be in diluted form as ready to use reagent. The solution containing appropriate agents used as substrate may include DAB (3.3'-diaminobenzidine) as one component, or two components, or AEC (3-Amino-9-Ethylcarbazole) substrate as one component, or two components, or other substrates.

Once the human cells from cervical scrapes are processed and fixed into a monolayer or thin layer of cells on the slide, the Immunocytochemistry (ICC) assay is performed by blocking the slides with pre-antibody blocking solution for a period of time followed by the incubation with the HPV antibodies. The slides were then washed 3 to 5 times with PBS or $H_2O$, or other solution to remove any unbound HPV antibody. Then the slides were incubated with the secondary antibody, for example, anti-mouse IgG HRP, followed by washing and binding of appropriate substrate for detection. As an example for the substrate, DAB is oxidized in the presence of peroxidase and hydrogen peroxide resulting in the deposition of a brown, alcohol-insoluble precipitate at the site of enzymatic activity. The precipitate may range in color from a light golden brown to dark golden brown depending upon the amount of enzyme present. The golden brown precipitation viewed under a microscope indicates the specific binding of HPV antibodies with HPV proteins present in the cells. The assay can be performed at room temperature or higher temperature to accelerate the binding reaction. This HPV ICC assay can be performed manually, or operated by ICC automation, thus provides a powerful tool to screen for HPV infection and detection of HPV oncoproteins in situ localized in the epithelium cells from cervical scrapes.

To demonstrate that the HPV ICC assay can identify dysplasia cells from different disease stages, samples from mild, moderate, severe, or invasive of neoplasia were all tested. These samples include but not limited to, for example, CIN1, CIN2, CIN3, LSIL, HSIL or ASC-US. To demonstrate that the ICC assay described herein can be used to stain for various sample sources from various stages in various liquid based solutions, different stages of samples in different liquid based solutions were also prepared to perform ICC assay in some embodiments.

Moderate dysplasia means that the skin of the cervix is growing moderately faster than it should and has progressed beyond the mild stage. A biopsy of the cervix shows immature basal cells growing partway through to the surface of the skin, without significant maturation. Moderate dysplasia is important because there is a much greater risk that these changes will advance, and if untreated, it will progress into invasive cervical cancer. For that reason, moderate dysplasia is known as a "high grade" lesion, or HGSIL. Another synonym for this condition is "CIN2" (Cervical Intraepithelial Neoplasia, Grade II). Moderate dysplasia on a Pap smear usually indicates that further study of the cervix with colposcopy is needed. If moderate dysplasia is confirmed, then it is usually treated. Treatments might include cryosurgery, LEEP, or laser. Following treatment, frequent Pap smears are usually obtained as follow-up to make sure that if there is a recurrence (about 10% chance), that the recurrence is promptly diagnosed and further treatment performed.

To demonstrate that the HPV ICC assay can detect HSIL cells, FIG. 1A shows cervical scrape cells diagnosed as CIN2 by Papanicolaou staining prepared in another liquid base solutions can be ICC stained positively using an anti-E7 monoclonal antibody. As shown in FIG. 1A, the CIN2, HSIL abnormal cells in the form of connecting each other with high N/C (nuclear/cytoplasm) ratio (indicated as black arrow) was stained positively to the nucleus and cytoplasm. These results demonstrate that in the ICC assay, by using the mouse monoclonal anti-HPV E7 antibody, HPV E7 protein present can be detected in situ in the abnormal cells from intermediate stage of neoplasm in various sources of liquid based solutions.

FIG. 1B shows another CIN2 sample of cervical scrape cells prepared in another liquid base solutions can be ICC stained positively using an anti-E6 monoclonal antibody. As shown in FIG. 1B, the CIN2, HSIL abnormal cells in the form of connecting each other with high N/C (nuclear/cytoplasm) ratio (indicated as black arrow) was stained positively to the nucleus and cytoplasm. These results demonstrate that HPV E6 protein present in situ can be detected in the abnormal cells from intermediate stage of neoplasm, in various source of liquid based solution using the mouse monoclonal anti-HPV E6 described here in the ICC assay.

If the abnormal cells invade through the basement membrane into the underlying tissues, they are considered cancer. For severe dysplasia, it is not considered as cancer but a pre-cancerous problem as the abnormal cells in dysplasia do not invade through the basement membrane. Thus, by definition, they are not cancer. Carcinoma in situ means that there are abnormal cells extending the full thickness of the skin. These cells individually look just like cancer cells. Carcinoma in situ is considered by many authorities to be clinically equivalent to severe dysplasia, or CIN3, and it should be promptly and carefully evaluated. Treatment might include eliminating the abnormal cells by freezing them (cryosurgery), vaporizing them (laser), or shaving them off with an electrified wire loop (LEEP). In some circumstances, more extensive surgery in the form of a cervical cone biopsy is required to eliminate the problem.

Figure 2:
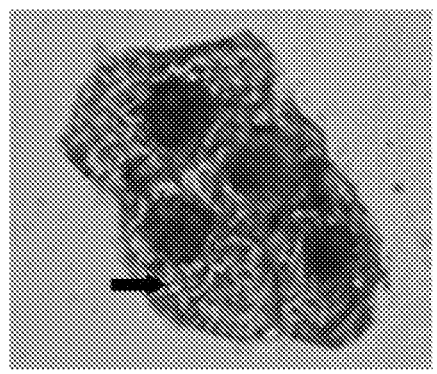
FIG. 2 shows the results of ICC staining of a clinical sample diagnosed as CIN3 in a liquid based solution using an anti-HPV E6 mouse monoclonal antibody.
Figure 3A:
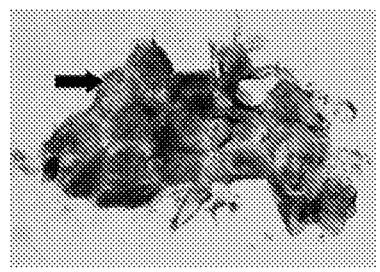
FIG. 3A-3D shows the representing images from results of ICC staining of another clinical sample diagnosed as CIN3 in another liquid based solution using the same anti-HPV E6 mouse monoclonal antibody shown in FIG. 2.
Figure 3B:
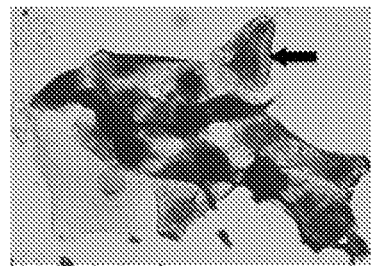
Figure 3C:
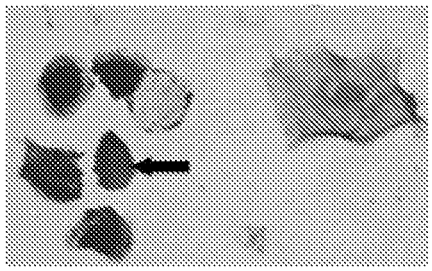
Figure 3D:
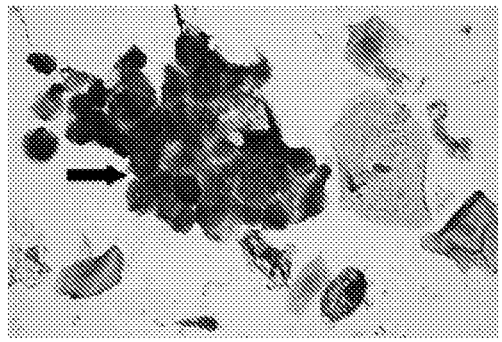

To demonstrate that the ICC assay described herein can be used for severe cervical intraneoplasia cells in liquid based solution, CIN3 cervical scrape samples in different liquid based solution were also prepared to perform ICC assay described in some embodiments. FIG. 2 shows that cervical scrape cells (diagnosed as CIN3 by Papanicolaou staining) can be ICC stained positively using an anti-E6 monoclonal antibody. FIG. 3A-3D shows another CIN3 sample of ICC staining results using the same anti-HPV E6 mouse monoclonal antibody. As shown in FIG. 3A-3D, the CIN3, HSIL abnormal cells in the form of connecting each other with high N/C (nuclear/cytoplasm) ratio (indicated as black arrow) was stained positively to the nucleus and cytoplasm. These results demonstrate that the presence of the HPV E6 protein in situ can be detected in the abnormal cells from intermediate stage of neoplasm, in various source of liquid based solution using the mouse monoclonal anti-HPV E6 described here in the ICC assay. These results also demonstrate that in the ICC assays, the presence of the HPV E6 protein in situ can be detected in the abnormal cells from CIN3 of liquid based solutions using the mouse monoclonal anti-HPV E6 antibody.

Figure 4A:
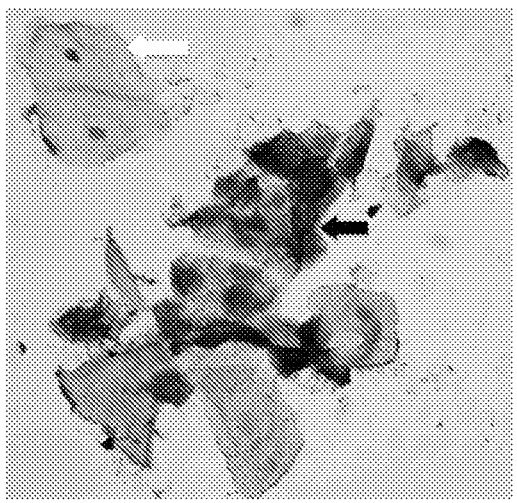
FIG. 4A shows the results of ICC staining from the same CIN3 sample shown in FIG. 3A-3D using an anti-HPV E7 mouse monoclonal antibody.
Figure 4B:
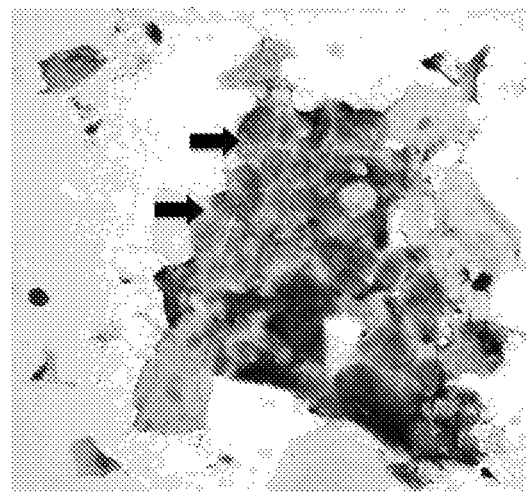
FIG. 4B shows another image of the same ICC staining results shown in FIG. 4A using the same anti-HPV E7 mouse monoclonal antibody.

FIGS. 4A and 4B shows two representative images of ICC staining using an anti-HPV E7 mouse monoclonal antibody from the same CIN3 sample as shown in FIG. 3A-3D. The images demonstrate that the CIN3, HSIL abnormal cells that are in the form of connecting each other with high N/C (nuclear/cytoplasm) ratio (indicated as black arrow) was stained positively to the nucleus and cytoplasm. These results demonstrate that in ICC assays, the presence of the HPV E7 protein in situ can be detected in the abnormal cells from intermediate stage of neoplasm, in various source of liquid based solutions using the mouse monoclonal anti-HPV E7. These results demonstrate that HPV E7 protein present in situ can be detected in the abnormal cells from CIN3 of liquid based solution using the mouse monoclonal anti-HPV E7 described here in the ICC assay.

Figure 5:
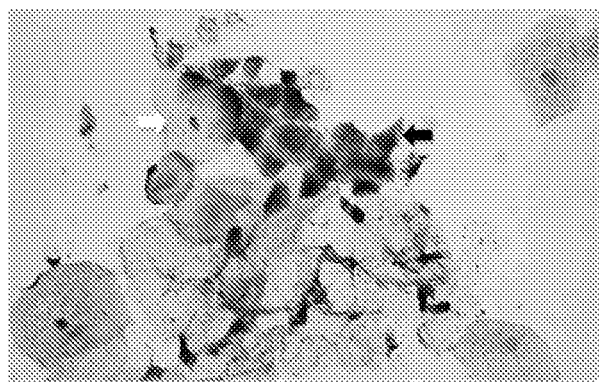
FIG. 5 shows the results of ICC staining from the same CIN3 sample shown in FIG. 3A-3D using an anti-p16 (p16$^{INK4a}$)mouse monoclonal antibody.

To confirm p16 is also overexpressed in the late stage of neoplasm, ICC staining was performed using an anti-p16 mouse monoclonal antibody on the same CIN3 samples as shown in FIGS. 3 and 4. FIG. 5 shows the results of ICC staining from the same CIN3 sample using an anti-p16 mouse monoclonal antibody. As shown in the Figures, the CIN3, HSIL abnormal cells in the form of connecting each other with high N/C (nuclear/cytoplasm) ratio (indicated as black arrow) was stained positively to the nucleus and cytoplasm. These results demonstrate that the presence of the p16 protein in situ can be detected in the abnormal cells from intermediate to late stage of neoplasm. All these results presented in FIGS. 2-5 demonstrate that the presence of the HPV E6, HPV E7, and p16 proteins in situ can be detected in the abnormal cells from CIN3 of liquid based solution using the mouse monoclonal antibodies described here in the ICC assay.

Cancer of the cervix is among the most common forms of cancer affecting the reproductive organs. It is locally invasive into neighboring tissues, blood vessels, lymph channels and lymph nodes. In its advanced stages it can be difficult to treat and may prove fatal. Prior to developing cancer of the cervix, there is usually a period of pre-cancerous change that is reversible, known as dysplasia. While most cancer of the cervix comes from the squamous cells making up the exterior skin, there is an occasional cancer that arises from the mucous-producing cells which line on the endocervical canal leading up into the uterus. This glandular-type is called "adenocarcinoma (ADC)" as opposed to "squamous cell carcinoma (SCC)". Unlike squamous cell cancer, adenocarcinoma precursors, when present, can be difficult to identify on Pap smears, thus making adenocarcinoma difficult to detect. The slow progression of squamous cell dysplasia into squamous cell cancer of the cervix is not as uniform in adenocarcinoma. Consequently, adenocarcinoma of the cervix is frequently detected at a more advanced stage than squamous cell carcinoma. Treatment is similar to that of the more common squamous cell cancer. However, since it is more often found at a more advanced stage, more aggressive treatment is often needed. Thus, it becomes critical to detect the presence of the HPV oncoproteins from early screening of adenocarcinoma cells in the liquid-base solutions using the HPV ICC assay described in some embodiments.

Figure 6A:
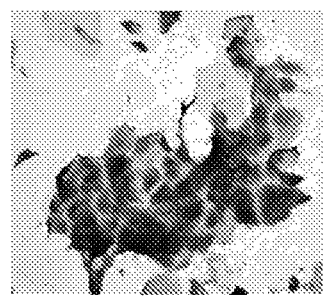
FIG. 6A shows the results of ICC staining of a clinical sample diagnosed as squamous cell carcinoma (SCC) in a liquid based solution using an anti-HPV E6 mouse monoclonal antibody.
Figure 6B:
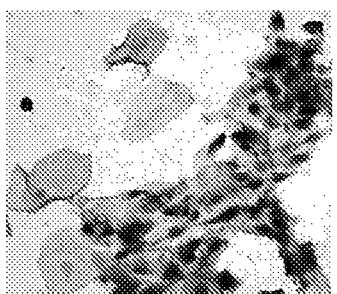
FIG. 6B shows the results of ICC staining of the same SCC sample shown in FIG. 6A using an anti-HPV E7 mouse monoclonal antibody.
Figure 6C:
FIG. 6C shows the results of ICC staining of the same SCC sample shown in FIG. 6A using an anti-p16 mouse monoclonal antibody.

As another example to demonstrate that the ICC assays described herein can be applied to detect cervical cancer cells in liquid based solutions, different carcinoma of cervical scrape samples in different liquid based solutions were also prepared to perform the ICC assays described in some embodiments. As an example, FIG. 6A shows that one of the most common cervical cancer types, SCC (diagnosed as squamous cell carcinoma by Papanicolaou staining) can be ICC stained positively using an anti-E6 monoclonal antibody. FIG. 6B shows the results of ICC staining using an anti-HPV E7 mouse monoclonal antibody on the same SCC sample shown in FIG. 6A. To confirm that p16 is also overexpressed in the late stage of neoplasm, ICC staining using an anti-p16 mouse monoclonal antibody was performed on the same SCC sample used in FIGS. 6A and 6B. FIG. 6C shows the results of ICC staining using an anti-p16 mouse monoclonal antibody on the same SCC sample shown in FIGS. 6A and 6B. As shown in the FIG. 6A-C, the HSIL SCC cells are in the form of connecting each other with high N/C (nuclear/cytoplasm) ratio (indicated as black arrow) and was stained positively to the nucleus and cytoplasm. These results demonstrate that the presence of the HPV E6, HPV E7, and p16 proteins in situ can be detected in the abnormal cells from different type of cervical cancers of liquid based solutions using the mouse monoclonal antibodies described here in the ICC assay.

Figure 7A:
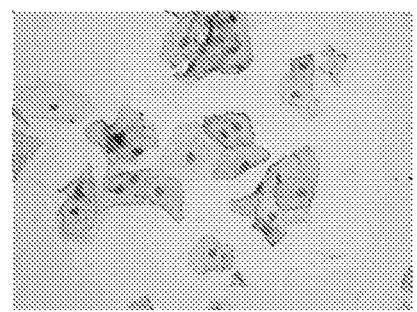
FIG. 7A shows the results of ICC staining of a clinical sample diagnosed as normal in a liquid based solution using an anti-HPV E6 mouse monoclonal antibody.
Figure 7B:
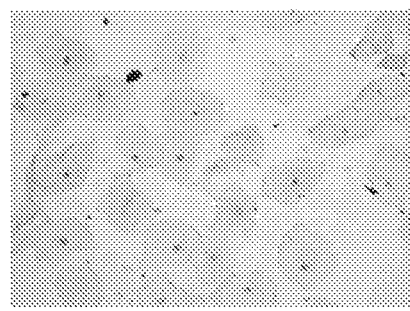
FIG. 7B shows the results of ICC staining of the same clinical sample as shown in FIG. 7A using an anti-HPV E7 mouse monoclonal antibody.

To demonstrate that the ICC staining described herein are resulted from the specific binding of the HPV antibody with the HPV proteins present in situ of the cervical scrape cells, normal cervical cells from liquid based solution were also obtained to test on the ICC assay. FIG. 7A shows normal cervical scrape cells diagnosed by Papanicolaou staining prepared in liquid base solutions stained negatively by ICC using an anti-E6 monoclonal antibody. ICC staining was also performed on the same samples using an anti-HPV E7 monoclonal antibody as shown in FIG. 7B. The ICC assay shows negative staining results using the mouse monoclonal anti-HPV E6 or the mouse monoclonal anti-HPV E7 antibody, thus demonstrates that neither HPV E6 protein, nor HPV E7 protein is present in situ in the normal cervical scrape cells. Therefore, the results indicate that the ICC assay described in some embodiments is a specific staining method for the detection of the HPV proteins using the HPV specific antibodies described herein.

Though many factors, including immune system impairment, contribute to the development of mild dysplasia, infection with HPV is probably the most important one. Mild dysplasia is not a permanent feature when it occurs. It can either regress or progress, making it being present on a woman's cervix (and Pap smear) at one time but not another. This results from the fact that the HPV virus that is a pre-requisite for these changes can lie dormant within the cervical skin cells. Normally held in check by the woman's immune system, the HPV can, at times of immune system distraction, reactivate the cellular machinery that leads to more rapid growth. For women who develop a single Pap smear showing mild dysplasia, there are basically three approaches that are commonly followed: 1). Repeated Pap in 6 months. Most of these Pap abnormalities turn out to be self-limited HPV infections, particularly among the adolescent women. Repeated Pap smears with no other treatment allow time for many of these cervices to heal, which avoids other more extensive intervention. On the other hand, the primary disadvantages of the repeated Pap approach are that for the majority of the women who will ultimately need colposcopy anyway and they have been subjected to varying degrees of anxiety over known, but unresolved health issues. 2). Immediate Colposcopy. Many women will feel anxiety over a simple observation of the abnormality without immediate investigation. The primary disadvantage to this approach is that even women with falsely positive Pap smears will undergo a moderately costly evaluation. 3). See and Treat. Instead of colposcopic evaluation and directed biopsies followed by some form of treatment a few days or weeks later, some physicians prefer to evaluate the cervix with colposcopy and to immediately perform a LEEP procedure at the same time, for those in whom the LEEP is appropriate. However, most of all, for most of the patients, it is an overtreatment.

A report of ASC (Atypical Squamous Cells) is the way that the cytologist uses to describe a Pap smear that is not perfectly normal. However, they can't tell with any certainty what kind of abnormality it is or how significant it is. ASC Paps are subdivided into two types: ASC-US (undetermined significance), ASC-H (cannot exclude high-grade SIL). Among the women diagnosed as ASC, there are a few who have high-grade lesions of the cervix. Between 5% and 17% of women with ASC-US will have a high grade SIL present (CIN2 or CIN3). Between 24% and 94% of women with ASC-H will have a high grade SIL. Thus, the probability of ASC Paps progressing to HSIL is not negligible. The risk of invasive cancer of the cervix is about 0.1% to 0.2% among women with any ASC Pap.

An HPV E6 or E7 immunocytochemical (ICC) assay not only detects HPV infection, but also detects HPV oncogenic proteins in situ. Therefore, ICC assay in combination with various specific and common anti-HPV antibodies can be a powerful tool for HPV detection in situ, as compared to a standard HPV DNA test or Pap smear assay.

Table 1 shows the results of an HPV E6 ICC assay using a mouse anti-HPV E6 monoclonal antibody on various cervical scrape samples in a liquid based solution. Total of 85 samples obtained from referral clinics were collected in ThinPrep. The results in Table 1 demonstrate that HPV E6 protein can be detected in situ on single cells fixed on a slide by immunocytochemical (ICC) assay using a mouse monoclonal anti-HPV E6 antibody. The in situ presence of HPV E6 proteins can be detected from various stages of cervical scrape samples in various liquid based solutions. The same cervical scrape samples were also processed by standard Papanicolaou staining to compare the ICC staining results with the Pap smear results. As shown in Table 1, HPV E6 proteins are present in the cervical scrape normal, ASC-US, ASC-H, LSIL, HSIL samples with increasing positivity rate, respectively.

There is about 100% positive rate for sample with Pap HSIL or CIN2/3, while only 14% of samples diagnosed with Pap normal stained positively by ICC using the same anti-HPV E6 antibody. For ASC samples, about 33% of ASC-US and about 50% of ASC-H are stained positively by the same anti-HPV E6 antibody used for the LSIL, HSIL samples shown in Table 1, indicating expression of oncogenic proteins in these ASC-US or ASC-H sample subjects to be followed up for further disease progression. For samples with Pap ASC-US and HPV E6 ICC staining negative, it may have less risk to develop progressive lesion. These results suggest the HPV E6 ICC assay described herein is very useful in providing additional information of HPV infection for disease management decision to make.

TABLE 1

ICC staining using a mouse anti-HPVE6 monoclonal antibody on various cervical scrapes samples in a liquid based solution.

| | Pap Test | | | | | |
|---|---|---|---|---|---|---|
| | Normal | ASC-US | ASC-H | LSIL | HSIL | SCC |
| E6 ICC positive | 4 | 3 | 4 | 11 | 17 | 4 |
| E6 ICC negative | 25 | 6 | 4 | 6 | 0 | 1 |
| total | 29 | 9 | 8 | 17 | 17 | 5 |
| positive rate | 14% | 33% | 38% | 65% | 100% | 80% |

Table 2 shows summary of the ICC staining results from Table 1. As data indicated, the ICC staining method using the anti-HPV E6 antibody described in some embodiments provides ICC assay sensitivity of 95% for ≥CIN2 with specificity of 66%. These data suggest this assay with 50% of PPV (positive predictive value) and 98% of NPV (negative predictive value), can be useful to detect HPV proteins for triage patients with abnormal Pap or screening of cervical cancer from general population along with routine Pap staining.

TABLE 2

Summary of the ICC staining results using a mouse monoclonal anti-HPV E6 antibody on CIN2 cervical scrape samples in a liquid based solution.

| | Pap HSIL positive | Pap HSIL negative | | |
|---|---|---|---|---|
| E6 ICC positive | 21 | 21 | 50% | PPV |
| E6 ICC negative | 1 | 41 | 98% | NPV |
| Sensitivity | 95% | | | |
| specificity | | 66% | | |

As another examples of HPV ICC assay, Table 3 and Table 4 show results of ICC staining using anti-HPV E7 antibody. As data shown, HPV anti-E7 gives comparable ICC results as HPV anti-E6 shown. Table 3 shows that HPV E7 proteins are present in the cervical scrape normal, ASC-US, ASC-H, LSIL, HSIL samples with increasing positivity rate, respectively. There is about 94% positive rate for samples diagnosed with Pap smear HSIL, while only 11% of samples diagnosed with Pap smear normal stained positively by ICC using the same anti-HPV E7 antibody. For ASC-US or ASC-H samples, about 40% of these samples are stained positively by the same anti-HPV E7 antibody as used for the CIN1, CIN2/3 samples shown in Table 3, indicating expression of oncogenic proteins in these ASC-US or ASC-H sample subjects to be followed up for further cancer progression. For samples with Pap smear diagnosed as ASC-US and ICC staining (anti-HPV E7) negatively, it may have less risk to develop progressive lesion.

TABLE 3

ICC staining results using a mouse monoclonal anti-HPVE7 antibody on various cervical scrape samples in a liquid based solution.

| | Pap normal | ASC-US | ASC-H | LSIL | HSIL | SCC |
|---|---|---|---|---|---|---|
| E7 ICC positive | 3 | 4 | 3 | 11 | 16 | 4 |
| E7 ICC negative | 25 | 6 | 5 | 6 | 1 | 1 |
| Total | 28 | 10 | 8 | 17 | 17 | 5 |
| positive rate | 11% | 40% | 38% | 65% | 94% | 80% |

Table 4 shows summary of the ICC staining results from Table 3. As data indicated, the ICC staining method using the anti-HPV E7 antibody described in some embodiments provides ICC assay sensitivity of 91% for HSIL+ with specificity of 67%. These data suggest that this assay, with 51% of PPV and 95% of NPV, can be useful to detect HPV proteins for triage patients with abnormal Pap or screening of cervical cancer from general population along with routine Pap smear staining.

TABLE 4

Summary of the ICC staining results using a mouse monoclonal anti-HPVE7 antibody on ≥CIN2 cervical scrape samples in a liquid based solution.

| | Pap HSIL positive | Pap HSIL negative | | |
|---|---|---|---|---|
| E7 ICC positive | 20 | 21 | 51% | PPV |
| E7 ICC negative | 2 | 42 | 95% | NPV |
| Sensitivity | 91% | | | |
| Specificity | | 67% | | |

As another example, total of 200+ cases of Pap cytology samples obtained from referral clinics were collected in LiquidPrep solution. Combinations of Pap test, HPV DNA test, with linked to histology results were correlated for analysis of expression of HPV E6E7 oncoproteins and cellular proteins. Total 117 cases with ICC results using anti-E6, anti-E7 and anti-p16 antibody for various stages of cervical scraps samples in liquid base solution were analyzed with results of Pap test, HPV DNA test, and histology. As an example, Table 5 shows correlation of results from Pap, HPV DNA test, and ICC test using E6, E7, or p16 antibody.

TABLE 5

Summary of ICC staining results showing 48 cases of Pap smear samples with various stages of abnormality compared to HPV DNA test and ICC tests using anti-HPV antibodies, anti-p16 antibody.

| Pap smear | | No cases | ImmunoCytoChemistry | | | | | |
|---|---|---|---|---|---|---|---|---|
| | | | E6+ | E6− | E7+ | E7− | p16+ | p16− |
| NML | HPV+ | 16 | 11 | 5 | 4 | 12 | 2 | 14 |
| | HPV− | 12 | 6 | 6 | 2 | 10 | 1 | 11 |
| ASC-US | HPV+ | 5 | 5 | 0 | 3 | 2 | 1 | 4 |
| | HPV− | 1 | 0 | 1 | 0 | 1 | 0 | 1 |
| CIN1/2/3 | HPV+ | 13 | 11 | 2 | 6 | 7 | 4 | 9 |
| | HPV− | 1 | 1 | 0 | 1 | 0 | 0 | 1 |

Data from Tables 5 demonstrate that ICC staining using anti-HPV antibody has better correlation for the positive rate with HPV DNA test compared to ICC using anti-p16 alone. Results suggest that HPV ICC can be used for early detection of HPV proteins in situ. For the false positive sample, for example, Pap normal, HPV positive samples, ICC can further confirm the expression of HPV oncogenic protein expression. For the false negative samples, for example, Pap normal, HPV negative samples, but ICC positive samples, it requires follow up to confirm if any lesion progression. However, most cases of ASC-US or CIN with HPV DNA positive samples show positive by HPV ICC using anti-E6 antibody. Compared to p16 ICC, HPV ICC has better correlation with the abnormality of Pap smear.

TABLE 6 comparison of HPV DNA test with E7 ICC
test using Pap test as gold standard

| Pap test | HPV | No cases | E7 ICC positive | E7 ICC negative |
|---|---|---|---|---|
| NML | HPV+ | 16 (57%) | 4 (14%) | 12 (43%) |
|  | HPV− | 12 (43%) | 2 (7%) | 10 (36%) |
| ASC-US | HPV+ | 5 (83%) | 3 (50%) | 2 (33%) |
|  | HPV− | 1 (17%) | 0 (0%) | 1 (17%) |
| LSIL | HPV+ | 8 (100%) | 2 (25%) | 6 (75%) |
|  | HPV− | 0 (0%) | 0 (0%) | 0 (0%) |
| HSIL | HPV+ | 5 (83%) | 4 (67%) | 1 (17%) |
|  | HPV− | 1 (17%) | 1 (17%) | 0 (0%) |

To analyze the correlation of HPV DNA and expression of HPV E6E7 oncoproteins, as an example, table 6 further demonstrate the positive rate of HPV E7 ICC compared to HPV DNA among different category of Pap test results from the 48 cases shown in Table 5. As data shown in Table 6, HPV DNA test shows positive rate of 57%, 83%, 100% and 83% compared to E7 ICC test shows positive rate of 21%, 51%, 25% and 84% for Pap NML, ASC-US, LSIL, and HSIL respectively. These data demonstrate high positive rate of HPV DNA test for patients from referral clinics, indicating HPV DNA is not useful for triage Pap abnormal patients. As data shown, 83% of ASC-US is HPV DNA positive, so only 17% of ASC-US/HPV negative patients can be saved from unnecessary colposcopy. However, 100% of LSIL is HPV DNA positive, indicating HPV DNA test is not recommended for triage LSIL patients. However, only 50% of ASC-US and 25% of LSIL shows E7 positive. It suggests E7 ICC test serves as a better test for triage Pap abnormal ASC-US and LSIL patients to significantly avoid unnecessary colposcopy or over testing. For HSIL group, both HPV DNA test and E7 ICC test shows 83% positive rate. For the HSIL/HPV DNA negative, it could be false negative of HPV DNA test since it shows positive on E7 ICC test. For the HSIL/HPV DNA positive, but E7 ICC negative, it requires further confirmation if it is true HSIL with histology over CIN2.

To further analyze the sensitivity and specificity of HPV DNA test and E7 ICC test from Table 6, Table 7 and Table 8 show results of E7 ICC test and HPV DNA test respectively using Pap HSIL as cut off.

TABLE 7

Compare E7 ICC with HPV DNA test using Pap test
as gold standard (total 48 cases from Table 6)

|  | Pap HSIL positive | Pap HSIL negative |  |  |
|---|---|---|---|---|
| E7 ICC positive | 5 | 11 | 31% | PPV |
| E7 ICC negative | 1 | 31 | 97% | NPV |
| Sensitivity | 83% |  |  |  |
| Specificity |  | 74% |  |  |

TABLE 8

Summary of HPV DNA test results compared to Pap test using
HSIL as cut off (total of 48 cases from Table 6)

|  | Pap HSIL positive | Pap HSIL negative |  |  |
|---|---|---|---|---|
| HPV positive | 5 | 29 | 15% | PPV |
| HPV negative | 1 | 13 | 93% | NPV |

TABLE 8-continued

Summary of HPV DNA test results compared to Pap test using
HSIL as cut off (total of 48 cases from Table 6)

|  | Pap HSIL positive | Pap HSIL negative |
|---|---|---|
| Sensitivity | 83% |  |
| Specificity |  | 31% |

As data shown in Table 8, the HPV DNA method provides a sensitivity of 83% for ≥CIN2 with specificity of 31% with 15% of PPV and 93% of NPV. Compared to Table 7 for the same patients from the same study using ICC staining with anti-HPV E7 monoclonal antibody, these two methods have the same assay sensitivity (83%). However, ICC staining assay using anti-E7 antibody demonstrates higher specificity (74% vs. 31%), better PPV (31% vs. 15%), and better NPV (97% vs. 93%). Thus, these results demonstrate that, compared to the HPV DNA method, HPV E7 ICC assay can be a better method to detect HPV proteins for screening of cervical cancer from general population along with routine Pap smear staining. Therefore, HPV E6 E7 serves as better biomarker for identifying high grade dysplasia and provides effective disease management for those who can benefit from medical intervention.

To further analyze HPV E7 ICC data with histology results, as another example, Table 9 and Table 10 show results of HPV E7 ICC staining using histology as the gold standard. Table 9 shows that HPV E7 proteins are present in the cervical scrape normal, CIN1, CIN2/3 samples with increasing positivity rate, respectively. There is about 94% positive rate for samples diagnosed with Pap smear CIN2/3, while 23% of samples diagnosed with histology results NIL (normal) stained positively by ICC using the same anti-HPV E7 antibody. For CIN1 samples, about 40% of these samples are stained positively by the same anti-HPV E7 indicating expression of oncogenic proteins in these CIN1 sample subjects to be followed up for further cancer progression. For samples with histology NIL/CIN1 and ICC staining (anti-HPV E7) negatively, it may have less risk to develop progressive lesion.

TABLE 9

Results of ICC staining using a mouse anti-HPV
E7 monoclonal antibody compared to histology.

| Histology | NIL | CIN1 | CIN2 | CIN3 |
|---|---|---|---|---|
| HPV E7 ICC positive | 14 | 6 | 11 | 15 |
| HPV E7 ICC negative | 48 | 9 | 1 | 1 |
| Total case No. | 62 | 15 | 12 | 16 |
| positive rate | 23% | 40% | 92% | 94% |

Total 105 cases obtained from referral clinics with the samples collected in LiquidPrep.

Table 10 presents a summary of the ICC staining results from Table 9. As data indicated, the ICC staining method using the anti-HPV E7 antibody described in some embodiments provides ICC assay sensitivity of 93% for ≥CIN2 with specificity of 74%. These data suggest that this assay, with 57% of PPV and 97% of NPV, can be useful to detect HPV proteins for screening of cervical cancer from general population along with routine Pap smear staining.

TABLE 10

Summary of the ICC staining results using a mouse monoclonal anti-HPV E7 antibody on cervical scrape samples in a liquid based solution.

|  | CIN ≥ 2 | CIN ≤ 1 | | |
|---|---|---|---|---|
| HPV E7 ICC positive | 26 | 20 | 57% | PPV |
| HPV E7 ICC negative | 2 | 57 | 97% | NPV |
| Sensitivity | 93% | | | |
| Specificity | | 74% | | |

To test if the HPV ICC assay described in some embodiments is suitable for early stage of cervical cancer screening, Pap normal samples were used to compare the HPV ICC assay with HPV DNA test. As data shown in Table 11, all Pap smear normal samples tested (44 out of 44) stain negatively using anti-HPV antibody. These data indicate that the ICC staining assay described in some embodiments is very specific. Comparing to HPV DNA test results on the same samples, 16% (7 out of 44) of the Pap smear normal samples show positively on HPV DNA test. The high-grade HPV DNA test used in this study was HC2, the only FDA approved HPV DNA test. For those 7 samples that are HPV DNA positive but Pap normal and HPV ICC negative, they are either the possible false positives of the HPV DNA assay, or due to the fact that the DNA can be detected for the HPV infection but there is no expression of HPV oncogenic proteins. These data indicate that HPV ICC assay described herein provides better positive predictive value compared to HPV DNA test. Thus, the HPV ICC assay provides better clinical relevance for screening of cervical cancer.

TABLE 11

Comparison of ICC staining and HPV DNA test (HC2) on Pap normal samples with various anti-HPV antibodies using Pap test as gold standard.

| Pap smear normal | HPV ICC positive | HPV ICC negative |
|---|---|---|
| high-grade HPV DNA positive | 0 | 7 |
| high-grade HPV DNA negative | 0 | 37 |

Total 44 cases of normal Pap smear from general screening population. Samples were collected in Liquid Prep solution.

Detailed Example 3

Immunohistochemistry Assay (IHC)

Some embodiments are directed to a method of screening a human subject of Papillomavirus infection includes providing a thin section containing one or more kinds of tissue cells from a clinical tissue sample of the human subject, applying the thin section on a slide, conducting one or more immunohistochemical assays on the slide containing the thin section of the clinical tissue sample, staining the thin layer of human cells using one or more antibodies generated against one or more purified recombinant Papillomavirus proteins, wherein at least one antibody is capable of recognizing a Papillomavirus early protein, and detecting in situ one or more proteins from one or more Papillomavirus types present in the thin section of the clinical tissue sample on the slide.

Sample preparation: Paraffin tissues blocks sectioned into 4 microns were placed on slide and baked at 60° C. overnight. Deparaffin/hydrate sections were unmasked followed by standard IHC staining procedures. Purified monoclonal antibody against HPV proteins were diluted to use as the primary antibody. Staining procedure is followed by secondary antibody solution, washing, followed by appropriate substrate reagent to each section. As soon as the sections develop, immerse slides in $dH_2O$, counterstain sections with hematoxylin, dehydrate and mount coverslips. The cervical tissues containing, for examples, LSIL: Low grade of Squamous Intraepithelial Lesion. HSIL: High grade of Squamous Intraepithelial Lesion. CIN 1: Cervical Intraepithelial Neoplasia, mild cell abnormalities. CIN2: Cervical Intraepithelial Neoplasia with lesions appearing more aggressive. CIN3: Cervical Intraepithelial Neoplasia with aggressive form of dysplasia. Invasive cancer like squamous cell carcinoma (SCC) and adenocarcinoma (ADC). For the dysplasia cells identified, HPV IHC staining may provide additional information for status of HPV infection and/or expression of HPV oncoproteins. Therefore, HPV IHC staining assay is very useful as a confirmatory test. In addition, overexpression of HPV E6 and E7 oncoproteins in various stage of cervical dysplasia may indicate progression of CIN and/or cervical cancer development.

Once the tissues are processed and fixed, the Immunohistochemistry (IHC) assay is performed by boiling the tissues on the slide with antigen retrieval buffer for a period of time. The slides were then cool down to room temperature, blocked with pre-antibody blocking solution for a period of time, then incubated with the HPV antibodies. The slides were then washed 3 to 5 times with PBS or $H_2O$, or other solution to get rid of any unbound HPV antibody. Then the slides were incubated with the secondary antibody, for example, anti-mouse IgG HRP, followed by appropriate substrate for detection. As an example, DAB is oxidized in the presence of peroxidase and hydrogen peroxide resulting in the deposition of a brown, alcohol-insoluble precipitate at the site of enzymatic activity. The precipitate may range in color from a light golden brown to dark golden brown depending upon the amount of enzyme present. The golden brown precipitate viewed under a microscope indicates the specific binding of HPV antibodies with HPV proteins present in the cells. The assay can be performed at room temperature or higher temperature to accelerate the binding reaction. This IHC assay can be performed manually, or operated by IHC automation, thus provides a powerful tool to detect HPV infection and HPV oncoproteins in situ localization in the epithelium cells from cervical tissues Some embodiments are directed to IHC assay comprising the detection of HPV E6, E7 and p16 proteins in cervical cancer tissues. An example of procedures to demonstrate immunohistochemistry (IHC) staining assays: A) Tissue array preparation: Tissue slides were sectioned from paraffin-embedded tissue blocks. Each tissue microarray contains 22 cervical squamous cell carcinomas or adenocarcinomas and 3 normal epithelia as negative controls. 87 cores of paraffin-embedded blocks were grouped and sectioned to four micrometer tissue slides. Each tissue microarray contains 3 replicate cores of total up to 26 cervical squamous cell carcinomas or adenocarcinomas and 3 replicate cores of total 3 normal samples as negative control. Total of 220 cases were arrayed onto total of 9 slides. B) Immunohistochemical method: The 9 tissue microarrays with total of 220 cases of cervical cancer tissues were tested for E6, E7 and p16 IHC. Recombinant proteins of full length HPV type 16 E6, E7 and HPV type 18 E6, E7 were produced and purified to immunize rabbits and mice for polyclonal antibody production and monoclonal antibody described in some embodiments. Using such antibodies, and the clone E6H4 to $p16^{INK4a}$ human protein, IHC protocols were developed to stain tissue microarray. The study included 3 samples from each tumor subject. To interpret the results, For E6 and E7 proteins, if for a given sample at least 10% of tumor cells are stained and the intensity is score 1, 2 or 3; it is assigned that sample having a positive E6/E7 expression. For p16$^{INK4a}$ the rating of "positive" is assigned if specimen shows a continuous staining of cells (i.e., a diffuse staining pattern), and the rating of "negative" is assigned if specimen shows either a negative staining reaction or a staining of isolated cells or small cell clusters (i.e., focal staining pattern). C) DNA typing: HPV DNA typing of each case was identified by PCR SPF10-LiPA 25 (ver. 1: produced at Labo Biomedical Pdts., Rijswijk, The Netherlands), a reverse hybridization technique that detects 25 high and low-risk HPV types. The assay was performed in the HPV Laboratory (Catalan Institute of Oncology, Barcelona, Spain).

Figure 8A:
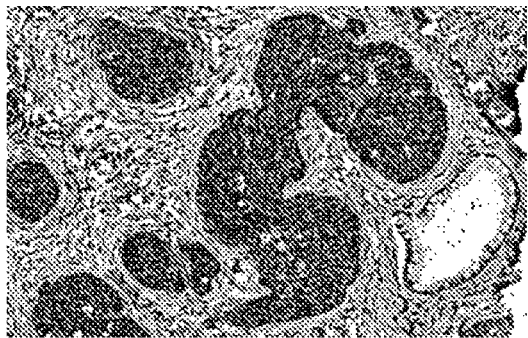
FIG. 8A-8B: Images of IHC using anti-E6 antibody on cervical cancer tissue and its adjacent normal tissue.
Figure 8C:
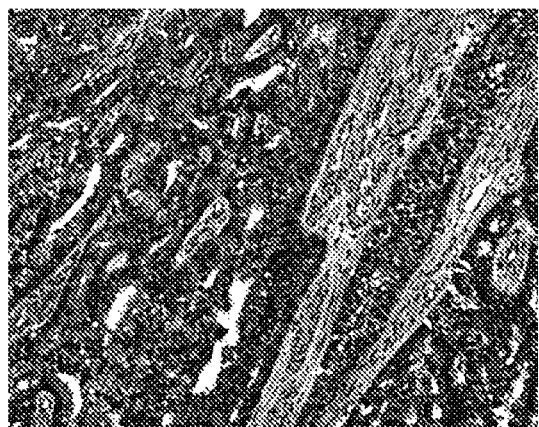
FIG. 8C-8D: Images of IHC using anti-E7 antibody on cervical cancer and its adjacent normal tissue.
Figure 8B:
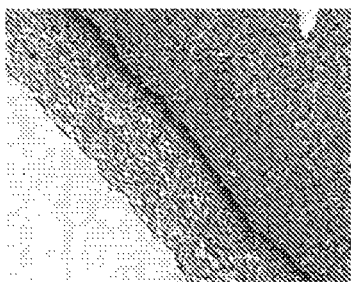
Figure 8D:
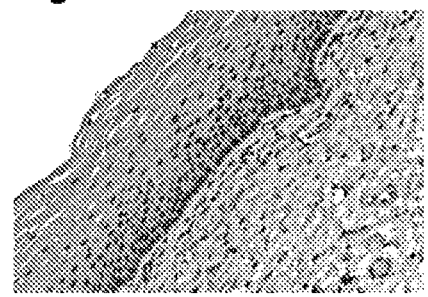
Figure 9A:
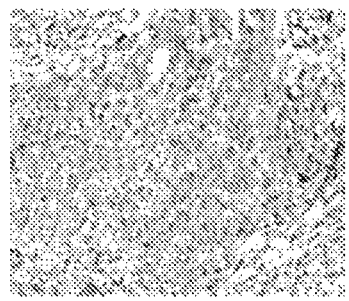
FIG. 9A-9C: Images of IHC with anti-E6 antibody on cervical cancer samples: positive 10× (left), positive 20× (middle), negative 20× (right).
Figure 9B:
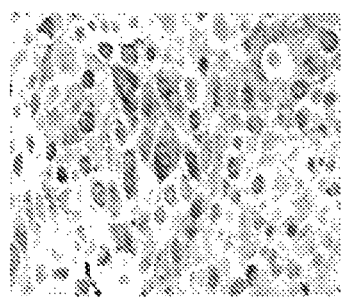
Figure 9C:
Figure 9D:
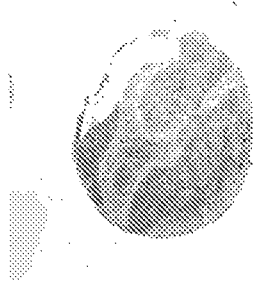
FIG. 9D-9F: Images of IHC with anti-E7 antibody on cervical cancer samples: positive 10× (left), positive 20×(middle), positive 40× (right).
Figure 9E:
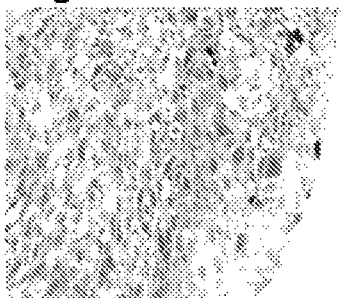
Figure 9F:
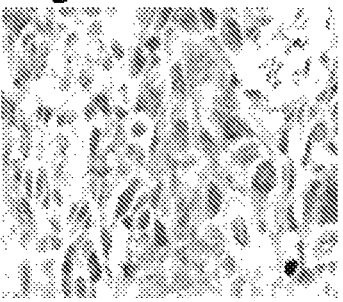
Figure 9G:
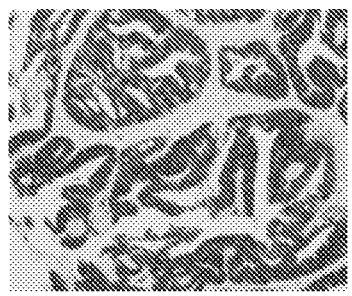
FIG. 9G-9I: Images of IHC with p16$^{INK4a}$ antibody on cervical cancer samples: positive 10× (left), positive 20× (middle), negative 20× (right).
Figure 9H:
Figure 9I:
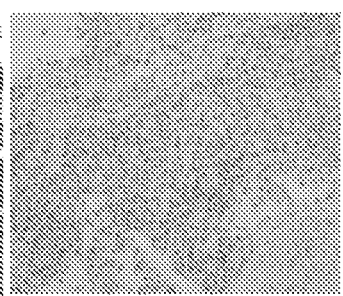

As an example, FIG. 8A-8B show images of IHC using anti-E6 antibody on cervical cancer tissue and its adjacent normal tissue. FIG. 8C-8D shows Images of IHC using anti-E7 antibody on cervical cancer and its adjacent normal tissue. The results show positive staining on cervical cancer samples, and negative staining on adjacent normal tissue. As another example, FIG. 9 shows images of IHC on cervical cancer samples with different magnifications. FIG. 9A-C, IHC with anti-E6 antibody: positive 10× (A), positive 20× (B), negative 20× (C). FIG. 9D-F, IHC with anti-E7 antibody: positive 10× (D), positive 20× (E), positive 40× (F). FIG. 9G-I, IHC with p16$^{INK4a}$ antibody: positive 10× (G), positive 20× (H), negative 20× (I).

Results of IHC staining were scored by certified pathologist to give intensity of score 0-3 and the percentage of tumor cells stained. To interpret the results, a positive result was assigned as E6/E7 in that samples with at least 10% of tumor cells stained and intensity score of 1, 2 or 3. For p16$^{INK4a}$ the rating of "positive" is assigned if specimen shows a continuous staining of cells (i.e., a diffuse staining pattern), and the rating of "negative" is assigned if specimen shows either a negative staining reaction or a staining of isolated cells or small cell clusters (i.e., focal staining pattern). Data were analyzed to obtain the assay sensitivity and specificity compared to PCR and IHC staining by p16. Statistical significance was also analyzed.

Table 12 shows the assay sensitivity of IHC using anti-E6, E7, and p16 antibody. The results demonstrate that Assay sensitivity of HPV IHC using anti-E6 antibody is about 92.1% (187 out of 203). Assay sensitivity of HPV IHC using anti-E7 antibody is about 76.2% (154 out of 202). Assay sensitivity of HPV IHC using anti-p16 antibody is about 91.3% (190 out of 208).

TABLE 12

Summary of the results for IHC assays using single markers.

| | anti-E6 (N° cases) | anti E7 (N° of cases) | p16$^{INK4a}$ (N° of cases) |
|---|---|---|---|
| Positive | 187 | 154 | 190 |
| Negative | 16 | 48 | 18 |
| Total | 203 | 202 | 208 |
| Sensitivity | 92.1% (187/203) | 76.2% (154/202) | 91.3% (190/208) |
| Specificity | 100% | 100% | 100% |

The correlation of E6, E7 and p16 proteins expression is shown in Tables 13-15. In Table 13, total 203 samples were analyzed on IHC assays using either E6 or p16. Among the 187 of IHC E6 positive samples, 170 samples show positive on p16 IHC. Among the 16 of IHC E6 negative samples, 15 samples show positive on p16 IHC. Among the 185 of IHC p16 positive samples, 170 samples show positive on E6 IHC. Among the 18 of IHC p16 negative samples, 17 samples show positive on E6 IHC. There is only 1 sample that is negative on both E6 IHC and p16 IHC. Thus, combined p16 and E6 IHC assay provides 99.5% of assay sensitivity (202 out of 203 samples are p16 or E6 IHC positive, Table 5).

TABLE 13

Correlation of the results for E6 and p16 protein expression in IHC assay.

| | E6 positive | E6 negative | Total |
|---|---|---|---|
| p16 positive | 170 | 15 | 185 |
| p16 negative | 17 | 1 | 18 |
| | 187 | 16 | 203 |

In Table 14, total 202 samples were analyzed on IHC assays using either E6 or E7. Among the 186 of IHC E6 positive samples, 153 samples show positive on E7 IHC. Among the 16 of IHC E6 negative samples, 1 samples show positive on E7 IHC. Among the 154 of IHC E7 positive samples, 153 samples show positive on E6 IHC. Among the 48 of IHC E7 negative samples, 33 samples show positive on E6 IHC. There are 15 samples that are negative on both E6 IHC and E7 IHC. Thus, combined E6 and E7 IHC assay provides 92.5% of assay sensitivity (187 out of 202 samples are p16 or E6 IHC positive, Table 5).

TABLE 14

Correlation of the results for E6 and E7 protein expression in IHC assay.

| | E6 positive | E6 negative | Total |
|---|---|---|---|
| E7 positive | 153 | 1 | 154 |
| E7 negative | 33 | 15 | 48 |
| | 186 | 16 | 202 |

In Table 15, total 202 samples were analyzed on IHC assays using either E7 or p16. Among the 154 of IHC E7 positive samples, 142 samples show positive on p16 IHC. Among the 48 of IHC E7 negative samples, 42 samples show positive on p16 IHC. Among the 184 of IHC p16 positive samples, 142 samples show positive on E7 IHC. Among the 18 of IHC p16 negative samples, 12 samples show positive on E7 IHC. There are 6 samples that are negative on both E7 IHC and p16 IHC. Combined E7 and p16 IHC assay provides 97.0% of assay sensitivity (196 out of 202 samples are p16 or E7 IHC positive, Table 5).

TABLE 15

Correlation of the results for E7 and p16 protein expression in IHC assay.

| | E7 positive | E7 negative | Total |
|---|---|---|---|
| p16 positive | 142 | 42 | 184 |
| p16 negative | 12 | 6 | 18 |
| | 154 | 48 | 202 |

HPV E6 and E7 oncogenic proteins expressed in the tumor cells of cervical cancer can be detected in major portion of samples tested by IHC assay using the specific anti-E6 and anti-E7 antibody. These results strengthen the etiology and molecular mechanisms of HPV oncoproteins play in most cases of cervical cancer. The study results further demonstrate the functional inactivation of p53 and pRb proteins by dysregulated viral E6 and E7 oncoproteins expression respectively, resulting in overexpression of p16$^{INK4a}$. In this study, as shown in Table 12, the sensitivity of E6 antibody (92%) is comparable to the sensitivity of p16$^{INK4a}$ antibody (91%). Though the sensitivity of E7 antibody is relatively low (76%), the assay could be further optimized. For the samples with IHC results shown discrepancy in expression of HPV E6/E7 oncoproteins and p16 cellular protein in cervical cancer, it is possible that various pathways are involved in cancer development for those individual cases. Thus, both HPV oncoproteins and cellular proteins play important roles in carcinogenesis to serve as biomarkers for diagnosis of HPV associated cancers. Studies using more biomarkers in different HPV associated cancers will help to provide personalized medicine.

Although p16 is accepted marker in current practice, it is not perfect for all the cases tested. Table 13 shows that among the 18 of p16 IHC negative samples, 17 samples show positive on IHC using anti-E6 antibody. Table 15 shows that among the 18 of p16 IHC negative samples, 12 samples show positive on IHC using anti-E7 antibody. Thus, as shown in Table 16, IHC assays using combined markers p16+E6 provide 99.5% of assay sensitivity as compared to 91.3% when using p16 alone. IHC assays using combined markers p16+E7 provide 97.0% of assay sensitivity as compared to 91.3% when using p16 alone. In either case the IHC assays using a combination of markers with cellular proteins such as p16 and oncoproteins such as E6 or E7 provide increased assay sensitivity in detecting cervical cancer.

TABLE 16

Summary of sensitivity for IHC assays using single or combined markers.

| IHC assay type | No. of Samples | No. of Positives | Sensitivity |
|---|---|---|---|
| E6 | 203 | 187 | 92.1% |
| E7 | 202 | 154 | 76.2% |
| p16 | 208 | 190 | 91.3% |
| E6 + p16 | 203 | 202 | 99.5% |
| E6 + E7 | 202 | 187 | 92.5% |
| E7 + p16 | 202 | 196 | 97.0% |
| E6 + E7 + p16 | 202 | 201 | 99.5% |

IHC assays using single marker E7 provides a relatively low sensitivity, 76.2% compared to that using E6 or p16, as shown in Table 5. Assays using combined markers may increase the sensitivity. The combined results from Table 15 and Table 16 show that among the 48 cases of E7 IHC negative samples, 33 samples are E6 IHC positive (Table 15), and among the 48 cases of E7 IHC negative samples, 42 samples are p16 IHC positive (Table 16). In addition, 28 of those samples are positive on both E6 and p16 (data not shown). This leaves 47 E7 IHC negative cases are either E6 IHC positive or p16 IHC positive, and only 1 sample is negative in E6, E7, or p16 IHC. Thus, as shown in Table 16, although the sensitivity for E7 IHC is relatively low as 76.2%, the sensitivity can be increased to 92.5 when using combined markers E6+E7, and increased to 97.0% when using combined markers E7+p16. Further more, if all three markers are used, the sensitivity of the IHC assay can be further increased to 99.5%. In either case the IHC assays using a combination of markers with cellular proteins such as p16, or with some other oncoproteins such as E6 or E7 provide increased assay sensitivity.

IHC assays using single marker E6 provides a sensitivity of 92.1%, as shown in Table 16. Assays using combined markers are shown to have increased the sensitivity. Table 13 shows that among the 16 of E6 IHC negative samples, 15 samples show positive on IHC using anti-p16 antibody. Table 3 shows that among the 16 of E6 IHC negative samples, 1 sample show positive on IHC using anti-E7 antibody. Thus, as shown in Table 16, IHC assays using combined markers E6+p16 provide 99.5% of assay sensitivity as compared to 92.1% when using E6 alone. IHC assays using combined markers E6+E7 provide 92.5% of assay sensitivity as compared to 92.1% when using E6 alone. In either case the IHC assays using a combination of markers, either with cellular proteins such as p16, or with some other oncoproteins such as E6 or E7 provide increased assay sensitivity.

These data suggest that more than one biomarker are required in order to detect 99.5% (close to 100%) of cervical cancer.

Table 17 shows a comparison of the results from the HPV DNA typing method and the E6 IHC method. Total 202 samples were tested. Among these, 163 samples, 162 positives and 1 negative, show assay agreement between E6 IHC and HPV DNA methods (81%, 163/202). 92% (162/177) of HPV DNA positive is E6 IHC positive. 87% (162/186) of E6 IHC positive is HPV DNA positive. 186 cases are E6 IHC positive and only 177 cases are HPV DNA typing positive. The E6 IHC method thus provides a better assay sensitivity (92%, 186 out of 202) compared to that of the HPV DNA typing method (87.6%, 177 out of 202) in cervical biopsy tissues. For the 16 samples that are E6 IHC negative, 15 samples are HPV DNA typing positive. For the 25 samples that are HPV DAN typing negative, 24 samples are E6 IHC positive. It leaves only 1 sample out of 202 samples tested that is both E6 IHC and HPV DNA typing negative. Thus, when combining both E6 IHC and HPV DNA methods together, the assay sensitivity increases to 99.5% (201/202). The results indicate that E6 IHC is superior providing simple, robust, and better sensitivity from one single marker (92% for E6 IHC vs. 87.6% for HPV DNA typing). Combined methods further increase the assay sensitivity to 99.5%.

TABLE 17

Comparison of HPV DNA typing and E6 IHC methods.

| | HPV DNA typing | | |
|---|---|---|---|
| E6, IHC | Positive | Negative | N° Total |
| Positives | 162 | 24 | 186 |
| Negatives | 15 | 1 | 16 |
| N° Total | 177 | 25 | 202 |

All cases tested in this study are cervical cancers confirmed by histology. Table 18 shows the cancer type distribution among the 177 HPV DNA cervical cancer cases. 84% (149/177) of the cases are squamous cell carcinoma, 11% (20/177) are adenocarcinoma, 3.4% (6/177) are adenosquamous and 1.1% (2/177) is other cancer types. For the samples with E6 overexpression (E6+), 92.6% (138/149) of squamous cell carcinoma, 80% (16/20) of adenocarcinoma, and 100% (6/6) of adenosquamous are E6 IHC positive.

TABLE 18

Cancer characterization (Histology diagnosis) on E6 IHC and HPV DNA tested samples

|  | Squamous cell carcinoma | | Adeno-carcinoma | | Adeno-squamous | | Other | | Total |
|---|---|---|---|---|---|---|---|---|---|
| E6+/HPV DNA+ | 138 | 92.6% | 16 | 80% | 6 | 100% | 2 | 100% | 162 |
| E6−/HPV DNA+ | 11 | 7.4% | 4 | 20% | 0 | 0 | 0 | 0 | 15 |
| Total | 149 | 100% | 20 | 100% | 6 | 100% | 2 | 100% | 177 |

To summarize: HPV E6 and E7 oncogenic proteins expressed in the tumor cells of cervical cancer can be detected in major portion of the samples tested by IHC assay using the specific anti-E6 and anti-E7 antibody. These results strengthen the etiology and molecular mechanisms of HPV oncoproteins play in most cases of cervical cancer. The study results further demonstrate the functional inactivation of p53 and pRb proteins by dysregulated viral E6 and E7 oncoproteins expression respectively, resulting in overexpression of p16$^{INK4a}$. In this study, the sensitivity of E6 antibody (92%) is similar to the sensitivity of p16$^{INK4a}$ antibody (91%). However, combined E6 and p16 IHC further increases the sensitivity to be 99.5%.

Compared to HPV DNA typing method for cervical cancer tissues, E6 IHC is superior providing higher sensitivity with simple and robust assay. Combined IHC and HPV DNA typing method further increases the assay sensitivity to 99.5%. For the samples shown discrepancy expression of HPV E6/E7 oncoproteins and p16 cellular protein in cervical cancer, it is possible various pathways involved in cancer development for those individual cases. Data suggest multiple biomarkers (i.e. combined E6 and p16 IHC assay) help to obtain higher sensitivity of cervical cancer compared to using single biomarkers, either E6 or p16 along.

In high grade CIN lesions, E6 and E7 are strongly expressed in host basal epithelial cells and interfere substantially with cell cycle control of these replication competent host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High level of HPV E7 proteins inactivates pRB and leads to disruption of E2F-Rb binding. Usually, binding of pRB to E2F blocks E2F driven cell cycle activation. In replicating cells, E2F is regulated by phosphorylation of RB. RB phosphorylation is normally mediated by cyclin dependent kinases (CDK4, CDK6) that are controlled by several kinase inhibitors (INKs).

As a result of the loss of Rb/E2F repression and the strong activation by free E2F, the expression of a host cell protein, p16$^{INK4a}$, is strongly overexpressed. In addition, S-phase genes are continuously activated since the p16$^{INK4a}$ mediated repression of Cdk4/6 has no downstream effect on pRb host cell protein. Since E7-dependent E2F release is not mediated by phosphorylation of pRb, the counter-regulatory p16$^{INK4a}$ expression has no effect on the activated cell cycle. Under physiological conditions p16$^{INK4a}$ is expressed when cells undergo a genomic stress situation such as substantial shortening of telomeres in ageing tissues. Also, apoptosis is abrogated by HPV E6 mediated degradation of p53. The overexpression of the cyclin dependent kinase (CDK) inhibitor, p16$^{INK4a}$, is a direct consequence of deregulated HPV oncogene expression.

In addition, host cell proteins that are important for proliferation and host cell genome replication may be overexpressed as a result of HPV infection. These host cell proteins include but not limited to, ki67 (MIB-1), MYC cellular oncogene, Cyclin proteins (e.g., cyclin A, B, E, etc.), CDKN2A/p16$^{INK4a}$, telomerase (e.g., TERC), replication complex proteins (e.g., MCM5, CDC6, topoisomerase II alpha (TOP2A), MCM2, minichromosome maintenance proteins 2, 4, and 5, etc.).

As a result, the immunological assays for detection of HPV proteins, such as E6, E7, L1, etc., or immune response thereof due to HPV infection can be performed in high throughput ELISA screening assays, rapid immunological screening assays, and additional multiplexed protein chip assays, etc., and combinations thereof. Embodiments of the invention provides various polyclonal and monoclonal antibodies for HPV proteins to be used in one or more assays, including an antibody, antigen, or immunocomplex assays developed to detect HPV viral proteins encoded by early genes (e.g., E6 and E7) and late genes (e.g., L1). In addition, the developed antibody, antigen, or immunocomplex assays for E6, E7, L1, protein or their antibodies thereof in one format, for example, a microplate format, can be adapted into a one-step immunochromatographic assay for the direct measurement of E6, E7, L1 proteins or antibodies induced by HPV infection. The one or more immunological assays as provided herein aims to employ user friendly procedures with simple instrument or no additional instrument to perform in a short period of time. Comparison of the results of the various immunological assays, nucleic acid hybridization assays with cytological and histological data for the human subjects as well as demographic information serve to validate the correlation and accuracy in diagnosing HPV infection and/or cervical cancer.

Early diagnosis of dysplasia cells is important for successful prevention and treatment of cervical cancer. Strategies to prevent cervical cancer requires improved HPV testing/screening to cover a broad range of the worldwide population in addition to closely follow-up those subjects with past or present HPV infection and/or pre-cancerous lesions. Importantly, it is known that infection in women for 12-15 years with HPV is required before invasive cancer to develop. It is thus important to be able to assay HPV associated biomarkers for high grade dysplasia or precancerous cells as described herein to pre-screen women at an early stage, and to identify those underlying high-grade CIN that can benefit medical intervention and prevent cervical cancer development, rather than having to rely on chemotherapy or radiation to treat cancer malignancy if diagnosed at a later stage.

To analyze the HPV IHC results from each subject of invasive cancer, Table 19 shows data from 24 cases of invasive cancer samples with IHC score for staining of cytoplasm (C), and nucleus (N) using C, or N followed by the % of staining using the anti-HPV E7 antibody. Additional anti-HPV antibodies including another anti-E7 antibody, Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 19. Results of HPV DNA typing were also shown on the table for its corresponding case.

As shown in Table 19, both nucleus and cytoplasmic staining are found in all the subjects of tumor cells from SCC and ADE stained by the anti-E7 antibody. However, there is more staining (percentage stained) found in the cytoplasm of tumor cells comparing the staining of nuclear of tumor cells. The detection of HPV E7 protein in its adjacent normal epithelium cells was only found in nucleus, but not found in the cytoplasm of the epithelial cells. The staining of cytoplasm appears most distinguishable in tumor cells compared to its corresponding normal adjacent cells. These data demonstrate expression of HPV E7 proteins was detected in the cytoplasm and nuclear of tumor cells of SCC and ADE tissues. The localization of the E7 proteins expressed in the cytoplasm of tumor cells, but not in the normal epithelium or stroma cells appears tumor specific. HPV E7 proteins present in the nucleus of normal adjacent epithelium and tumor cells detected by the anti-HPV E7 antibody indicate HPV infection with oncoproteins expression. Similar staining pattern was also found when used other anti-HPV antibodies as shown in Table 19. Data indicate that the HPV IHC assay as described herein can detect HPV early gene such as E6, E7, and late gene such as L1 proteins present in the tumor cells of cervical cancer tissues.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-33, HPV-45, etc., which are cancer-related HPV types (high risk HPV types). The single anti-E7 monoclonal antibody can also detect HPV infection by two or more HPV types, such as the combination of HPV 11, HPV-16, HPV-18, HPV-52, HPV-58, HPV-51, HPV-59, etc., which include high risk, low risk, and non-oncogenic α-papillomaviruses. However, infection by multiple HPV types contains at least one type is high-risk HPV type. These data indicate that the anti-E7 antibody described in this invention is non-type specific, thus provides a powerful tool to detect HPV E7 proteins from most common high-risk HPV types in the cervical cancer.

To analyze the HPV IHC results from each subject of CIN3, Table 20 shows data from 30 cases of CIN 3 samples with IHC score for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 19. Results of HPV DNA typing were also shown on the table for its corresponding case.

As shown in Table 20, nucleus staining are found in the dysplasia cells of all the CIN3 samples tested while only certain proportion of cases found staining of cytoplasm by the anti-E7 antibody. The results indicate that there is more staining found in the cytoplasm than in the nuclear of dysplasia cells. As shown previously in invasive cancer tissues, HPV E7 protein in its adjacent normal epithelium cells was only found in nucleus, but not found in the cytoplasm of the epithelial cells. The staining of cytoplasm appears most distinguishable in dysplasia cells compared to its corresponding normal adjacent cells. The localization of the E7 proteins expressed in the cytoplasm of dysplasia cells, but not in the normal epithelium or stroma cells appears HSIL specific. These data demonstrate expression of HPV E7 proteins can be detected in the cytoplasm and nuclear of dysplasia cells of CIN3 tissues. HPV E7 proteins present in the nucleus of normal adjacent epithelium and dysplasia cells detected by the anti-HPV E7 antibody indicate HPV infection with oncoproteins expression. For the cases with high level expression of HPV E7 proteins detected in the cytoplasm of dysplasia cells, it may suggest specific indication of dysplasia progression. Similar staining pattern was also found when used other anti-HPV antibodies as shown in Table 20. Data indicate that the HPV IHC assay as described herein can detect HPV early gene such as E6, E7, and late gene such as L1 proteins present in the dysplasia cells of CIN3.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-31, HPV-33, HPV-39, HPV-58, etc., which are cancer-related HPV types (high risk HPV types). The single anti-E7 monoclonal antibody can also detect HPV infection by two or more HPV types, such as the combination of HPV-16, HPV-18, HPV-33, HPV-39, HPV-52, HPV-58, etc., which include most common high-risk HPV. These data indicate that the anti-E7 antibody described in this invention is non-type specific, thus provides a powerful tool to detect HPV E7 proteins from most common high-risk HPV types in the CIN3 tissues.

TABLE 19

IHC staining results (stained %) and HPV DNA typing for 12 SCC biopsy samples and 12 ADC biopsy samples (C: Cytoplasmic; N: Nucleus; Dys: dysplasia or tumor cells).

| Sample # | HPV type | Anti-E7 | | | | Another anti-E7 Dys (%) | Anti-E6 Dys (%) | Another Anti-anti-E6 Dys. (%) | L1 Dys. (%) |
|---|---|---|---|---|---|---|---|---|---|
| | | Dys (% stained) | | Normal epith. (% stained) | | | | | |
| | | C | N | C | N | C | C | C | C |
| 5CC-1 | 18 | 85 | 85 | 0 | 20 | 12.5 | 10 | 70 | 55 |
| SCC-2 | 16, 52 | 90 | 85 | 0 | 25 | 15 | 15 | 10 | 55 |
| SCC-3 | 16 | 60 | 65 | 0 | 40 | 5 | 0 | 10 | 20 |
| SCC-4 | 16 | 92 | 50 | 0 | 40 | 5 | 0 | 10 | 85 |
| SCC-5 | 16, 52, 58 | 92 | 55 | 0 | 50 | 20 | 5 | 15 | 88 |
| SCC-6 | 18, 52, 58 | 90 | 60 | | | 25 | 18 | 10 | 70 |
| SCC-7 | 16, 52 | 92 | 75 | 0 | 30 | 30 | 5 | 10 | 20 |
| SCC-8 | 16, 58 | 10 | 10 | 0 | 5 | 0 | 0 | 10 | 50 |
| SCC-9 | no DNA | 95 | 60 | 0 | 40 | 25 | 8 | 15 | 8 |
| SCC-10 | 18 | 92 | 65 | 0 | 60 | 45 | 25 | 20 | 65 |
| SCC-11 | 16, 58 | | | 0 | 80 | 5 | | 0 | 0 |
| SCC-12 | 33 | 95 | 90 | 0 | 0 | 30 | 1 | 20 | 55 |
| ADE-1 | 16, 18 | 30 | 20 | 0 | 50 | 15 | 25 | 20 | 82 |
| ADE-2 | no DNA | 62 | 40 | 0 | 30 | 35 | 70 | 35 | 78 |
| ADE-3 | 16 | 20 | 30 | 0 | 20 | 35 | 55 | | 60 |
| ADE-4 | 16, 18 | 80 | 80 | 0 | 0 | 10 | 5 | 0 | 90 |
| ADE-5 | 51, 52 | 95 | 80 | 0 | 50 | 10 | 70 | 15 | 92 |
| ADE-6 | 11, 16, 52 | | | 0 | 40 | 5 | 0 | 0 | 15 |
| ADE-7 | 18 | 50 | 40 | 0 | 60 | 25 | 20 | 20 | 75 |
| ADE-8 | 18 | 85 | 60 | 0 | 40 | 15 | 50 | 15 | 82 |
| ADE-9 | 45 | 82 | 55 | 0 | 30 | 30 | 2 | 20 | 40 |
| ADE-10 | 18 | 15 | 10 | 0 | 40 | 15 | 15 | 5 | 70 |
| ADE-11 | 18, 59 | 70 | 0 | 0 | 50 | 15 | 8 | 5 | 65 |
| ADE-12 | 18 | | | | | | | | 30 |

TABLE 20

IHC staining results (stained % and score; 0-3) and HPV DNA typing of 30 CIN 3 samples (M: Membrane; C: Cytoplasmic; N: Nucleus; Dys: Dysplasia).

| ID # | HPV type | anti-E7 | | | | | | Anti-E6 Dys. (%) Cyto | Another anti-E7 Dys. (%) Cyto | Anti-L1 Dys. (%) Cyto |
|---|---|---|---|---|---|---|---|---|---|---|
| | | Dysplasia (% stained) | | | Normal epithelium (% stained) | | | | | |
| | | M | C | N | M | C | N | | | |
| 31 | 33 | 0 | 80 | 80 | 0 | 0 | 50 | 70 | 40 | 80 |
| 32 | 16 | 0 | 80 | 80 | | 60 | 0 | 0 | | 5 |

TABLE 20-continued

IHC staining results (stained % and score; 0-3) and HPV DNA typing of 30 CIN 3 samples (M: Membrane; C: Cytoplasmic; N: Nuceus; Dys: Dysplasia).

| | | anti-E7 | | | | | | Anti-E6 Dys. (%) | Anti- Another anti-E7 Dys. (%) | Anti- L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 33 | 16, 58 | | | | 0 | 0 | 60 | | | |
| 34 | 31 | 0 | 50 | 70 | 0 | 0 | 50 | 0 | 0 | 10 |
| 35 | 16, 39 | 0 | 70 | 90 | 0 | 0 | 40 | 0 | 10 | 30 |
| 36 | 31 | 0 | 70 | 60 | 0 | 0 | 50 | 0 | 20 | 20 |
| 37 | 39 | 0 | 0 | 40 | 0 | 0 | 0 | 0 | 0 | 0 |
| 38 | 16 | | | | 0 | 0 | 40 | | | |
| 39 | 16 | 0 | 60 | 70 | 0 | 0 | 40 | 0 | | 0 |
| 40 | 58 | 0 | 90 | 90 | 0 | 0 | 50 | 50 | 0 | 30 |
| 41 | 16 | 0 | 0 | 50 | 0 | 0 | 50 | 0 | 20 | 20 |
| 42 | 16 | 0 | 70 | 70 | 0 | 0 | 30 | 0 | 0 | |
| 43 | 33 | 0 | 0 | 90 | 0 | 0 | 50 | 0 | 0 | 5 |
| 44 | 52 | 0 | 70 | 80 | 0 | 0 | 50 | 70 | 10 | 50 |
| 45 | 51, 52 | 0 | 90 | 90 | 0 | 0 | 30 | 80 | 50 | 10 |
| 46 | 16 | 0 | 0 | 80 | 0 | 0 | 50 | 0 | 0 | 5 |
| 47 | 16 | 0 | 60 | 80 | 0 | 0 | 50 | 30 | 10 | 20 |
| 48 | 16, 58 | 0 | 0 | 80 | 0 | 0 | 50 | 0 | 0 | 10 |
| 49 | 31 | 0 | 80 | 60 | | | | 50 | 70 | 40 | 40 |
| 50 | 16 | 0 | 0 | 60 | 0 | 0 | 30 | 0 | 20 | 20 |
| 51 | 6 | | | | 0 | 0 | 20 | | 0 | |
| 52 | 16, 18, 33, 39 | 0 | 0 | 20 | 0 | 0 | 30 | 0 | 0 | 0 |
| 53 | 51, 52, 58 | 0 | 70 | 60 | 0 | 0 | | 60 | 60 | 40 |
| 54 | 16, 45 | 0 | 0 | 70 | 0 | 0 | 50 | 0 | 20 | 20 |
| 55 | 16 | 0 | 0 | 75 | 0 | 0 | 50 | 0 | 0 | 0 |
| 56 | 33, 52 | 0 | 0 | 80 | 0 | 0 | 50 | 0 | 0 | 10 |
| 57 | 16 | 0 | 0 | 50 | 0 | 0 | 40 | 0 | 0 | 0 |
| 58 | 33 | 0 | 0 | 80 | 0 | 0 | | 0 | 20 | 10 |
| 59 | 16 | 0 | 0 | 60 | 0 | 0 | 20 | 0 | 10 | 5 |
| 60 | 16, 52, 58 | 0 | 70 | 80 | 0 | 0 | 50 | 70 | 0 | 20 |

To analyze the HPV IHC results from each subject of CIN2, Table 21 shows data from 30 cases of CIN 2 samples with IHC score for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of dysplasia cells using other anti-HPV antibodies was also shown in Table 21. Results of HPV DNA typing were also shown in the table for its corresponding case.

TABLE 21

IHC staining results (stained % and score; 0-3) and HPV DNA typing for 30 biopsy samples (CIN2). (M: membrane; C: cytoplasmic; N: nucleus; Dys: dysplasia)

| | | Anti-E7 | | | | | | Anti-E6 Dys. (%) | another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 1 | 6 | 0 | 80 | 80 | 0 | 0 | 30 | 70 | 40 | 80 |
| 2 | 31 | 0 | 0 | 90 | | | | 0 | 40 | 0 |
| 3 | 52 | 0 | 25 | 50 | 0 | 0 | 70 | 0 | 20 | 20 |
| 4 | 16 | 0 | 0 | 40 | 0 | 0 | 30 | 0 | 5 | 0 |
| 5 | 58 | 0 | 0 | 50 | 0 | 0 | 10 | 0 | 0 | 0 |
| 6 | 52 | 0 | 80 | 70 | 0 | 0 | 50 | 0 | 5 | 0 |
| 7 | 53 | 0 | 0 | 80 | 0 | 0 | 30 | 0 | 10 | 10 |
| 8 | 52 | 0 | 50 | 90 | 0 | 0 | 20 | 60 | 10 | 20 |
| 9 | 31 | 0 | 80 | 80 | 0 | 0 | 50 | 70 | 20 | 40 |
| 10 | 16 | 0 | 50 | 80 | 0 | 0 | 50 | 60 | 20 | 10 |
| 11 | no DNA | 0 | 0 | 50 | 0 | 0 | 70 | 0 | 0 | 10 |
| 12 | 33 | 0 | 60 | 60 | 0 | 0 | 50 | 0 | 10 | 30 |
| 13 | no DNA | 0 | 70 | 80 | 0 | 0 | 70 | 0 | 20 | 10 |
| 14 | 52 | 0 | 0 | 70 | 0 | 0 | 70 | 0 | 30 | 20 |
| 15 | no DNA | 0 | 0 | 70 | 0 | 0 | 50 | 0 | 20 | 5 |
| 16 | 52 | 0 | 0 | 10 | 0 | 0 | 30 | 0 | 0 | 5 |
| 17 | 52 | 0 | 0 | 60 | 0 | 0 | 80 | 0 | 0 | 5 |
| 18 | 16 | 0 | 50 | 60 | 0 | 0 | 30 | 50 | 10 | 20 |
| 19 | 16 | 0 | 50 | 70 | | | | 0 | 10 | 20 |
| 20 | 52, 44 | 0 | 50 | 80 | 0 | 0 | 40 | 0 | 30 | 30 |
| 21 | 16 | 0 | 0 | 50 | 0 | 0 | 50 | 0 | 20 | 20 |
| 22 | 16, 18, 6 | 0 | 0 | 40 | 0 | 0 | 0 | 0 | 10 | 0 |
| 23 | 16, 31 | 0 | 0 | 30 | 0 | 0 | 60 | 0 | 0 | |
| 24 | 6 | 0 | 0 | 80 | 0 | 0 | 50 | 0 | 10 | 5 |
| 25 | 16 | 0 | 0 | 10 | 0 | 0 | 60 | 0 | 0 | 0 |
| 26 | 58 | 0 | 0 | 40 | 0 | 0 | 40 | 0 | 10 | 5 |
| 27 | 16, 39, 52 | | | | 0 | 0 | 70 | 0 | | |
| 28 | 6 | 0 | 0 | 50 | 0 | 0 | 70 | 0 | 10 | 5 |
| 29 | 16 | 0 | 0 | 70 | 0 | 0 | 5 | 0 | 10 | 20 |
| 30 | 66, 68, | 0 | 0 | 30 | 0 | 0 | 60 | 0 | 10 | 0 |

As shown in Table 21, nucleus staining are found in the dysplasia cells of all the CIN2 samples tested while only certain proportion of cases found staining of cytoplasm by the anti-E6 or anti-E7 antibody. The results indicate there is more staining of nucleus than cytoplasm of dysplasia cells found in CIN2 samples. As shown previously in SCC, ADC, and CIN3, HPV E7 protein in its adjacent normal epithelium cells was only found in nucleus, but not found in the cytoplasm of the epithelial cells. The staining of cytoplasm in CIN2 using anti-E6 antibody appears most distinguishable in dysplasia cells compared to its corresponding normal adjacent cells. The localization of the E6 proteins expressed in the cytoplasm of dysplasia cells, but not in the normal epithelium or stroma cells appears HSIL specific. These data demonstrate expression of HPV E6 proteins can be detected in the cytoplasm and nuclear of dysplasia cells of CIN2 tissues. For the cases with high level expression of HPV E6 proteins detected in the cytoplasm of dysplasia cells, it may suggest dysplasia progression. Similar staining pattern was also found when used other anti-HPV antibodies as shown in Table 21. The HPV IHC assay as described herein can be used to detect HPV early gene such as E6, E7, and late gene such as L1 proteins present in the dysplasia cells of CIN2.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least, HPV-16, HPV-18, HPV-31, HPV-52, HPV-58, etc, which are cancer-related HPV types (high risk HPV types) and HPV6, HPV 53 which are not high-risk HPV types. The single anti-E7 monoclonal antibody can also detect HPV infection by two or more HPV types, such as the combination of HPV6, HPV-16, HPV-18, HPV-31, HPV-39, HPV-44, HPV-52, HPV-58, HPV-66, HPV-68, etc., which include most common high-risk HPV as well as low risk HPV types. These data indicate that the anti-E7 antibody described in this invention is non-type specific, able to detect HPV E7 proteins from common high-risk HPV types as well as low risk types in the CIN2 tissues. It is possible that formation of dysplasia cells is resulted from expression of oncoproteins, rather than genotyping of HPV types. It explains regression may occur for those infection by high-risk types with no detection of oncoproteins in cytoplasm. Thus, the HPV IHC assay described herein provides additional clinical information, not only for detection of HPV infection, but also for indication of dysplasia progression.

Figure 10:
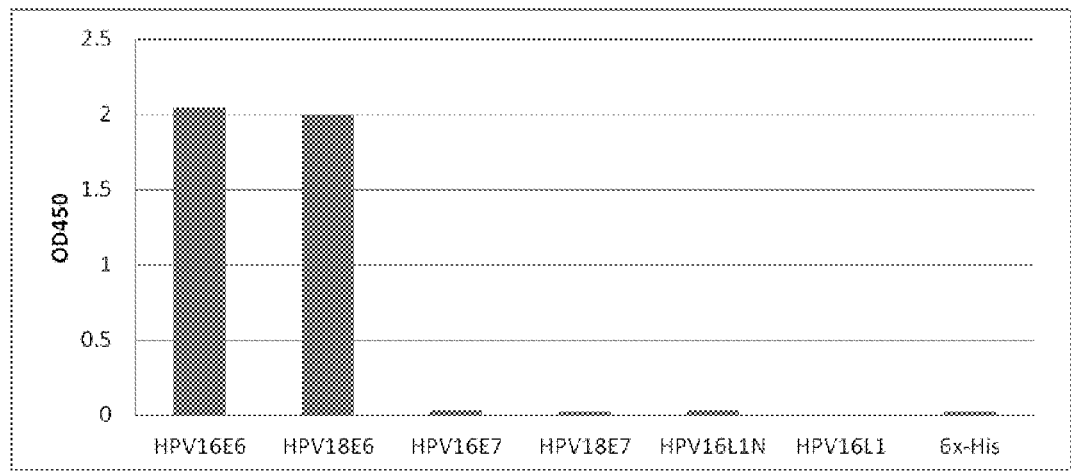
FIG. 10A shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

To demonstrate a monoclonal antibody capable of binding to two or more HPV viral proteins from different HPV type as described in this invention, a monoclonal antibody capable of reacting with recombinant E6 proteins of HPV 16 and HPV18 is also the obtained. FIG. 10A shows the specificity of a monoclonal antibody with common epitope capable of reacting with recombinant HPV16 E6 and HPV18E6 proteins on EIA. The recombinant protein coated on microtiter plate to be detected by the antibody described herein is in native form. These data demonstrate the monoclonal antibody reacts strongly to native form of recombinant HPV16 E6 and HPV18E6 proteins, but non-reactive to native form of recombinant HPV E7 nor HPV L1 proteins. These data indicate that this antibody contains HPV E6 common epitope capable of reacting with native form of recombinant HPV16 E6, and HPV18 E6 proteins.

Figure 11:
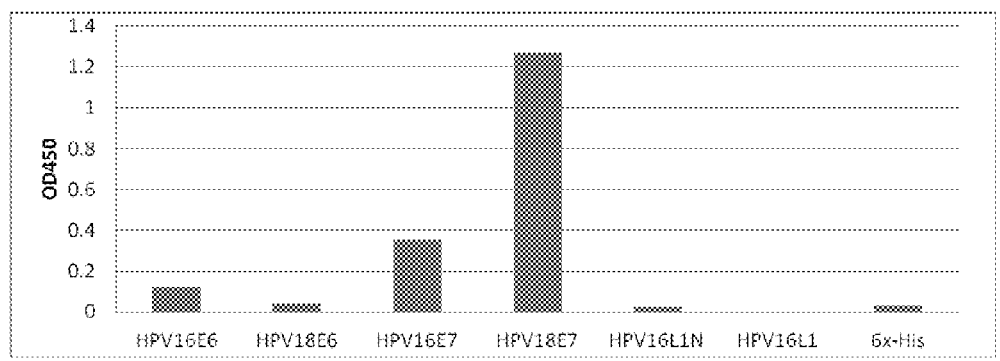
FIG. 11 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

As another example to demonstrate a monoclonal antibody capable of binding to two or more HPV viral proteins from different HPV type as described in this invention, FIG. 11 shows the specificity of a monoclonal antibody capable of reacting with both recombinant HPV16 E7 and HPV18E7 protein on EIA. The recombinant protein coated on microtiter plate detected by the antibody described herein is in native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody contains HPV E7 common epitope capable of reacting with native form of HPV16 E7, and HPV18 E7 proteins.

FIG. 12A shows the representative image of the dysplasia cells of CIN2 tissues stained by immunohistocytostaining (IHC) using an anti-E6 monolonal antibody. FIG. 12B shows the representative image of the adjacent normal epithelium from the dysplasia tissue of the CIN2 sample of FIG. 12A. FIG. 12C-12D shows the representative image of the dysplasia epithelium of two CIN3 samples stained by IHC using the same anti-E6 monolonal antibody. These data suggest the IHC staining by E6 monoclonal antibody is specific in the nuclear and cytoplasm of dysplasia cells.

Figure 13A:
FIG. 13A shows the representative staining image of the squamocarcinoma (SCC) tissue from tissue microarray using an anti-E7 monolonal antibody in an immunohistocytostaining (IHC) assay.
Figure 13B:
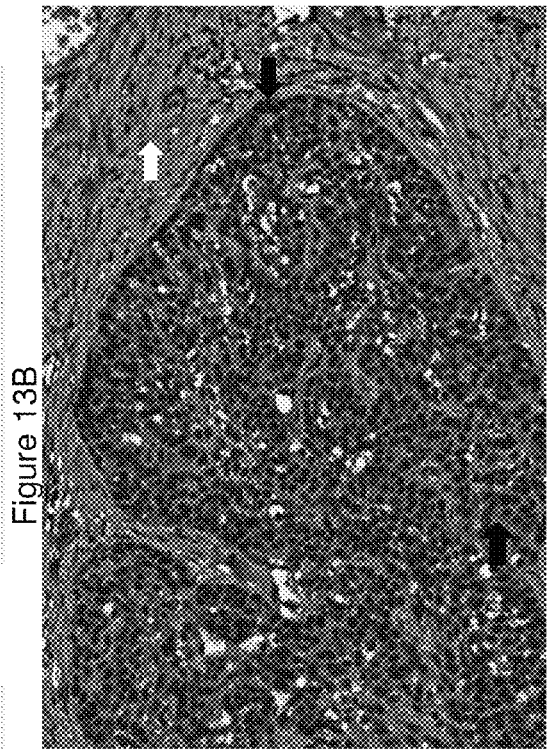
FIG. 13B shows the representative staining image of the normal epithelium (about 15 mm away from the tumor tissue) adjacent the SCC tissue of FIG. 13A.
Figure 13C:
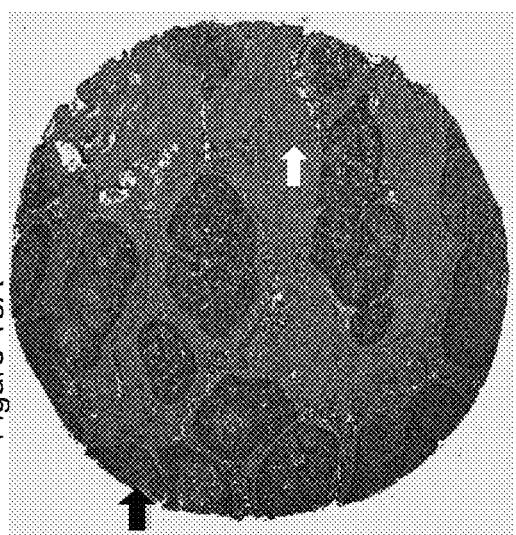
FIG. 13C shows the representative staining image of another SCC sample stained by the same anti-E7 monolonal antibody as used in FIG. 13A in an IHC assay, demonstrating specific IHC staining in the tumor cells by the anti-E7 monoclonal antibody.
Figure 13D:
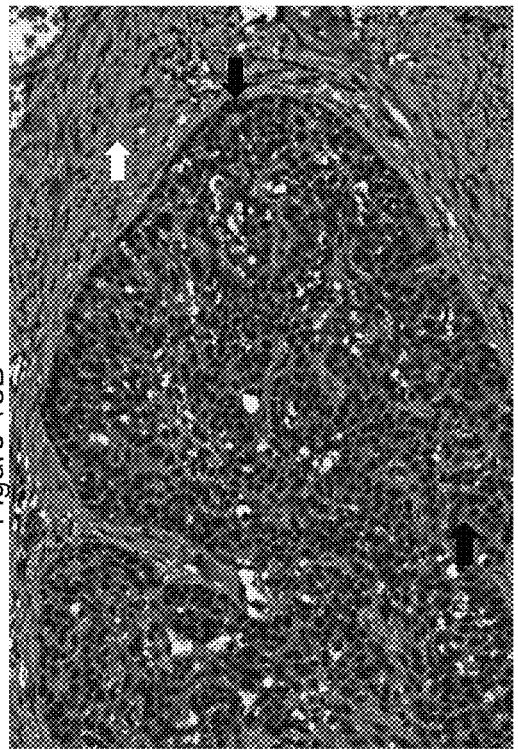
FIG. 13D shows the magnified representative image of the tumor cells from FIG. 13C to view the staining of the cytoplasm of the tumor cells.

As an another example, FIGS. 13A-13D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 13A shows the representative image of the squamocarcinoma (SCC) tissue from tissue microarray stained by IHC using an anti-E7 monoclonal antibody. FIG. 13B shows the representative image of the normal epithelium (15 mm away from the tumor tissue) of the SCC subject from FIG. 13A. FIG. 13C shows the representative image of another SCC sample from tissue microarray stained by IHC using the same anti-E7 monoclonal antibody. FIG. 13D shows the magnified representative image of the tumor cells stained in cytoplasm from FIG. 13C.

As an example, FIG. 14A-14C demonstrate immunocytochemistry assay using anti-HPV antibody. FIG. 14A shows the representative image of cervical cells from a CIN2 cervical scrape sample prepared by thin prep and stained by ICC using a mouse monoclonal anti-HPV E7 antibody. FIG. 14B shows the representative image of cervical cells from a CIN3 cervical scrape sample prepared by thin prep and stained by ICC using a mouse monoclonal anti-E6 antibody. FIG. 14C shows the representative image of cervical cells from an adenocarcinoma (ADC) cervical scrape sample prepared by thin prep and stained by ICC using the same anti-E6 antibody shown in FIG. 14B.

In addition, the monoclonal antibodies generated using methods of the invention are useful to detect infection by oncogenic HPVs, such as infection by high risk HPV types and/or low risk HPV types. As an example, antibodies raised against a recombinant protein HPV16 E6 oncoprotein generated by the method of invention are able to recognize E6 proteins present inside the cells of clinical samples due to single or multiple HPV infection, and react with E6 proteins from high risk HPV types (such as HPV-16, HPV-18, HPV-31, HPV-33, HPV-45, HPV-52, HPV-58, etc.) or low risk HPV types (HPV-6, etc). In addition, a single anti-E6 monoclonal antibody can detect multiple HPV infection in a clinical sample, having two or more HPV types, such as the combination of HPV-16, HPV-18, HPV-51, HPV-52, HPV-58, among others.

HPV Monoclonal Antibody Development:

Recombinant HPV E6, E7 or L1 proteins expressed in *E coli* was purified, concentrated, and dialyzed with PBS to be used as immunogen. Immunization of mice was followed by standard procedure. Titer of the obtained serum was tested by ELISA followed by periodical boosting and bleeding. When the titer of the serum of the mice reaches optimal, fusion of the spleen cells of the mice with tumor cells was done by standard procedure. Clones of fused cells, e.g., hybridoma cells, were further cultured.

Hybridoma screening: To obtain anti-HPV antibody producing hybridoma cells with pan and specific binding capability to various HPV proteins as described in this invention, hybridoma clones were screened with various proteins, including, not only the original immunogens but also additional HPV proteins as positive screening, and unrelated proteins as negative screening. For example, two or more purified HPV recombinant proteins were used to screen against each hybridoma clone to screen and obtain monoclonal antibody-producing hybridoma cell lines and to test and understand the specificity of each antibody-producing hybridoma cell line thus obtained.

As an example of hybridoma screening, antibody-producing hybridoma cells were screened with two or more purified recombinant human papillomavirus proteins such that the monoclonal antibody is capable of reacting with the two or more purified recombinant human papillomavirus proteins. The two or more purified recombinant human papillomavirus proteins include, but are not limited to, HPV 16 E6 protein, HPV 16 E7 protein, HPV 16 L1 protein, HPV 18 E6 protein, HPV18 E7 protein, HPV 18 L1 protein, and other HPV early proteins and late proteins from various HPV types.

The antibody-producing hybridoma cells were screened with positive reactivity to all of the two or more purified recombinant human papillomavirus proteins and negative reactivity to non-HPV proteins, including BSA, his$_6$ tags, GST proteins, maltose binding proteins (MBP), other tags or proteins used in recombinant protein, and other readily available non-HPV proteins. As such, the monoclonal antibodies generated form such hybridoma screening is capable of binding to all of the two or more HPV viral proteins (e.g., the HPV viral proteins present in clinical samples), which correspond to the two or more purified recombinant human papillomavirus proteins.

One example of the two or more purified recombinant human papillomavirus proteins are HPV early proteins such that the monoclonal antibody is capable of reacting with the two or more human papillomavirus early proteins. For example, one hybridoma cell line thus screened and obtained can produce a monoclonal antibody recognizing a common epitope on both HPV16 E6 and HPV16 E7 proteins. Another hybridoma cell line thus screened and obtained can produce a monoclonal antibody recognizing a common epitope on both HPV18 E6 and HPV18 E7 proteins.

Another example of the two or more purified recombinant human papillomavirus proteins includes a purified recombinant human papillomavirus early protein and a purified recombinant human papillomavirus late protein such that the monoclonal antibody produced is capable of reacting with a common epitope on the purified recombinant human papillomavirus early protein and the purified recombinant human papillomavirus late protein. The purified recombinant human papillomavirus early protein may be HPV 16 E6 protein, HPV 16 E7 protein, HPV 18 E6 protein, HPV18 E7 protein, and other HPV recombinant early proteins, and the purified recombinant human papillomavirus late protein may be HPV 16 L1 protein, HPV 18 L1 protein, and other HPV recombinant late proteins. For examples, hybridoma cell lines thus screened and obtained can produce a monoclonal antibody recognizing a common epitope on HPV16 E6, HPV16 E7, and HPV16 L1 proteins; or a monoclonal antibody recognizing a common epitope on HPV16 E6 and HPV18 E6 proteins; or monoclonal antibody recognizing a common epitope on HPV16 E7 and HPV18 E7 proteins; or monoclonal antibody recognizing a common epitope on HPV16 E6, HPV16 E7, HPV16 L1, HPV18 E6, and HPV18 E7 proteins. More examples are provided in the drawings of this invention.

The antibody-producing hybridoma cells were also screened with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types can be HPV 16, HPV 18, and other HPV types. The two or more different HPV types can be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56. As an example, the first and the second purified recombinant human papillomavirus proteins may be recombinant HPV 16 E6 protein, recombinant HPV 16 E7 protein, recombinant HPV 16 L1 protein, recombinant HPV 18 E6 protein, recombinant HPV18 E7 protein, and recombinant HPV 18 L1 protein.

As another example of hybridoma screening, antibody-producing hybridoma cells were screened with positive reactivity to some of the two or more purified recombinant human papillomavirus proteins and negative reactivity to some of the two or more recombinant human papillomavirus proteins and/or non-HPV proteins. As such, the monoclonal antibodies generated form such hybridoma screening is capable of binding to some HPV viral proteins but not other HPV viral proteins.

For example, a monoclonal antibody is obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. Specific monoclonal antibodies obtained includes a monoclonal antibody capable of binding to only HPV 16 E6 protein, but not any other HPV proteins; a monoclonal antibody capable of binding to only HPV 16 E7 protein, but not any other HPV proteins; a monoclonal antibody capable of binding to only HPV 16 L1 protein, but not any other HPV proteins; a monoclonal antibody capable of binding to only HPV 18 E6 protein, but not any other HPV proteins; and a monoclonal antibody capable of binding to only HPV 18 E7 protein, but not any other HPV proteins.

Cloning and production of recombinant proteins encoded by HPV genes. Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Example 1

Cloning and Production of Various Recombinant Proteins Encoded by HPV-16, Early E6 Gene Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcacaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was sub-cloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Other expression vectors which are used as recombinant protein overexpression systems with histidine tag (e.g., $His_6$, $His_8$, etc.), glutathione-S-transferase (GST) fusion, maltose-binding-protein (MBP), among others, can also be used. In addition, the obtained HPV-16 E6 DNA fragment can be sub-cloned into other expression systems, including maltose-binding-protein and glutathione-S-transferase-E6 fusion protein expression systems. Various expression systems can also be used to express E6 recombinant proteins from various HPV types and strains. For example, E6 recombinant protein from HPV-58 was obtained and designated as HPV-16-MBP-E6.

His tagged-HPV16-E6 and MBP-HPV-E6 recombinant proteins were expressed in *E. coli* BL21(DE3) using IPTG driven induction. After two hour induction of protein expression at 37° C., GST-E6 or MBP-E6 recombinant proteins using standard protocols recommended by the suppliers (Amersham and New England Biolabs, respectively) were obtained and purified to a final concentration of about 1 mg/L. Longer induction time and re-flow though on protein purification column were found to generate higher protein yield, resulting in highly concentrated purified recombinant proteins at a yield of about 2-10 mg/L). The purity of the recombinant GST-E6 proteins was estimated to be >90% based on PAGE analysis. Recombinant E6 fusion proteins was used to detect the presence of E6 antibody on clinical samples and was also be used as immunogens for production of polyclonal antiserum and monoclonal antibodies.

FIGS. 15A and 15B demonstrate the expression of full-length HPV-16 E6 recombinant protein induced by IPTG analyzed by SDS-PAGE and western blot, respectively, using anti-E6 monoclonal antibody (MAb1-1). The molecular weight of the resulting His-tagged-HPV16-E6 recombinant protein is about 20.5 KD. The western blot was performed on a PVDF membrane using an anti-E6 monoclonal antibody, which is a mouse antibody, followed by a secondary antibody, an alkaline peroxidase (AP)-goat-anti-mouse IgG1, and visualized by the reaction of NBT and BCIP substrate mixture. The results showed that a single major protein band and thus pure recombinant E6 protein was purified. The purity of the recombinant E6 proteins was estimated to be about 90% or more based on PAGE analysis.

The purified recombinant E6 proteins as shown in FIG. 15 were used in one or more immunological assays, for example, to be used as a detecting antibody in antibody assays, etc. The purified recombinant E6 proteins were also used to as immunogens for generating antiserum, polyclonal antibody, and monoclonal antibodies specific against HPV-16 E6 protein.

Figure 15C:
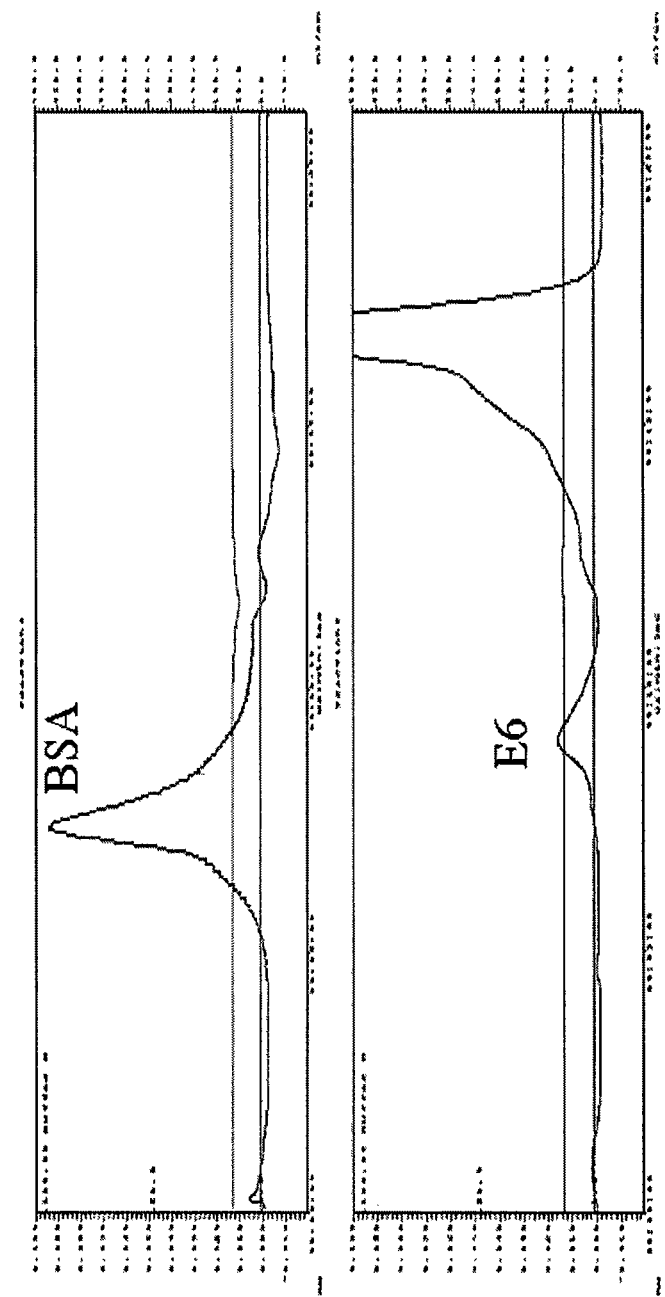
FIG. 15C demonstrates the result of gel filtration column chromatography of the purified recombinant E6 protein, demonstrating that the purified recombinant proteins HPV-16-E6 is a monomeric soluble protein. The purified recombinant E6 protein is eluted later than BSA.

FIG. 15C demonstrates the result of gel filtration column chromatography of the purified recombinant E6 protein, demonstrating that the purified recombinant protein HPV-16-E6 is a monomeric soluble protein with molecular size about 20.5 kDa. The purified recombinant E6 protein is eluted later than BSA.

Example 2

Cloning and Production of Recombinant Proteins Encoded by HPV-16 Early E7 Gene

Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgc 3' (SEQ ID NO. 9) and 5' ccgGAATTCttatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was sub-cloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

Figure 16:
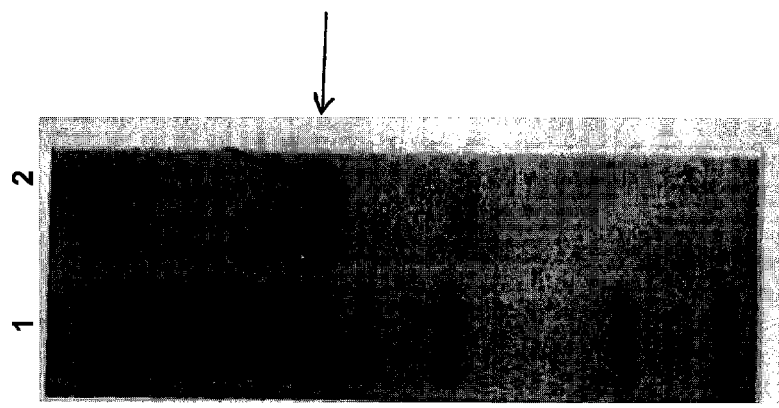
FIG. 16 is a SDS-PAGE gel, showing one exemplary purified recombinant HPV-16-E7 proteins according to one or more embodiments of the invention.

FIG. 16 is a SDS-PAGE gel, showing one exemplary purified recombinant HPV-16-E7 proteins. As shown in FIG. 3, the HPV-16-E7 recombinant proteins is purified to homogeneity as a major single band with a molecular weight of 37.2 KDa as indicated by an arrow.

Figure 17:
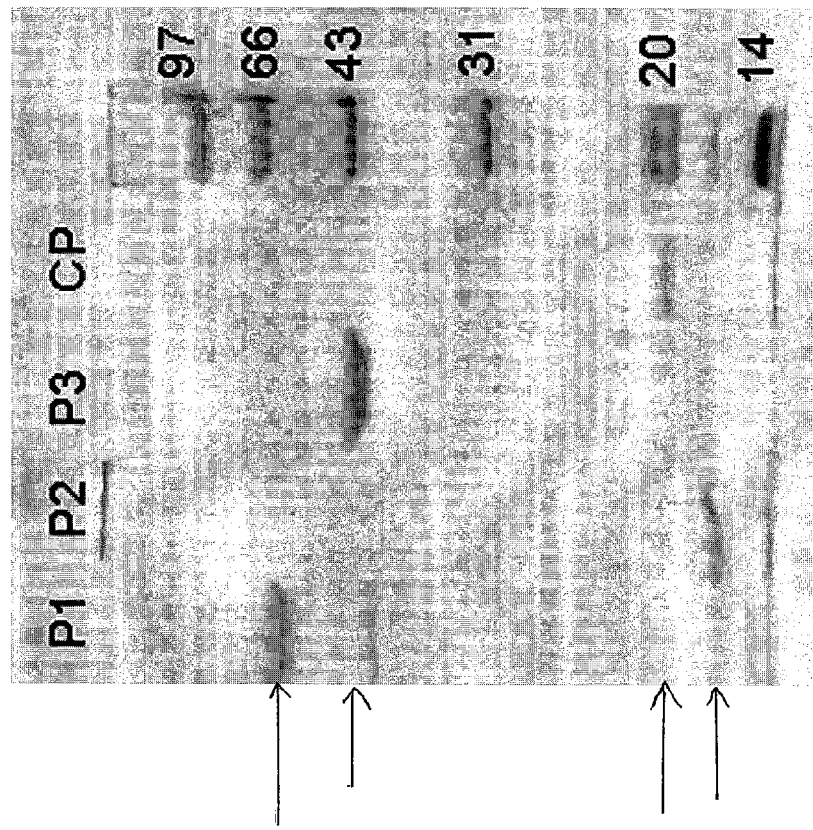
FIG. 17 demonstrates SDS-PAGE of three exemplary purified HPV early gene recombinant proteins by commassie blue staining according to one or more embodiments of the invention. P1: HPV-58-E6-MBP fusion protein; P3: MBP protein; P2: HPV-16-E7-His fusion protein; CP: HPV-16-E6-His fusion protein.

FIG. 17 demonstrates SDS-PAGE of three exemplary purified HPV recombinant proteins by commassie blue staining according to one or more embodiments of the invention. Recombinant fusion proteins were obtained for different HPV types, such as different high risk HPV types, e.g., HPV-16, HPV-18, HPV-58, etc. P1 indicates a purified recombinant HPV-58-E6-MBP fusion protein as compared to P3 for a MBP protein alone. P2 indicates a purified recombinant HPV-16-E7-His fusion protein and CP indicates a purified recombinant HPV-16-E6-His fusion protein.

The invention claimed is:

1. A method for determining a disease stage of human papillomavirus (HPV) infection in a human subject comprising:
   contacting a tissue sample or a cell sample with a first one or more monoclonal antibodies, wherein
      the tissue sample or the cell sample comprises protein, and the sample is obtained from a human subject;
      the first one or more monoclonal antibodies specifically bind to two or more viral proteins, and the one or more monoclonal antibodies are capable of binding in situ to the viral proteins in the tissue sample or the cell sample, wherein
         the viral proteins comprise two or more HPV E6 proteins from different HPV types in a clinical sample and/or two or more HPV E7 proteins from different HPV types in a clinical sample; and
      said contacting takes place under conditions that promote specific binding of said one or more monoclonal antibodies;
   contacting the tissue sample or the cell sample with a second one or more antibodies that specifically binds to a cellular protein;
   determining presence, absence, or an amount of the two or more viral proteins in said sample that specifically binds to the first one or more monoclonal antibodies based at least in part on a measure of specific binding of the first one or more monoclonal antibodies to the sample contacted by the one or more monoclonal antibodies;
   determining presence, absence, or an amount of the cellular protein in said sample that specifically binds to the second one or more antibodies based at least in part on a measure of specific binding of the second one or more antibodies to the sample contacted by the second one or more antibodies; and
   determining said disease stage of papillomavirus infection in said human subject based on said determined presence, absence, or amount of the viral proteins and the cellular protein in said sample.

2. The method of claim 1 wherein said sample comprises a tissue sample, or a cell sample, and said determining comprises an immunocytochemistry assay, a immunohistochemistry assay or a flow cytometry assay.

3. The method of claim 1 wherein said determining said disease stage comprises determining the presence or absence of HSIL.

4. The method of claim 1 wherein said determining said disease stage comprises determining the presence or absence of late stage HPV infection.

5. The method of claim 1 wherein said determining said disease stage comprises determining the presence or absence of high grade dysplasia.

6. The method of claim 1 wherein said determining said disease stage comprises determining the presence or absence of a disease stage ≥CIN2.

7. The method of claim 1 wherein said disease stage is ≥CIN2 or <CIN2.

8. The method of claim 7 wherein said ≥CIN2 is CIN2/3.

9. The method of claim 1 wherein said disease stage is HSIL.

10. The method of claim 1 wherein said different HPV types comprises HPV-6, HPV-11, HPV-16, HPV-18, HPV-31, HPV-33, HPV-39, HPV-44, HPV-45, HPV-51, HPV-52, HPV-53, HPV-58, HPV-59, and HPV-66.

11. The method of claim 10 wherein said papillomavirus comprises one or more viruses selected from the group consisting of HPV-16 and HPV-18.

12. The method of claim 1 wherein said cell sample comprises normal cells, ASC-US cells, ASC-H cells, LSIL cells, HSIL cells, ADC cells, AGC cells or SCC cells.

13. The method of claim 1 wherein said tissue sample is benign, CIN1, CIN2, CIN3, SCC, AGC or ADC.

14. The method of claim 1 further comprising:
   obtaining a second sample from said human subject, said sample comprising a cell sample; and
   performing a cytological Papanicolaou smear assay on said sample.

15. The method of claim 1 further comprising:
   obtaining a second sample from said human subject, said sample comprising a nucleic acid; and
   performing a nucleic acid hybridization assay for human papillomavirus on said sample.

16. The method of claim 1, wherein the cellular protein is $p16^{INK4a}$.

17. The method of claim 1, wherein the cellular protein is selected from a group comprising $p16^{INK4a}$, pRB, p53, E2F, E2F activated cell cycle protein, cyclin dependent kinase, CDK4, CDK6, Ki-67 (MIB-1), MYC protein, cyclin-A, cyclin-B, cyclin-E, telomerase-TERC, MCM2, TOP2A, heat shock protein 40 (HSP40), heat shock protein 60 (HSP60), heat shock protein 70 (HSP70), CA9/MN, laminin5, brn-3a, CDK N2, topoisomerase 2A, microsome maintenance protein-2, microsome maintenance protein-4, microsome maintenance protein-5, survivin, VEGF, p27 (kip1), and p21 (waf).

18. A kit for determining a disease stage of papillomavirus infection in a human subject comprising a first one or more monoclonal antibodies, wherein
   the first one or more monoclonal antibodies specifically bind to two or more HPV E7 proteins from different HPV types and/or two or more HPV E6 proteins from different HPV types, and the first one or more monoclonal antibodies is capable of binding in situ to the protein in a clinical sample, wherein
      the clinical sample is a tissue sample comprising proteins or a cell sample comprising proteins and the sample is obtained from a human, and
   a second one or more antibodies that specifically binds to a cellular protein.

19. The method of claim 18, wherein the cellular protein is $p16^{INK4a}$.

20. The method of claim 18, wherein the cellular protein is selected from a group comprising $p16^{INK4a}$, pRB, p53, E2F, E2F activated cell cycle protein, cyclin dependent kinase, CDK4, CDK6, Ki-67 (MIB-1), MYC protein, cyclin-A, cyclin-B, cyclin-E, telomerase-TERC, MCM2, TOP2A, heat shock protein 40 (HSP40), heat shock protein 60 (HSP60), heat shock protein 70 (HSP70), CA9/MN, laminin5, brn-3a, CDK N2, topoisomerase 2A, microsome maintenance protein-2, microsome maintenance protein-4, microsome maintenance protein-5, survivin, VEGF, p27 (kip1), and p21 (waf).

21. The method of claim 18 wherein said different HPV types comprises HPV-6, HPV-11, HPV-16, HPV-18, HPV-31, HPV-33, HPV-39 HPV-44, HPV-45, HPV-51, HPV-52, HPV-53, HPV-58, HPV-59, and HPV-66.

* * * * *